United States Patent
Caroff et al.

(10) Patent No.: US 9,951,063 B2
(45) Date of Patent: Apr. 24, 2018

(54) 8-(PIPERAZIN-1-YL)-1,2,3,4-TETRAHYDRO-ISOQUINOLINE DERIVATIVES

(71) Applicant: IDORSIA PHARMACEUTICALS LTD, Allschwil (CH)

(72) Inventors: Eva Caroff, Allschwil (CH); Rémy Castro, Allschwil (CH); Emmanuel Meyer, Allschwil (CH); Thierry Kimmerlin, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/128,846

(22) PCT Filed: Mar. 23, 2015

(86) PCT No.: PCT/IB2015/052098
§ 371 (c)(1),
(2) Date: Sep. 23, 2016

(87) PCT Pub. No.: WO2015/145322
PCT Pub. Date: Oct. 1, 2015

(65) Prior Publication Data
US 2017/0107214 A1    Apr. 20, 2017

(30) Foreign Application Priority Data
Mar. 24, 2014  (WO) .................. PCT/IB2014/060092

(51) Int. Cl.
| C07D 401/14 | (2006.01) |
| C07D 413/14 | (2006.01) |
| C07D 417/14 | (2006.01) |
| C07D 471/04 | (2006.01) |
| A61K 31/496 | (2006.01) |

(52) U.S. Cl.
CPC ......... *C07D 471/04* (2013.01); *C07D 401/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| 7,589,199 B2 | 9/2009 | Pennell et al. |
| 7,842,693 B2 | 11/2010 | Pennell et al. |
| 8,324,216 B2 | 12/2012 | Pennell et al. |
| 8,450,317 B2 | 5/2013 | Kowalski et al. |
| 8,889,677 B2 | 11/2014 | Grauert et al. |
| 9,266,876 B2 | 2/2016 | Caroff et al. |
| 2004/0082571 A1 | 4/2004 | Pennell et al. |
| 2005/0256130 A1 | 11/2005 | Pennell et al. |
| 2006/0276465 A1 | 12/2006 | Kawahara et al. |
| 2010/0094006 A1 | 4/2010 | Nam et al. |
| 2010/0280028 A1 | 12/2010 | Kowalski et al. |
| 2011/0136823 A1 | 6/2011 | Deprez et al. |
| 2013/0072497 A1 | 3/2013 | Lorsbach et al. |
| 2016/0176862 A1 | 6/2016 | Caroff et al. |

FOREIGN PATENT DOCUMENTS

| EP | 1698620 A1 | 9/2006 |
| WO | WO 2011/146182 A1 | 11/2001 |
| WO | WO 02/059107 A1 | 8/2002 |
| WO | WO 02/059108 A1 | 8/2002 |
| WO | WO 02/070511 A1 | 9/2002 |
| WO | WO 2005/035534 A1 | 4/2005 |
| WO | WO 2005/040136 A1 | 5/2005 |
| WO | WO 2005/042516 A2 | 5/2005 |
| WO | WO 2005/044797 A1 | 5/2005 |
| WO | WO 2005/051304 A2 | 6/2005 |
| WO | WO 2006/088836 A2 | 8/2006 |
| WO | WO 2006/088837 A2 | 8/2006 |
| WO | WO 2006/088840 A1 | 8/2006 |

(Continued)

OTHER PUBLICATIONS

Horuk, Nature Reviews/Drug Discovery, vol. 8, pp. 23-33 (2009).*
Andrews et al. J. Med. Chem. 2016, 59, 2894-2917.*
Pease Expert Opinion on Drug Discovery, vol. 12, No. 2, 159-168 (2017).*
Wijtmans et al. ChemMedChem 2008, 3, 861-872.*
Fisher J. M. et al., Privileged structure-based ligands for melanocortin receptors—tetrahydroquinolines, indoles, and aminotetralines, Bioorganic & Medicinal Chemistry Letters, 2005, p. 4459-4462, 15, www.sciencedirect.com.
Greene T.W. & Wuts P.G.M., Protective Groups in Organic Synthesis, Third Edition, 1999, Wiley-Interscience, (3 pages provided).

(Continued)

*Primary Examiner* — Emily Bernhardt
(74) *Attorney, Agent, or Firm* — Arent Fox LLP

(57) ABSTRACT

The invention relates to compounds of Formula (I) wherein $R^1$, $R^2$, $R^3$, $R^4$ and $R^5$ are as described in the description; to pharmaceutically acceptable salts thereof, and to the use of such compounds as medicaments, especially as modulators of the CXCR3 receptor.

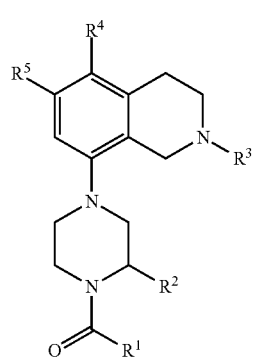

Formula (I)

15 Claims, No Drawings

(56) References Cited

FOREIGN PATENT DOCUMENTS

| | | |
|---|---|---|
| WO | WO 2006/088919 A2 | 8/2006 |
| WO | WO 2006/088920 A1 | 8/2006 |
| WO | WO 2006/088921 A2 | 8/2006 |
| WO | WO 2006/091428 A2 | 8/2006 |
| WO | WO 2005/003127 A1 | 9/2006 |
| WO | WO 2007/002742 A1 | 1/2007 |
| WO | WO 2007/014290 A2 | 2/2007 |
| WO | WO 2007/047202 A1 | 4/2007 |
| WO | WO 2007/064553 A2 | 6/2007 |
| WO | WO 2007/070433 A2 | 6/2007 |
| WO | WO 2007/076318 A2 | 7/2007 |
| WO | WO 2007/100610 A2 | 9/2007 |
| WO | WO 2007/109238 A1 | 9/2007 |
| WO | WO 2008/008453 A1 | 1/2008 |
| WO | WO 2008/013622 A2 | 1/2008 |
| WO | WO 2008/013925 A2 | 1/2008 |
| WO | WO 2008/079279 A1 | 7/2008 |
| WO | WO 2008/091580 A2 | 7/2008 |
| WO | WO 2008/091594 A2 | 7/2008 |
| WO | WO 2009/020534 A2 | 2/2009 |
| WO | WO 2009/055514 A2 | 4/2009 |
| WO | WO 2009/079490 A1 | 6/2009 |
| WO | WO 2009/094407 A2 | 7/2009 |
| WO | WO 2009/094445 A2 | 7/2009 |
| WO | WO 2009/105435 A1 | 8/2009 |
| WO | WO 2009/132785 A1 | 11/2009 |
| WO | WO 2010/037479 A1 | 4/2010 |
| WO | WO 2010/065579 A2 | 6/2010 |
| WO | WO 2010/066353 A1 | 6/2010 |
| WO | WO 2010/126811 A1 | 11/2010 |
| WO | WO 2010/126851 A1 | 11/2010 |
| WO | WO 2010/149275 A1 | 12/2010 |
| WO | WO 2011/018401 A1 | 2/2011 |
| WO | WO 2011/018415 A2 | 2/2011 |
| WO | WO 2011/051243 A1 | 5/2011 |
| WO | WO 2011/051244 A1 | 5/2011 |
| WO | WO 2011/076699 A1 | 6/2011 |
| WO | WO 2011/084985 A1 | 7/2011 |
| WO | WO 2011/134969 A1 | 11/2011 |
| WO | WO 2011/144586 A1 | 11/2011 |
| WO | WO 2011/147765 A1 | 12/2011 |
| WO | WO 2012/020060 A1 | 2/2012 |
| WO | WO 2012/025557 A1 | 3/2012 |
| WO | WO 2012/055837 A1 | 5/2012 |
| WO | WO 2012/069633 A1 | 5/2012 |
| WO | WO 2012/082580 A2 | 6/2012 |
| WO | WO 2012/104273 A1 | 8/2012 |
| WO | WO 2012/107475 A1 | 8/2012 |
| WO | WO 2012/107477 A1 | 8/2012 |
| WO | WO 2012/171337 A1 | 12/2012 |
| WO | WO 2013/037768 A1 | 3/2013 |
| WO | WO 2013/056911 A1 | 4/2013 |
| WO | WO 2013/056915 A1 | 4/2013 |
| WO | WO 2013/083741 A1 | 6/2013 |
| WO | WO 2013/093842 A1 | 6/2013 |
| WO | WO 2013/107761 A1 | 7/2013 |
| WO | WO 2013/114332 A1 | 8/2013 |
| WO | WO 2013/127808 A1 | 8/2013 |
| WO | WO 2013/127748 A1 | 9/2013 |
| WO | WO 2014/062938 A1 | 4/2014 |
| WO | WO 2014/075873 A1 | 5/2014 |
| WO | WO 2014/075874 A1 | 5/2014 |
| WO | WO 2014/092100 A1 | 6/2014 |
| WO | WO 2014/206896 A1 | 12/2014 |
| WO | WO 2015/011099 A1 | 1/2015 |
| WO | WO 2016/113344 A1 | 7/2016 |
| WO | WO 2016/113346 A1 | 7/2016 |

OTHER PUBLICATIONS

Groom J.R. & Luster A.D., CXCR3 in T cell function, Experimental Cell Research, 2011, p. 620-631, 317, www.sciencedirect.com.

Groom J.R. & Luster A.D., CXCR3 ligands: redundant, collaborative and antagonistic functions, Immunology and Cell Biology, 2011, p. 1-9, 89, 207.

Hancock W.W. et al., Requirement of the Chemokine Receptor CXCR3 for Acute Allograft Rejection, Brief Definitive Report, 200, p. 1515-1519, vol. 192, No. 10, J. Exp. Med.

Jenh CH et al., A selective and potent CXCR3 antagonist SCH 546738 attenuates the development of autoimmune diseases and delays graft rejection, BMC Immunology, 2012, p. 1-14, 13:2, BioMed Central.

Lacotte et al., CXCR3, Inflammation, and Autoimmune Diseases, Contemporary Challenges in Autoimmunity, 2009, p. 310-317, 1173, New York Academy of Sciences.

Lammers K.M. et al., Gliandin Induces an Increase in Intestinal Permeability and Zonulin Release by Binding to the Chemokine Receptor CXCR3, Gastroenterology, 2008, p. 194-204, vol. 165, No. 1.

Mach F. et al., Differential expression of three T lymphocyte-activating CXC chemokines by human atheroma-associated cells, The Journal of Clinical Investigation, 1999, p. 1041-1050, vol. 104, No. 8.

McGuinness B.F. et al., Novel CXCR3 Antagonists with a Piperazinyl-Piperidine Core, Bioorganice & Medicinal Chemistry Letters, 2009, (doi:10.1016/j.bmcl.2009.07.020).

Menke J., Distinct Roles of CSF-1 Isoforms in Lupus Nephritis, J American Society of Nephrology, 2011, p. 1821-1833, 22, www.jasn.org.

Mohan K. & Issekutz T.B., Blockade of Chemokine Receptor CXCR3 Inhibits T Cell Recruitment to Inflamed Joints and Decreases the Severity of Adjuvant Arthritis, The Journal of Immunology, 2007, p. 8463-8469, 179, The American Association of Immunologists, Inc., Maryland.

Nie L. et al., Attenuation of acute lung inflammation induced by cigarette smoke in CXCR3 knockout mice, Respiratory Research, 2008, p. 1-10, 9:82, BioMed Central.

Pradelli et al., Antagonism of chemokine recepotor CXCR3 inhibits osteosarcoma metastasis to lungs, Int, J. Cancer, 2009, p. 2586-2594, 125, International Union Against Cancer, UICC.

Prokowicz A. et al., Optimization of a biaryl series of CXCR3 antagonists, Aug. 19-23, 2012, 244th ACS National Meeting, Philadelphia, Pennsylvania, (264 pages provided).

Reinhart P.H. et al., Identification of anti-inflammatory targets for Huntington's disease using a brain slice-based screening assay, Neurobiology of Disease 43, 2011, p. 248-256.

Remington, The Science and Practice of Pharmacy 21st Edition, Part 5, 2005, Pharmaceutical Manufacturing, Lippincott Williams & Wilkins, (5 pages provided).

Sakthivel S.K. et al., CXCL10 blockade protects mice from cyclophosphamide-induced cystitis, Journal of Immune Based Therapies and Vaccines, 2008, p. 1-32, 6:6.

Seatta M. et al., Increased Expression of the Chemokine Receptor CXCR3 and Its Ligand CKCL10 in Peripheral Airways of Smokers with Chronic Obstructive Pulmonary Disease, American Journal of Respiratory and Critical Care Medicine, 2002, p. 1404-1409, vol. 165.

Singh U.P. et al., CXCL-10-Producing Mucosal CD4+ T Cells, NK Cells, and NKT Cells are Associated with Chronic Colitis in IL-10-/-Mice, Which Can Be Abrogated by Anti-CXCL10 Antibody Inhibition, J Interferon Cytokine Res., Jan. 2008, p. 31-43, 28(1), NIH Public Access.

Stahl P.H. & Wermuth C.G., Handbook of Pharmaceutical Salts Properties, Selection, and Use, 2008, p. 329-350, International Union of Pure and Applied Chemistry (IUPAC), VHCA & Wiley-VCH, Germany.

Tacke F. et al., Serum chemokine receptor CXCR3 ligands are associated with progression, organ dysfunction and complications of chronic liver diseases, Liver International, 2011, p. 840-849, Liver International ISSN 1478-3223, John Wiley & Sons A/S.

Trentin L. et al., The chemokine receptor CXCR3 is expressed on malignant B cells and mediates chemotaxis, The Journal of Clinical Investigation, 1999, p. 115-121, vol. 104, No. 1.

(56) References Cited

OTHER PUBLICATIONS

Van Weering H.R.J. et al., CXCL10/CXCR3 Signaling in Glia Cells Differentially Affects NMDA-Induced Cell Death in CA and DG Neurons of the Mouse Hippocampus, Hippocampus, 2011, 21, p. 1-13, Wiley-Liss, Inc.
Veillard N.R. et al., Differential Influence of Chemokine Receptors CCR2 and CXCR3 in Development of Atherosclerosis in Vivo, Circulation:Journal of the American Heart Association, 2005, p. 870-878, 112, American Heart Association, Texas.
Wang Y. et al., Camphor sulfonamide derivatives as novel, potent and selective CXCR3 antagonists, Bioorganic & Medicinal Chemistry Letters, 2009, p. 114-118, 19.
Watson R.J. et al., Development of CXCR3 antagonists. Part 2: Identification of 2-amino(4-piperidinyl)azoles as potent CXCR3 antagonists, Bioorganic & Medicinal Chemistry Letters, 2007, p. 6806-6810, 17, www.sciencedirect.com.
Wijtmans M. et al., Towards Small-Molecule CXCR3 Ligands with Clinical Potential, ChemMedChem, 2008, p. 861-872, 3, Wiley-VCH Verlag GmbH & Co.
Wouters J. & Quere L, Pharmaceutical Salts and Co-crystals, 2012, p. vii-xiv, RSC Publishing, Cambridge, United Kingdom.
Zhang F. et al., Pyridinylquinazolines Selectively Inhibit Human Methionine Aminopeptidase-1 in Cells, Journal of Medicinal Chemistry, 2013, p. 3996-4016, 56, American Chemical Society Publications.
Antonelli, A. et al., "CXCL10 ($\alpha$) and CCL2 ($\beta$) chemokines in systemic sclerosis—a longitudinal study" Rheumatology, vol. 47, 2008, pp. 45-49.
Busuttil, A. et al., "CXCR3 ligands are augmented during the pathogenesis of pulmonary sarcoidosis" European Respiratory Journal, vol. 34, No. 3, 2009, pp. 676-686.
Cameron, Cheryl M. et al., "Gene Expression Analysis of Host Innate Immune Responses during Lethal H5N1 Infection in Ferrets" Journal of Virology, vol. 82, No. 22, Nov. 2008, pp. 11308-11317.
Campanella, Gabriele S. V. et al., "Chemokine receptor CXCR3 and its ligands CXCL9 and CXCL10 are required for the development of murine cerebral malaria" PNAS, vol. 105, No. 12, Mar. 25, 2008, pp. 4814-4819.
Chen, Shu-Cheng et al., "Expression of chemokine receptor CXCR3 by lymphocytes and plasmacytoid dendritic cells in human psoriatic lesions" Arch Dermatol Res, May 19, 2009, No. of Pages—11.
Cho, Jungsook et al., "Chronic CXCL10 alters neuronal properties in rat hippocampal culture" Journal of Neuroimmunology, 2009, No. of Pages—9.
Comini-Frota, Elizabeth R. et al., "Evaluation of Serum Levels of Chemokines during Interferon—$\beta$ Treatment in Multiple Sclerosis Patients—A 1-Year, Observational Cohort Study" CNS Drugs, vol. 25(11), 2011, pp. 971-981.
Costa, Claudia et al., "CXCR3 and CCR5 Chemokines in Induced Sputum From Patients With COPD" CHEST, vol. 133, 2008, pp. 26-33.
Crescioli, Clara et al., "Inflammatory response in human skeletal muscle cells: CXCL10 as a potential therapeutic target" European Journal of Cell Biology, 2011, No. of Pages—11.
Enghard, P. et al., "CXCR3+34 CD4+ T Cells Are Enriched in Inflamed Kidneys and Urine and Provide a New Biomarker for Acute Nephritis Flares in Systemic Lupus Erythematosus Patients" Arthritis & Rheumatism, vol. 60, No. 1, Jan. 2009, pp. 199-206.
Feferman, Tali et al., "Suppression of experimental autoimmune myasthenia gravis by inhibiting the signaling between IFN—$\gamma$ inducible protein 10 (IP-10) and its receptor CXCR3" Journal of Neuroimmunology, 2009, No. of Pages—9.
Fulton, Amy M. et al., "The Chemokine Receptors CXCR4 and CXCR3 in Cancer" Evolving Therapies, University of Maryland Marlene and Stewart Greenebaum Cancer Center and Department of Pathology, Current Oncology Reports, 2009, 11: 125-131.
He, Shan et al., "A New Approach to the Blocking of Alloreactive T Cell-Mediated Graft-versus-Host Disease by In Vivo Administration of Anti-CXCR3 Neutralizing Antibody" The Journal of Immunology, vol. 181, 2008, pp. 7581-7592.
Howard, O.M. Zack et al., "Autoantigens signal through chemokine receptors: uveitis antigens induce CXCR3- and CXCR5-expressing lymphocytes and immature dendritic cells to migrate" Blood, vol. 105, No. 11, Jun. 1, 2005, pp. 4207-4214.
Lammers, Karen M., "Gliadin Induces an Increase in Intestinal Permeability and Zonulin Release by Binding to the Chemokine Receptor CXCR3" Gastroenterology, vol. 135(1), Jul. 2008, pp. 194-204.
Lin, Yi et al., "Attenuation of antigen-induced airway hyperresponsiveness and inflammation in CXCR3 knockout mice" Respiratory Research, vol. 12:123, 2011, No. of Pages—8.
Liu, Che et al., "Chemokine receptor CXCR3 promotes growth of glioma" Carcinogenesis, vol. 32, No. 2, 2010, pp. 129-137.
Loos, Tamara et al., "TLR ligands and cytokines induce CXCR3 ligands in endothelial cells: enhanced CXCL9 in autoimmune arthritis" Laboratory Investigation, vol. 86, 2006, pp. 902-916.
Maru, Seema V. et al., "Chemokine production and chemokine receptor expression by human glioma cells: Role of CXCL10 in tumour cell proliferation" Journal of Neuroimmunology, 2008, No. of Pages—11.
Matl, Ivo et al., "Potential Predictive Markers in Protocol Biopsies for Premature Renal Graft Loss" Kidney & Blood Pressure Research, vol. 33, 2010, pp. 7-14.
Menke, Julia et al., "CXCL9, but not CXCL10, Promotes CXCR3-Dependent Immune-Mediated Kidney Disease" Journal of the American Society of Nephrology, vol. 19, 2008, pp. 1177-1189.
Mohan, Karkada et al., "Blockade of Chemokine Receptor CXCR3 Inhibits T Cell Recruitment to Inflamed Joints and Decreases the Severity of Adjuvant Arthritis" The Journal of Immunology, vol. 179, 2007, pp. 8463-8469.
Ogawa, Teruyuki et al., "CXCR3 Binding Chemokine and TNFSF14 Over Expression in Bladder Urothelium of Patients With Ulcerative Interstitial Cystitis" The Journal of Urology, vol. 183, Mar. 2010, pp. 1206-1212.
Pradelli, Emmanuelle et al., "Antagonism of chemokine receptor CXCR3 inhibits osteosarcoma metastasis to lungs" Int J Cancer, Dec. 1, 2009, vol. 125(11), pp. 2586-2594.
Press, R. et al., "Aberrated Levels of Cerebrospinal Fluid Chemokines in Guillain-Barre Syndrome and Chronic Inflammatory Demyelinating Polyradiculoneuropathy" Journal of Clinical Immunology, vol. 23, No. 4, Jul. 2003, pp. 259-267.
Reinhart, Peter H. et al., "Identification of anti-inflammatory targets for Huntington's disease using a brain slice-based screening assay" Neurobiology of Disease, vol. 43, 2011, pp. 248-256.
Romagnani, Paola et al., "CXCL10: A candidate biomarker in transplantation" Clinica Chimica Acta, 2012, No. of Pages—10.
Ross, David J. et al., "Type I immune response cytokine-chemokine cascade is associated with pulmonary arterial hypertension" The Journal of Heart and Lung Transplantation, 2012, No. of Pages—9.
Ruschpler, Peter et al., "High CXCR3 expression in synovial mast cells associated with CXCL9 and CXCL10 expression in inflammatory synovial tissues of patients with rheumatoid arthritis" Arthritis Research & Therapy, vol. 5, No. 5, Jun. 26, 2003, pp. R241-R252.
Sakthivel, Senthilkumar K., "CXCL10 blockade protects mice from cyclophosphamide-induced cystitis" Journal of Immune Based Therapies and Vaccines, 6:6, 2008, pp. 1-14
Schroepf, Sebastian et al., "Strong Overexpression of CXCR3 Axis Components in Childhood Inflammatory Bowel Disease" Inflamm Bowel Dis, 2010, No. of Pages—9.
Seung, Edward et al., "Inhibiting CXCR3-Dependent CD8+ T Cell Trafficking Enhances Tolerance Induction in a Mouse Model of Lung Rejection" The Journal of Immunology, vol. 186, 2011, pp. 6830-6838.
Sporici, Romeo et al., "CXCR3 blockade inhibits T-cell migration into the CNS during EAE and prevents development of adoptively transferred, but not actively induced, disease" European Journal of Immunology, vol. 40, 2010, pp. 2751-2761.
Steinmetz, Oliver M. et al., "CXCR3 Mediates Renal Th1 and Th17 Immune Response in Murine Lupus Nephritis" The Journal of Immunology, 2009, 183, No. of Pages—12.

(56) References Cited

OTHER PUBLICATIONS

Suzaki, Y. et al., "A small-molecule compound targeting CCR5 and CXCR3 prevents airway hyperresponsiveness and inflammation" European Respiratory Journal, vol. 31, No. 4, 2008, pp. 783-789.

Tacke, Frank et al., "Serum chemokine receptor CXCR3 ligands are associated with progression, organ dysfunction and complications of chronic liver diseases" Liver International, ISSN 1478-3223, pp. 840-849.

Uno, Sae et al., "Expression of chemokines, CXC chemokine ligand 10 (CXCL10) and CXCR3 in the inflamed islets of patients with recent-onset autoimmune type 1 diabetes" The Japan Endocrine Society, Sep. 7, 2010, No. of Pages—6.

Uzawa, Akiyuki et al., "Expression of chemokine receptors on peripheral blood lymphocytes in multiple sclerosis and neuromyelitis optica" BMC Neurology, vol. 10:113, 2010, No. of Pages—5.

Van Wanrooij, Eva J.A. et al., "CXCR3 Antagonist NBI-74330 Attenuates Atherosclerotic Plaque Formation in LDL Receptor-Deficient Mice" Arterioscler Thromb Vasc Biol., vol. 28, Feb. 2008, pp. 251-257.

Van Weering, Hilmar R.J. et al., "CXCL10/CXCR3 Signaling in Glia Cells Differentially Affects NMDA-Induced Cell Death in CA and DG Neurons of the Mouse Hippocampus" Hippocampus, 2010, No. of Pages—13.

Vergote, David et al., "Proteolytic processing of SDF-1α reveals a change in receptor specificity mediating HIV-associated neurodegeneration" PNAS, vol. 103, No. 50, Dec. 12, 2006, pp. 19182-19187.

Walser, Tonya C. et al. "Antagonism of CXCR3 Inhibits Lung Metastasis in a Murine Model of Metastatic Breast Cancer" Cancer Research, vol. 66: (15), Aug. 1, 2006, pp. 7701-7707.

Xia, Qi Meng et al., "Expression of the chemokine receptor CXCR3 on neurons and the elevated expression of its ligand IP-10 in reactive astrocytes: in vitro ERK ½ activation and role in Alzheimer's disease" Journal of Neuroimmunology, vol. 108, Jan. 18, 2000, pp. 227-235.

Yoon, Kyung-Chul et al., "Expression of CXCL9, -10, -11, and CXCR3 in the Tear Film and Ocular Surface of Patients with Dry Eye Syndrome" IOVS, vol. 51, No. 2, Feb. 2010, pp. 643-650.

* cited by examiner

8-(PIPERAZIN-1-YL)-1,2,3,4-TETRAHYDRO-ISOQUINOLINE DERIVATIVES

CROSS REFERENCE TO RELATED APPLICATION

This application is a 35 U.S.C. § 371 National Phase of PCT Application No. PCT/IB2015/052098 filed Mar. 23, 2015, which claims priority to PCT/IB2014/060092 filed Mar. 24, 2014. The disclosure of these prior applications are hereby incorporated in their entirety by reference.

The present invention relates to novel 8-(piperazin-1-yl)-1,2,3,4-tetrahydro-isoquinoline derivatives of Formula (I), and their use as pharmaceuticals. The invention also concerns related aspects including processes for the preparation of the compounds, pharmaceutical compositions containing one or more compounds of Formula (I), and especially their use as CXCR3 receptor modulators.

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

The chemokine receptor CXCR3 is a G-protein coupled receptor binding to the inflammatory chemokines CXCL9 (initially called MIG, monokine induced by interferon-γ [INF-γ]), CXCL10 (IP-10, INF-γ-inducible protein 10), and CXCL11 (I-TAC, INF-γ-inducible T cell α chemo-attractant). CXCR3 is mainly expressed on activated T helper type 1 (Th1) lymphocytes, but is also present on natural killer cells, macrophages, dendritic cells and a subset of B lymphocytes. The three CXCR3 ligands are expressed mainly under inflammatory conditions, expression in healthy tissue is very low. Cells that can express CXCR3 ligands, for instance after exposure to inflammatory cytokines such as interferon-γ or TNF-α, include diverse stromal cells such as endothelial cells, fibroblasts, epithelial cells, keratinocytes but also includes hematopoietic cells such as macrophages and monocytes. The interaction of CXCR3 and its ligands (henceforth referred to as the CXCR3 axis) is involved in guiding receptor bearing cells to specific locations in the body, particularly to sites of inflammation, immune injury and immune dysfunction and is also associated with tissue damage, the induction of apoptosis, cell growth, and angiostasis. CXCR3 and its ligands are upregulated and highly expressed in diverse pathological situations including autoimmune disorders, inflammation, infection, transplant rejection, fibrosis, neurodegeneration and cancer.

A role of the CXCR3 axis in autoimmune disorders is corroborated by several preclinical and clinical observations. Autoimmune disorders in which histological analysis of inflammatory lesions or serum levels of patients revealed elevated levels of CXCR3 ligands or increased numbers of CXCR3 positive cells include rheumatoid arthritis (RA), systemic lupus erythematosus (SLE), lupus nephritis, multiple sclerosis (MS), inflammatory bowel disease (IBD; comprising Crohn's disease and ulcerative colitis), and type I diabetes mellitus (Groom, J. R. & Luster, A. D. Immunol Cell Biol 2011, 89, 207; Groom, J. R. & Luster, A. D. Exp Cell Res 2011, 317, 620; Lacotte, S., Brun, S., Muller, S. & Dumortier, H. Ann N Y Acad Sci 2009, 1173, 310). As expression of CXCR3 ligands is very low in healthy tissue, the above cited correlative evidence strongly suggest a role for CXCR3 in human autoimmune diseases.

Preclinical disease models performed with CXCR3 deficient mice, mice deficient for one of the CXCR3 ligands or the use of antibodies blocking the function of either CXCR3 or one of its ligands further corroborate a role for the CXCR3 axis in immune pathology. For instance, it has been shown that mice deficient for either CXCR3 or the CXCR3 ligand CXCL9 show reduced pathology in a model for lupus nephritis (Menke, J. et al. J Am Soc Nephrol 2008, 19, 1177). In an animal model for another form of kidney inflammation, interstitial cystitis, administration of an antibody blocking CXCL10 function was shown to reduce pathology in cyclophosphamide-induced cystitis (Sakthivel, S. K. et al. J Immune Based Ther Vaccines 2008, 6, 6). Similarly, blocking CXCL10 with an antibody reduced pathology in a rat model of rheumatoid arthritis (Mohan, K. & Issekutz, T. B. J Immunol 2007, 179, 8463). Similarly, in a murine model of inflammatory bowel disease, a blocking antibody against CXCL10 could prevent pathology in a therapeutic setting (Singh, U. P. et al. J Interferon Cytokine Res 2008, 28, 31). Further, experiments performed with tissue from CXCR3 deficient mice suggests a role for CXCR3 in celiac disease, another autoimmune type disorder (Lammers, K. M. et al. Gastroenterology 2008, 135, 194).

Inflammatory diseases that are associated with an elevated expression of the CXCR3 axis include chronic obstructive pulmonary disorder (COPD), asthma, sarcoidosis, atherosclerosis and myocarditis (Groom, J. R. & Luster, A. D. Immunol Cell Biol 2011, 89, 207; Groom, J. R. & Luster, A. D. Exp Cell Res 2011, 317, 620).

One study has shown that CXCR3 positive cells are increased in the lungs of smokers with COPD compared to healthy subjects and immunoreactivity for the CXCR3-ligand CXCL10 was present in the bronchiolar epithelium of smokers with COPD but not in the bronchiolar epithelium of smoking and nonsmoking control subjects (Saetta, M. et al. Am J Respir Crit Care Med 2002, 165, 1404). These findings suggest that the CXCR3 axis may be involved in the immune cell recruitment that occurs in peripheral airways of smokers with COPD. In agreement with these observations, a preclinical study of COPD revealed an attenuation of acute lung inflammation induced by cigarette smoke in CXCR3 deficient mice (Nie, L. et al. Respir Res 2008, 9, 82).

In one investigation of atherosclerosis, CXCR3 expression was found on all T cells within human atherosclerotic lesions. CXCR3 ligands CXCL9, CXCL10 and CXCL11 were all found in endothelial and smooth muscle cells associated with those lesions, suggesting that they are involved in the recruitment and retention of CXCR3 positive cells, particularly activated T lymphocytes, observed within vascular wall lesions during atherogenesis (Mach, F. et al. J Clin Invest 1999, 104, 1041).

Preclinical studies further support a role of CXCR3 in the development of atherosclerosis. CXCR3 genetic deletion in mice lacking ApoE results in a significantly reduced atherosclerotic lesion development within abdominal aortas (Veillard, N. R. et al. Circulation 2005, 112, 870).

A pivotal role for the CXCR3 axis has also been suggested in rejection reactions after organ transplantation and bone marrow transplantation related toxicity (Groom, J. R. & Luster, A. D. Exp Cell Res 2011, 317, 620.). Preclinically, CXCR3 deficient mice show a significant resistance to allograft rejection (Hancock, W. W. et al. J Exp Med 2000, 192, 1515).

CXCR3 ligand plasma concentrations also positively correlate with diverse liver pathologies, including liver cirrhosis and fibrosis in humans (Tacke, F., et al. Liver Int 2011, 31, 840).

In the field of oncology, blocking the CXCR3 axis has been proposed to help limit the metastatic spread of cancer cells. For instance, administration of the small molecule CXCR3 receptor antagonist AMG487 could limit the metastasis of tumor cells to the lungs (Pradelli, E. et al. Int J Cancer 2009, 125, 2586). Functional evidence for a role of CXCR3 in regulating B-cell chronic lymphocytic leukemia (CLL) was reported by Trentin and coworkers (Trentin, L. et al. J Clin Invest 1999, 104, 115).

In the central nervous system, blocking the CXCR3 axis may have beneficial effects and prevent neurodegeneration. Increased expression of CXCL10 in the CNS has been demonstrated in ischemia, Alzheimer's disease, multiple sclerosis (MS), and human immunodeficiency virus (HIV)-encephalitis. For example, ex vivo experiments have shown that tissue derived from either CXCR3 or CXCL10 deficient mice, neuronal cell death was diminished after neurotoxic NMDA-treatment when compared to tissue derived from wild type mice (van Weering, H. R. et al. Hippocampus 2011, 21, 220). In a study looking to indentify drug-like molecules that provide neuroprotection against HTT fragment-induced neurodegeneration in a model for Huntington's disease, two CXCR3 receptor antagonists were identified (Reinhart, P. H. et al. Neurobiol Dis 2011, 43, 248.)

1-(Piperazin-1-yl)-2-heteroaryl-ethanone derivatives have been disclosed in WO 2007/100610, WO 2010/126811, WO 2010/126851, WO 2013/114332, WO 2015/011099 and on a poster presentation (A. Prokopowicz et al., *Optimization of a biaryl series of CXCR3 antagonists*, 244th ACS National Meeting, Philadelphia, US, Aug. 19-23, 2012).

It has now been found that 8-(piperazin-1-yl)-1,2,3,4-tetrahydro-isoquinoline derivatives of Formula (I) are potent CXCR3 modulators which may be useful for the treatment of diseases that are mediated or sustained through the CXCR3 axis, including autoimmune disorders (e.g. rheumatoid arthritis, multiple sclerosis, inflammatory bowel disease, systemic lupus erythematosus, lupus nephritis, interstitial cystitis, celiac disease), inflammatory disorders (e.g. asthma, COPD, atherosclerosis, myocarditis, sarcoidosis), transplantation rejection, fibrosis (e.g. liver cirrhosis), neurodegeneration and conditions involving neuronal death (e.g. Alzheimer's disease, Huntington's disease), and cancer.

1) In a first embodiment, the present invention relates to compounds of Formula (I)

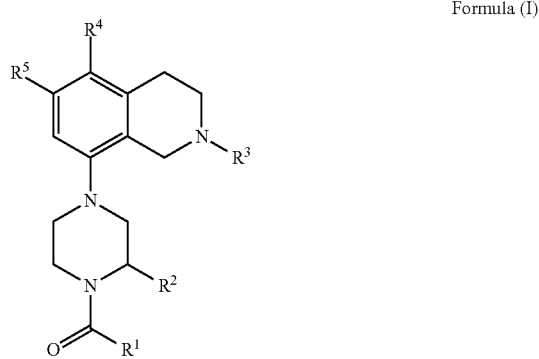

Formula (I)

wherein $R^1$ represents heteroaryl-$(C_{1-2})$alkyl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono- or di-substituted with $(C_{1-4})$alkyl; or heterocyclyl-$(C_{1-2})$alkyl, wherein the heterocyclyl is a 5- or 6-membered monocyclic non-aromatic ring containing one or two nitrogen atoms which is annulated to a phenyl or pyridinyl ring, and wherein the heterocyclyl is unsubstituted or mono- or di-substituted wherein the substituents are independently selected from the group consisting of $(C_{1-4})$alkyl and oxo;

$R^2$ represents hydrogen or methyl;

$R^3$ represents aryl, wherein the aryl is a phenyl- or naphthyl-group, which groups are independently unsubstituted or mono- or di-substituted wherein the substituents are independently selected from the group consisting of halogen, $(C_{1-4})$alkyl, $(C_{1-4})$alkoxy, $(C_{1-2})$fluoroalkyl, $(C_{1-2})$fluoroalkoxy and cyano; aryl-$(C_{1-2})$alkyl, wherein the aryl is a phenyl- or naphthyl-group, which groups are independently unsubstituted or mono-substituted with halogen; heteroaryl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono- or di-substituted wherein the substituents are independently selected from the group consisting of halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy, di-$(C_{1-2})$alkyl-amino, hydroxy, cyano, phenyl, pyridinyl and heteroaryl-$(C_{1-2})$alkyl, wherein the heteroaryl is a 5- or 6-membered monocyclic aromatic ring containing 1 or 2 heteroatoms independently selected from oxygen, nitrogen and sulphur; aryl-$(C_{1-2})$alkyl-sulfonyl, wherein the aryl is a phenyl- or naphthyl-group; or $R^6$-carbonyl;

$R^4$ represents hydrogen, halogen, $(C_{1-2})$fluoroalkyl or cyano;

$R^5$ represents hydrogen, halogen or $(C_{1-2})$fluoroalkyl; and $R^6$ represents $(C_{1-4})$alkyl; $(C_{3-6})$cycloalkyl, wherein the cycloalkyl is unsubstituted or mono-substituted with phenyl; $(C_{5-6})$cycloalkyl, wherein the cycloalkyl is annulated to a phenyl ring; $(C_{1-2})$alkoxy-$(C_{1-2})$alkyl; aryl, wherein the aryl is a phenyl- or naphthyl-group, which groups are independently unsubstituted or mono- or di-substituted wherein the substituents are independently selected from the group consisting of halogen, $(C_{1-4})$alkyl, $(C_{1-4})$alkoxy, $(C_{1-2})$fluoroalkyl and di-$(C_{1-2})$alkyl-amino; aryl-$(C_{1-2})$alkyl, wherein the aryl is a phenyl- or naphthyl-group, which groups are independently unsubstituted or mono- or di-substituted wherein the substituents are independently selected from the group consisting of halogen and $(C_{1-4})$alkoxy; aryloxy-$(C_{1-2})$alkyl, wherein the aryl is a phenyl- or naphthyl-group; aryl-$(C_{1-2})$alkoxy, wherein the aryl is a phenyl- or naphthyl-group; heterocyclyl-$(C_{1-2})$alkyl, wherein the heterocyclyl is a 5- or 6-membered monocyclic non-aromatic ring containing one or two heteroatoms independently selected from oxygen and nitrogen; heteroaryl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono-substituted with $(C_{1-4})$alkyl; or heteroaryl-$(C_{1-2})$alkyl, wherein the heteroaryl is a 5- to 10-membered monocyclic or bicyclic aromatic ring containing 1, 2 or 3 heteroatoms independently selected from oxygen, nitrogen and sulphur; and to the salts (in particular pharmaceutically acceptable salts) of such compounds.

Definitions provided herein are intended to apply uniformly to the compounds of Formulae (I) and $(I_{Ar})$ as defined in any one of embodiments 1) to 31), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The compounds of Formula (I) as defined in any one of embodiments 1) to 31), may contain one or more stereogenic or asymmetric centers, such as one or more asymmetric carbon atoms. The compounds of Formula (I) may thus be present as mixtures of stereoisomers or in stereoisomerically enriched form, preferably as pure stereoisomers. Mixtures of stereoisomers may be separated in a manner known to a person skilled in the art.

The term "enriched", for example when used in the context of enantiomers, is understood in the context of the present invention to mean especially that the respective enantiomer is present in a ratio (mutatis mutandis: purity) of at least 70:30, and notably of at least 90:10 (mutatis mutandis: purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

The term "halogen" means fluorine, chlorine, bromine or iodine. In case a "halogen" is a substituent to an "aryl group" representing "$R^3$", the term "halogen" means preferably fluorine or chlorine. In case a "halogen" is a substituent to an "aryl group" of an "aryl-($C_{1-2}$)alkyl group" representing "$R^3$", the term "halogen" means preferably chlorine. In case a "halogen" is a substituent to a "heteroaryl group" representing "$R^3$", the term "halogen" means preferably fluorine, chlorine or bromine, and more preferably fluorine or chlorine. In case $R^4$ represents "halogen" the term means preferably fluorine, chlorine or bromine, and more preferably fluorine. In case $R^5$ represents "halogen" the term means preferably fluorine. In case a "halogen" is a substituent to an "aryl group" representing "$R^6$", the term "halogen" means preferably fluorine or chlorine, and more preferably chlorine. In case a "halogen" is a substituent to an "aryl group" of an "aryl-($C_{1-2}$)alkyl group" representing "$R^6$", the term "halogen" means preferably chlorine.

The term "alkyl", used alone or in combination, refers to a straight or branched saturated hydrocarbon chain containing one to four carbon atoms. The term "($C_{x-y}$)alkyl" (x and y each being an integer), refers to an alkyl group as defined before containing x to y carbon atoms. For example a ($C_{1-4}$)alkyl group contains from one to four carbon atoms. Examples of ($C_{1-4}$)alkyl groups are methyl, ethyl, n-propyl, iso-propyl, n-butyl, iso-butyl, sec.-butyl and tert.-butyl. Examples of ($C_{1-3}$)alkyl groups are methyl, ethyl, n-propyl and iso-propyl. Examples of ($C_{1-2}$)alkyl groups are methyl and ethyl. In case a "($C_{x-y}$)alkyl" group is a substituent to a "heteroaryl group" of a "heteroaryl-($C_{1-2}$)alkyl group" representing "$R^1$", the term "($C_{x-y}$)alkyl" means preferably methyl or ethyl and more preferably methyl. In case a "($C_{x-y}$)alkyl" group is a substituent to a "heterocyclyl group" of a "heterocyclyl-($C_{1-2}$)alkyl group" representing "$R^1$", the term "($C_{x-y}$)alkyl" means preferably methyl or ethyl and more preferably methyl. In case a "($C_{x-y}$)alkyl" group is a substituent to an "aryl group" representing "$R^3$", the term "($C_{x-y}$)alkyl" means preferably methyl. In case a "($C_{x-y}$)alkyl" group is a substituent to a "heteroaryl group" representing "$R^3$", the term "($C_{x-y}$)alkyl" means preferably methyl, ethyl, n-propyl and tert.-butyl and more preferably methyl, ethyl and n-propyl. In case $R^6$ represents "($C_{x-y}$)alkyl" the term means preferably n-propyl, iso-propyl, n-butyl, iso-butyl, sec.-butyl and tert.-butyl, and more preferably iso-propyl. In case a "($C_{x-y}$)alkyl" group is a substituent to an "aryl group" representing "$R^6$", the term "($C_{x-y}$)alkyl" means preferably methyl. In case a "($C_{x-y}$)alkyl" group is a substituent to a "heteroaryl group" representing "$R^6$", the term "($C_{x-y}$)alkyl" means preferably methyl.

The term "alkoxy", used alone or in combination, refers to an alkyl-O— group wherein the alkyl group is as defined before. The term "($C_{x-y}$)alkoxy" (x and y each being an integer) refers to an alkoxy group as defined before containing x to y carbon atoms. For example a ($C_{1-4}$)alkoxy group means a group of the formula ($C_{1-4}$)alkyl-O— in which the term "($C_{1-4}$)alkyl" has the previously given significance. Examples of ($C_{1-4}$)alkoxy groups are methoxy, ethoxy, n-propoxy, iso-propoxy, n-butoxy, iso-butoxy, sec.-butoxy and tert.-butoxy. Examples of ($C_{1-2}$)alkoxy groups are methoxy and ethoxy. In case a "($C_{x-y}$)alkoxy" group is a substituent to an "aryl group" representing "$R^3$", the term "($C_{x-y}$)alkoxy" means preferably methoxy. In case a "($C_{x-y}$)alkoxy" group is a substituent to a "heteroaryl group" representing "$R^3$", the term "($C_{x-y}$)alkoxy" means preferably methoxy, ethoxy and iso-propoxy. In case a "($C_{x-y}$)alkoxy" group is a substituent to an "aryl group" representing "$R^6$", the term "($C_{x-y}$)alkoxy" means preferably methoxy. In case a "($C_{x-y}$)alkoxy" group is a substituent to an "aryl group" of an "aryl-($C_{1-2}$)alkyl group" representing "$R^6$", the term "($C_{x-y}$)alkoxy" means preferably methoxy. The term "($C_{xa-ya}$)alkoxy-($C_{x-y}$)alkyl" (x, xa, y and ya each being an integer) refers to an alkyl group as defined before containing x to y carbon atoms wherein one hydrogen atom has been replaced with ($C_{xa-ya}$)alkoxy as defined before containing xa to ya carbon atoms. For example a "($C_{1-2}$)alkoxy-($C_{1-2}$)alkyl group" refers to an ($C_{1-2}$)alkyl group as defined before containing one or two carbon atoms wherein one hydrogen atom has been replaced with ($C_{1-2}$)alkoxy as defined before containing one or two carbon atoms. Examples of ($C_{1-2}$)alkoxy-($C_{1-2}$)alkyl groups are methoxy-methyl, 1-methoxy-ethyl, 2-methoxy-ethyl, ethoxy-methyl, 1-ethoxy-ethyl and 2-ethoxy-ethyl. In case $R^6$ represents "($C_{1-2}$)alkoxy-($C_{1-2}$)alkyl" the term means preferably methoxy-methyl.

The term "di-($C_{x-y}$)alkyl-amino" (x and y each being an integer) refers to an amino group (—$NH_2$) wherein each hydrogen atom has been independently replaced with ($C_{x-y}$)alkyl as defined before containing x to y carbon atoms. For example a "di-($C_{1-2}$)alkyl-amino group" refers to an amino group (—$NH_2$) wherein each hydrogen atom has been independently replaced with ($C_{1-2}$)alkyl as defined before containing one or two carbon atoms. Examples of di-($C_{1-2}$)alkyl-amino groups are N,N-dimethylamino, N-ethyl-N-methyl-amino and N,N-diethylamino. In case a "di-($C_{x-y}$)alkyl-amino" group is a substituent to a "heteroaryl group" representing "$R^3$", the term "di-($C_{x-y}$)alkyl-amino" means preferably N,N-dimethylamino. In case a "di-($C_{x-y}$)alkyl-amino" group is a substituent to an "aryl group" representing "$R^6$", the term "di-($C_{x-y}$)alkyl-amino" means preferably N,N-dimethylamino.

The term "fluoroalkyl" refers to an alkyl group as defined before containing one or two carbon atoms in which one or more (and possibly all) hydrogen atoms have been replaced with fluorine. The term "($C_{x-y}$)fluoroalkyl" (x and y each being an integer) refers to a fluoroalkyl group as defined before containing x to y carbon atoms. For example a ($C_{1-2}$)fluoroalkyl group contains one or two carbon atoms in which one to five hydrogen atoms have been replaced with fluorine. Representative examples of $(C_{1-2})$fluoroalkyl groups include difluoromethyl, trifluoromethyl, 2-fluoroethyl, 2,2-difluoroethyl, and 2,2,2-trifluoroethyl. Preferred are $(C_1)$fluoroalkyl groups such as trifluoromethyl or difluoromethyl. In case a "$(C_{x-y})$fluoroalkyl" group is a substituent to an "aryl group" representing "$R^3$", the term "$(C_{x-y})$fluoroalkyl" means preferably trifluoromethyl. In case a "$(C_{x-y})$fluoroalkyl" group is a substituent to a "heteroaryl group" representing "$R^3$", the term "$(C_{x-y})$fluoroalkyl" means preferably trifluoromethyl. In case $R^4$ represents "$(C_{x-y})$fluoroalkyl" the term means preferably trifluoromethyl. In case $R^5$ represents "$(C_{x-y})$fluoroalkyl" the term means preferably trifluoromethyl. In case a "$(C_{x-y})$fluoroalkyl" group is a substituent to an "aryl group" representing "$R^6$", the term "$(C_{x-y})$fluoroalkyl" means preferably trifluoromethyl.

The term "fluoroalkoxy" refers to an alkoxy group as defined before containing one or two carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-2})$fluoroalkoxy group contains one or two carbon atoms in which one to five hydrogen atoms have been replaced with fluorine. Representative examples of $(C_{1-2})$ fluoroalkoxy groups include trifluoromethoxy, difluoromethoxy and 2,2,2-trifluoroethoxy. In case a "$(C_{x-y})$fluoroalkoxy" group is a substituent to an "aryl group" representing "$R^3$", the term "$(C_{x-y})$fluoroalkoxy" means preferably trifluoromethoxy. In case a "$(C_{x-y})$fluoroalkoxy" group is a substituent to a "heteroaryl group" representing "$R^3$", the term "$(C_{x-y})$fluoroalkoxy" means preferably trifluoromethoxy and 2,2,2-trifluoroethoxy and more preferably 2,2,2-trifluoroethoxy.

The term "oxo" refers to an oxygen atom which is attached to a carbon atom of the remaining part of the molecule via a double bond.

The term "cycloalkyl", used alone or in combination, refers to a saturated carbocyclic ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. A $(C_{3-6})$cycloalkyl group may be unsubstituted or substituted as specifically defined. Examples of $(C_{3-6})$cycloalkyl groups are cyclopropyl, cyclobutyl, cyclopentyl, and cyclohexyl. In case a "$(C_{3-6})$cycloalkyl" group is a substituent to a "heteroaryl group" representing "$R^3$", the term "$(C_{3-6})$cycloalkyl" means preferably cyclopropyl. In case "$R^6$" represents an "unsubstituted $(C_{3-6})$cycloalkyl" group the term means preferably cyclopropyl, cyclobutyl, cyclopentyl and cyclohexyl and more preferably cyclopentyl. In case "$R^6$" represents a "mono-substituted $(C_{3-6})$ cycloalkyl" group the term means preferably mono-substituted cyclopropyl. In case specifically defined, a $(C_{5-6})$ cycloalkyl group may be annulated to a phenyl ring. Examples of annulated $(C_{5-6})$cycloalkyl groups are indanyl and tetrahydronaphthyl. In case "$R^6$" represents "$(C_{5-6})$ cycloalkyl, wherein the cycloalkyl is annulated to a phenyl ring" the term means preferably tetrahydronaphthyl (and notably 1-tetrahydronaphthyl).

The term "aryl", used alone or in combination, refers to an aryl-group as specifically defined which group may be unsubstituted or substituted as specifically defined. Preferred examples of "unsubstituted or substituted aryl-groups" representing "$R^3$" are phenyl, 4-fluoro-phenyl, 4-chloro-phenyl, 2-methoxy-phenyl, 3-methoxy-phenyl, 4-methoxy-phenyl, 4-cyano-phenyl, 4-trifluoromethyl-phenyl and 4-trifluoromethoxy-phenyl; more preferred are phenyl, 4-fluoro-phenyl, 4-chloro-phenyl, 3-methoxy-phenyl, 4-methoxy-phenyl and 4-cyano-phenyl. Preferred examples of "unsubstituted or substituted aryl-groups" representing "$R^6$" are phenyl, 4-chloro-phenyl, 3,4-dichloro-phenyl, 4-methyl-phenyl, 4-methoxy-phenyl, 4-trifluoromethyl-phenyl and 3-dimethylamino-phenyl; more preferred are 4-chloro-phenyl and 3,4-dichloro-phenyl.

The term "aryl-$(C_{x-y})$alkyl" refers to an alkyl group as defined before containing x to y carbon atoms wherein one hydrogen atom has been replaced with unsubstituted or substituted aryl as specifically defined. For example an "aryl-$(C_{1-2})$alkyl group" refers to an $(C_{1-2})$alkyl group as defined before containing one or two carbon atoms wherein one hydrogen atom has been replaced with unsubstituted or substituted aryl as specifically defined. Examples are aryl-methyl, 1-aryl-ethyl and 2-aryl-ethyl, wherein aryl refers to an aryl-group as specifically defined which group may be unsubstituted or substituted as specifically defined. A preferred example of "aryl-$(C_{1-2})$alkyl" representing "$R^3$" is (4-chloro-phenyl)-methyl. Preferred examples of "aryl-$(C_{1-2})$alkyl" representing "$R^6$" are phenyl-methyl, 1-phenyl-ethyl, 2-phenyl-ethyl, 2-(4-chloro-phenyl)-ethyl, 2-(3,4-dichloro-phenyl)-ethyl and 2-(4-methoxy-phenyl)-ethyl.

The term "aryl-$(C_{x-y})$alkoxy" refers to an alkoxy group as defined before containing x to y carbon atoms wherein one hydrogen atom has been replaced with unsubstituted or substituted aryl as specifically defined. For example an "aryl-$(C_{1-2})$alkoxy group" refers to an $(C_{1-2})$alkoxy group as defined before containing one or two carbon atoms wherein one hydrogen atom has been replaced with unsubstituted or substituted aryl as specifically defined. Examples are aryl-methoxy, 1-aryl-ethoxy and 2-aryl-ethoxy, wherein aryl refers to an aryl-group as specifically defined which group may be unsubstituted or substituted as specifically defined. A preferred example of "aryl-$(C_{1-2})$alkoxy" representing "$R^6$" is benzyloxy.

The term "aryloxy-$(C_{x-y})$alkyl" refers to an alkyl group as defined before containing x to y carbon atoms wherein one hydrogen atom has been replaced with unsubstituted or substituted aryloxy as specifically defined, wherein aryloxy refers to an "aryl-O—" group. For example an "aryloxy-$(C_{1-2})$alkyl group" refers to an $(C_{1-2})$alkyl group as defined before containing one or two carbon atoms wherein one hydrogen atom has been replaced with unsubstituted or substituted aryloxy as specifically defined. Examples are aryloxy-methyl, 1-aryloxy-ethyl and 2-aryloxy-ethyl, wherein aryloxy refers to an "aryl-O—" group as specifically defined which group may be unsubstituted or substituted as specifically defined. A preferred example of "aryloxy-$(C_{1-2})$alkyl" representing "$R^6$" is phenyloxy-methyl.

The term "aryl-$(C_{x-y})$alkyl-sulfonyl" refers to an aryl-$(C_{x-y})$alkyl group as defined before which is attached to the rest of the molecule via a sulfonyl-group. For example an "aryl-$(C_{1-2})$alkyl-sulfonyl group" refers to an aryl-$(C_{1-2})$ alkyl group as defined before which is attached to the rest of the molecule via a sulfonyl-group. Examples are aryl-methylsulfonyl, 1-aryl-ethylsulfonyl and 2-aryl-ethylsulfonyl, wherein aryl refers to an aryl-group as specifically defined which group may be unsubstituted or substituted as specifically defined. A preferred example of "aryl-$(C_{1-2})$alkyl-sulfonyl" representing "$R^3$" is phenyl-methylsulfonyl (benzylsulfonyl).

The term "heteroaryl", used alone or in combination, refers to a heteroaryl-group as specifically defined which group may be unsubstituted or substituted as specifically defined. Examples of "heteroaryl groups, wherein the heteroaryl is a 5- to 10-membered monocyclic or bicyclic aromatic ring containing 1, 2 or 3 heteroatoms independently selected from oxygen, nitrogen and sulphur" are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, triazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, and imidazopyridinyl. In case of an heteroaryl group having a more restricted definition, the list of examples may be construed from the aforementioned list by taking the respective restrictions into account. For instance, examples of "heteroaryl groups, wherein the heteroaryl is a 5- or 6-membered monocyclic aromatic ring containing 1 or 2 heteroatoms independently selected from oxygen, nitrogen and sulphur" are furanyl, oxazolyl, isoxazolyl, thiophenyl, thiazolyl, isothiazolyl, pyrrolyl, imidazolyl, pyrazolyl, pyridinyl, pyrimidinyl, pyridazinyl, and pyrazinyl. Preferred examples of "heteroaryl-groups" representing "$R^3$" are oxazolyl (notably oxazol-2-yl), thiazolyl (notably thiazol-2-yl), pyridinyl (notably pyridin-2-yl and pyridin-3-yl), pyrimidinyl (notably pyrimidin-2-yl, pyrimidin-4-yl, and pyrimidin-5-yl), pyridazinyl (notably pyridazin-3-yl), pyrazinyl (notably pyrazin-2-yl), triazinyl (notably triazin-2-yl), benzoxazolyl (notably benzoxazol-2-yl), and benzothiazolyl (notably benzothiazol-2-yl); the heteroaryl group may be unsubstituted or substituted as specifically defined; preferred examples of "unsubstituted or substituted heteroaryl-groups" representing "$R^3$" are 5-phenyl-oxazol-2-yl, thiazol-2-yl, 4-methyl-thiazol-2-yl, 4-ethyl-thiazol-2-yl, 4-tert-butyl-thiazol-2-yl, 4-trifluoromethyl-thiazol-2-yl, 4-cyano-thiazol-2-yl, 4-phenyl-thiazol-2-yl, 4-(pyridin-2-yl)-thiazol-2-yl, 5-chloro-thiazol-2-yl, 5-cyano-thiazol-2-yl, 5-phenyl-thiazol-2-yl, 5-(pyrazol-1-ylmethyl)-thiazol-2-yl, 4,5-dimethyl-thiazol-2-yl, pyridin-2-yl, 5-fluoro-pyridin-2-yl, 5-methyl-pyridin-2-yl, 5-trifluoromethyl-pyridin-2-yl, 6-methyl-pyridin-3-yl, 6-trifluoromethyl-pyridin-3-yl, pyrimidin-2-yl, 5-bromo-pyrimidin-2-yl, 5-methyl-pyrimidin-2-yl, 2-methoxy-pyrimidin-4-yl, pyrimidin-5-yl, 2-methyl-pyrimidin-5-yl, 2-ethyl-pyrimidin-5-yl, 2-propyl-pyrimidin-5-yl, 2-cyclopropyl-pyrimidin-5-yl, 2-methoxy-pyrimidin-5-yl, 2-ethoxy-pyrimidin-5-yl, 2-iso-propoxy-pyrimidin-5-yl, 2-trifluoromethyl-pyrimidin-5-yl, 2-(2,2,2-trifluoroethoxy)-pyrimidin-5-yl, 2-dimethylamino-pyrimidin-5-yl, 6-methoxy-pyridazin-3-yl, 6-methoxy-pyrazin-2-yl, 4,6-dimethoxy-triazin-2-yl, benzoxazol-2-yl, benzothiazol-2-yl, 6-fluoro-benzothiazol-2-yl, 6-methyl-benzothiazol-2-yl, and 6-cyano-benzothiazol-2-yl. Preferred examples of "heteroaryl-groups" representing "$R^6$" are oxazolyl (notably oxazol-4-yl), pyrazolyl (notably pyrazol-5-yl), and quinolinyl (notably quinolin-6-yl); the heteroaryl group may be unsubstituted or substituted as specifically defined; preferred examples of "unsubstituted or substituted heteroaryl-groups" representing "$R^6$" are oxazol-4-yl, 1-methyl-pyrazol-5-yl, and quinolin-6-yl.

The term "heteroaryl-$(C_{x-y})$alkyl" refers to an alkyl group as defined before containing x to y carbon atoms wherein one hydrogen atom has been replaced with unsubstituted or substituted heteroaryl as specifically defined. For example a "heteroaryl-$(C_{1-2})$alkyl group" refers to an $(C_{1-2})$alkyl group as defined before containing one or two carbon atoms wherein one hydrogen atom has been replaced with unsubstituted or substituted heteroaryl as specifically defined. Examples are heteroaryl-methyl, 1-heteroaryl-ethyl and 2-heteroaryl-ethyl, wherein heteroaryl refers to an heteroaryl-group as specifically defined which group may be unsubstituted or substituted as specifically defined. Preferred examples of "heteroaryl-$(C_{1-2})$alkyl" representing "$R^1$" are pyrazolyl-methyl (notably pyrazol-1-yl-methyl), pyrazolyl-ethyl (notably 2-(pyrazol-1-yl)-ethyl), triazolyl-methyl (notably 2H-1,2,3-triazol-2-yl-methyl and 1H-1,2,4-triazol-1-yl-methyl), pyrrolo[2,3-b]pyridinyl-methyl (notably 1H-pyrrolo[2,3-b]pyridin-1-yl-methyl), pyrazolo[3,4-b]pyridinyl-methyl (notably 1H-pyrazolo[3,4-b]pyridin-1-yl-methyl and −2H-pyrazolo[3,4-b]pyridin-2-yl-methyl), and imidazo[4,5-b]pyridinyl-methyl (notably 3H-imidazo[4,5-b]pyridin-3-yl-methyl); the heteroaryl group of a "heteroaryl-$(C_{1-2})$alkyl group" representing "$R^1$" may be unsubstituted or substituted as specifically defined; preferred examples of such unsubstituted or substituted groups are 1H-pyrazol-1-yl-methyl, (3-methyl-1H-pyrazol-1-yl)-methyl, (5-methyl-1H-pyrazol-1-yl)-methyl, (3,5-dimethyl-1H-pyrazol-1-yl)-methyl, 2-(1H-pyrazol-1-yl)-ethyl, 2H-1,2,3-triazol-2-yl-methyl, (3,5-dimethyl-1H-1,2,4-triazol-1-yl)-methyl, 1H-pyrrolo[2,3-b]pyridin-1-yl-methyl, 1H-pyrazolo[3,4-b]pyridin-1-yl-methyl, 2H-pyrazolo[3,4-b]pyridin-2-yl-methyl, and 3H-imidazo[4,5-b]pyridin-3-yl-methyl. A preferred example of "heteroaryl-$(C_{1-2})$alkyl", if being a substituent to a heteroaryl group representing "$R^3$", is pyrazolyl-methyl (notably 1H-pyrazol-1-yl-methyl). Preferred examples of "heteroaryl-$(C_{1-2})$alkyl" representing "$R^6$" are pyrazolyl-methyl (notably 1H-pyrazol-1-yl-methyl), pyridinyl-methyl (notably pyridin-3-yl-methyl), indolyl-methyl (notably 1H-indol-1-yl-methyl), and benzimidazolyl-methyl (notably 1H-benzimidazol-1-yl-methyl).

The term "heterocyclyl-$(C_{x-y})$alkyl" refers to an alkyl group as defined before containing x to y carbon atoms wherein one hydrogen atom has been replaced with unsubstituted or substituted heterocyclyl as specifically defined. For example a "heterocyclyl-$(C_{1-2})$alkyl group" refers to an $(C_{1-2})$alkyl group as defined before containing one or two carbon atoms wherein one hydrogen atom has been replaced with unsubstituted or substituted heterocyclyl as specifically defined. Examples are heterocyclyl-methyl, 1-heterocyclyl-ethyl and 2-heterocyclyl-ethyl, wherein heterocyclyl refers to an heterocyclyl-group as specifically defined which group may be unsubstituted or substituted as specifically defined. Examples of "heterocyclyl groups" as used in "heterocyclyl-$(C_{1-2})$alkyl" representing "$R^1$" are pyrrolidinyl, imidazolidinyl, piperidinyl, hexahydropyrimidinyl, and piperazinyl which are independently annulated to a phenyl or pyridinyl ring. Preferred examples of "heterocyclyl-$(C_{1-2})$alkyl" representing "$R^1$" are indolin-1-yl-methyl, 2,3-dihydro-1H-pyrrolo[2,3-b]pyridin-1-yl-methyl, and 2,3-dihydro-1H-benzo[d]imidazol-1-yl-methyl; the heterocyclyl group of a "heterocyclyl-$(C_{1-2})$alkyl group" representing "$R^1$" may be unsubstituted or substituted as specifically defined; preferred examples of such unsubstituted or substituted groups are 2-oxo-indolin-1-yl-methyl, 2,3-dihydro-1H-pyrrolo[2,3-b]pyridin-1-yl-methyl, and 3-methyl-2-oxo-2,3-dihydro-1H-benzo[d]imidazol-1-yl-methyl. Examples of "heterocyclyl groups" as used in "heterocyclyl-$(C_{1-2})$alkyl" representing "$R^6$" are pyrrolidinyl, tetrahydrofuranyl, piperidinyl, piperazinyl, tetrahydropyranyl, morpholinyl, and dioxanyl. A preferred example of "heterocyclyl-$(C_{1-2})$alkyl" representing "$R^6$" is morpholin-4-yl-methyl.

2) A further embodiment of the invention relates to compounds of formula (I) according to embodiment 1), wherein $R^1$ represents heteroaryl-methyl, wherein the heteroaryl is a 5- to 10-membered monocyclic or bicyclic aromatic ring containing 1, 2 or 3 nitrogen atoms, and wherein the heteroaryl is unsubstituted or mono- or di-substituted with $(C_{1-4})$alkyl; or heterocyclyl-methyl, wherein the heterocyclyl is a 5- or 6-membered monocyclic non-aromatic ring containing one or two nitrogen atoms which is annulated to a phenyl or pyridinyl ring, and wherein the heterocyclyl is unsubstituted or mono- or di-substituted wherein the substituents are independently selected from the group consisting of $(C_{1-4})$alkyl and oxo;

$R^2$ represents hydrogen or methyl;

$R^3$ represents aryl, wherein the aryl is a phenyl- or naphthyl-group, which groups are independently unsubstituted or mono- or di-substituted wherein the substituents are independently selected from the group consisting of halogen, $(C_{1-4})$alkoxy, $(C_{1-2})$fluoroalkyl, $(C_{1-2})$fluoroalkoxy and cyano; or heteroaryl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono- or di-substituted wherein the substituents are independently selected from the group consisting of halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy, di-$(C_{1-2})$alkyl-amino, cyano, phenyl, pyridinyl and 1H-pyrazol-1-yl-methyl;

$R^4$ represents hydrogen, halogen, $(C_{1-2})$fluoroalkyl or cyano; and $R^5$ represents hydrogen or halogen;

and to the salts (in particular pharmaceutically acceptable salts) of such compounds.

3) A further embodiment of the invention relates to compounds of formula (I) according to embodiment 1), wherein $R^1$ represents heteroaryl-methyl, wherein the heteroaryl is a 5- to 10-membered monocyclic or bicyclic aromatic ring containing 2 or 3 nitrogen atoms, and wherein the heteroaryl is unsubstituted or mono- or di-substituted with methyl; or heterocyclyl-methyl selected from 2-oxo-indolin-1-yl-methyl, 2,3-dihydro-1H-pyrrolo[2,3-b]pyridin-1-yl-methyl, and 3-methyl-2-oxo-2,3-dihydro-1H-benzo[d]imidazol-1-yl-methyl;

$R^2$ represents hydrogen or methyl;

$R^3$ represents phenyl which is unsubstituted or mono-substituted with fluoro, chloro, methoxy, trifluoromethyl, trifluoromethoxy or cyano; or heteroaryl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono- or di-substituted wherein the substituents are independently selected from the group consisting of fluoro, chloro, bromo, methyl, ethyl, n-propyl, tert.-butyl, cyclopropyl, methoxy, ethoxy, iso-propoxy, trifluoromethyl, 2,2,2-trifluoroethoxy, dimethyl-amino, cyano, phenyl, pyridinyl and 1H-pyrazol-1-yl-methyl;

$R^4$ represents hydrogen, fluoro, trifluoromethyl or cyano; and $R^5$ represents hydrogen or fluoro;

and to the salts (in particular pharmaceutically acceptable salts) of such compounds.

4) A further embodiment of the invention relates to compounds of formula (I) according to embodiment 1), wherein $R^1$ represents heteroaryl-methyl, wherein the heteroaryl is a 5- to 10-membered monocyclic or bicyclic aromatic ring containing 2 or 3 nitrogen atoms, and wherein the heteroaryl is unsubstituted or mono- or di-substituted with $(C_{1-4})$alkyl;

$R^2$ represents hydrogen or methyl;

$R^3$ represents phenyl which is unsubstituted or mono-substituted with halogen, $(C_{1-4})$alkoxy, $(C_{1-2})$fluoroalkyl, $(C_{1-2})$fluoroalkoxy or cyano; or heteroaryl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono- or di-substituted wherein the substituents are independently selected from the group consisting of halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy, di-$(C_{1-2})$alkyl-amino, cyano, phenyl, pyridinyl and 1H-pyrazol-1-yl-methyl;

$R^4$ represents hydrogen, halogen or $(C_{1-2})$fluoroalkyl; and $R^5$ represents hydrogen or halogen;

and to the salts (in particular pharmaceutically acceptable salts) of such compounds.

5) A further embodiment of the invention relates to compounds of formula (I) according to embodiment 1), wherein $R^1$ represents heteroaryl-methyl, wherein the heteroaryl is a 5- to 10-membered monocyclic or bicyclic aromatic ring containing 2 or 3 nitrogen atoms, and wherein the heteroaryl is unsubstituted or mono- or di-substituted with methyl;

$R^2$ represents hydrogen or methyl;

$R^3$ represents phenyl which is unsubstituted or mono-substituted with fluoro, chloro, methoxy, trifluoromethyl, trifluoromethoxy or cyano; or heteroaryl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono-substituted with fluoro, chloro, methyl, ethyl, n-propyl, cyclopropyl, methoxy, ethoxy, iso-propoxy, trifluoromethyl, 2,2,2-trifluoroethoxy or dimethyl-amino;

$R^4$ represents hydrogen, fluoro or trifluoromethyl; and $R^5$ represents hydrogen or fluoro;

and to the salts (in particular pharmaceutically acceptable salts) of such compounds.

6) A further embodiment of the invention relates to compounds of formula (I) according to any one of embodiments 1) or 2), wherein $R^1$ represents heteroaryl-methyl, wherein the heteroaryl is a 5- to 10-membered monocyclic or bicyclic aromatic ring containing 1, 2 or 3 nitrogen atoms, and wherein the heteroaryl is unsubstituted or mono- or di-substituted with $(C_{1-4})$alkyl;

and to the salts (in particular pharmaceutically acceptable salts) of such compounds.

7) A further embodiment of the invention relates to compounds of formula (I) according to any one of embodiments 1) to 5), wherein $R^1$ represents heteroaryl-methyl, wherein the heteroaryl is selected from pyrazolyl, triazolyl, pyrrolo[2,3-b]pyridinyl, pyrazolo[3,4-b]pyridinyl, and imidazo[4,5-b]pyridinyl, and wherein the heteroaryl is unsubstituted or mono- or di-substituted with methyl;

and to the salts (in particular pharmaceutically acceptable salts) of such compounds.

8) A further embodiment of the invention relates to compounds of formula (I) according to any one of embodiments 1) to 5), wherein $R^1$ represents (3,5-dimethyl-1H-1,2,4-triazol-1-yl)-methyl;

and to the salts (in particular pharmaceutically acceptable salts) of such compounds.

9) A further embodiment of the invention relates to compounds of formula (I) according to any one of embodiments 1) or 2), wherein
R¹ represents heterocyclyl-methyl, wherein the heterocyclyl is a 5- or 6-membered monocyclic non-aromatic ring containing one or two nitrogen atoms which is annulated to a phenyl or pyridinyl ring, and wherein the heterocyclyl is unsubstituted or mono- or di-substituted wherein the substituents are independently selected from the group consisting of $(C_{1-4})$alkyl and oxo;
and to the salts (in particular pharmaceutically acceptable salts) of such compounds.

10) A further embodiment of the invention relates to compounds of formula (I) according to any one of embodiments 1), 2) or 6) to 9), wherein
R³ represents phenyl which is unsubstituted or mono-substituted with halogen, $(C_{1-4})$alkoxy, $(C_{1-2})$fluoroalkyl, $(C_{1-2})$fluoroalkoxy or cyano; or heteroaryl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono- or di-substituted wherein the substituents are independently selected from the group consisting of halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy, di-$(C_{1-2})$alkyl-amino, cyano, phenyl, pyridinyl and 1H-pyrazol-1-yl-methyl;
and to the salts (in particular pharmaceutically acceptable salts) of such compounds.

11) A further embodiment of the invention relates to compounds of formula (I) according to any one of embodiments 1), 2), 4) or 6) to 9), wherein
R³ represents phenyl which is unsubstituted or mono-substituted with halogen, $(C_{1-4})$alkoxy, $(C_{1-2})$fluoroalkyl, $(C_{1-2})$fluoroalkoxy or cyano; or heteroaryl, wherein the heteroaryl is selected from pyridinyl and pyrimidinyl, and wherein the heteroaryl is unsubstituted or mono-substituted with halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy or di-$(C_{1-2})$alkyl-amino;
and to the salts (in particular pharmaceutically acceptable salts) of such compounds.

12) A further embodiment of the invention relates to compounds of formula (I) according to any one of embodiments 1), 2), 4) or 6) to 9), wherein
R³ represents phenyl which is unsubstituted or mono-substituted with halogen, $(C_{1-4})$alkoxy, $(C_{1-2})$fluoroalkyl, $(C_{1-2})$fluoroalkoxy or cyano;
and to the salts (in particular pharmaceutically acceptable salts) of such compounds.

13) A further embodiment of the invention relates to compounds of formula (I) according to any one of embodiments 1), 2), 4) or 6) to 9), wherein
R³ represents heteroaryl, wherein the heteroaryl is a 5- to 10-membered monocyclic or bicyclic aromatic ring containing 1, 2 or 3 heteroatoms independently selected from oxygen, nitrogen and sulphur, and wherein the heteroaryl is unsubstituted or mono- or di-substituted wherein the substituents are independently selected from the group consisting of halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy, di-$(C_{1-2})$alkyl-amino, cyano, phenyl, pyridinyl and 1H-pyrazol-1-yl-methyl;
and to the salts (in particular pharmaceutically acceptable salts) of such compounds.

14) A further embodiment of the invention relates to compounds of formula (I) according to any one of embodiments 1) to 9), wherein
R³ represents heteroaryl, wherein the heteroaryl is selected from pyridinyl and pyrimidinyl, and wherein the heteroaryl is unsubstituted or mono-substituted with fluoro, methyl, ethyl, n-propyl, cyclopropyl, methoxy, ethoxy, iso-propoxy, trifluoromethyl, 2,2,2-trifluoroethoxy or dimethyl-amino;
and to the salts (in particular pharmaceutically acceptable salts) of such compounds.

15) A further embodiment of the invention relates to compounds of formula (I) according to any one of embodiments 1) or 6) to 9), wherein
R³ represents R⁶-carbonyl;
and to the salts (in particular pharmaceutically acceptable salts) of such compounds.

16) A further embodiment of the invention relates to compounds of formula (I) according to any one of embodiments 1) to 15), wherein
R⁴ represents hydrogen, fluoro or trifluoromethyl;
and to the salts (in particular pharmaceutically acceptable salts) of such compounds.

17) A further embodiment of the invention relates to compounds of formula (I) according to any one of embodiments 1) to 15), wherein
R⁴ represents fluoro or trifluoromethyl;
and to the salts (in particular pharmaceutically acceptable salts) of such compounds.

18) A further embodiment of the invention relates to compounds of formula (I) according to any one of embodiments 1), 2), 4) or 6) to 17), wherein
R⁵ represents hydrogen or fluoro;
and to the salts (in particular pharmaceutically acceptable salts) of such compounds.

19) A further embodiment of the invention relates to compounds of Formula (I) according to embodiment 1) which are also compounds of Formula $(I_{Ar})$

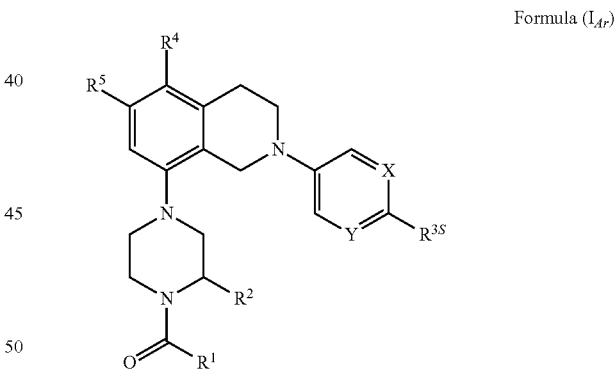

Formula $(I_{Ar})$ wherein
R¹ represents heteroaryl-$(C_{1-2})$alkyl, wherein the heteroaryl is a 5- to 10-membered monocyclic or bicyclic aromatic ring containing 1, 2 or 3 nitrogen atoms, and wherein the heteroaryl is unsubstituted or mono- or di-substituted with $(C_{1-4})$alkyl; or heterocyclyl-$(C_{1-2})$alkyl, wherein the heterocyclyl is a 5- or 6-membered monocyclic non-aromatic ring containing one or two nitrogen atoms which is annulated to a phenyl or pyridinyl ring, and wherein the heterocyclyl is unsubstituted or mono- or di-substituted wherein the substituents are independently selected from the group consisting of $(C_{1-4})$alkyl and oxo;
R² represents hydrogen or methyl;
X and Y represent =CH— and $R^{3S}$ represents hydrogen, halogen, $(C_{1-4})$alkoxy, $(C_{1-2})$fluoroalkyl, $(C_{1-2})$fluoroalkoxy or cyano; or X represents =CH— or =N—, Y represents =N— and $R^{3S}$ represents hydrogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy or di-$(C_{1-2})$alkyl-amino;
$R^4$ represents hydrogen, halogen or $(C_{1-2})$fluoroalkyl; and
$R^5$ represents hydrogen, halogen or $(C_{1-2})$fluoroalkyl;
and to the salts (in particular pharmaceutically acceptable salts) of such compounds.

20) A further embodiment of the invention relates to compounds of formula ($I_{Ar}$) according to embodiment 19), wherein
$R^1$ represents heteroaryl-methyl, wherein the heteroaryl is a 5- to 10-membered monocyclic or bicyclic aromatic ring containing 2 or 3 nitrogen atoms, and wherein the heteroaryl is unsubstituted or mono- or di-substituted with methyl; or heterocyclyl-methyl selected from 2-oxo-indolin-1-yl-methyl and 2,3-dihydro-1H-pyrrolo[2,3-b]pyridin-1-yl-methyl;
$R^2$ represents hydrogen or methyl;
X and Y represent =CH— and $R^{3S}$ represents hydrogen, fluoro, chloro, methoxy, trifluoromethyl, trifluoromethoxy or cyano; or X represents =CH— or =N—, Y represents =N— and $R^{3S}$ represents hydrogen, methyl, ethyl, n-propyl, cyclopropyl, methoxy, ethoxy, iso-propoxy, trifluoromethyl, 2,2,2-trifluoroethoxy or dimethyl-amino;
$R^4$ represents hydrogen, fluoro or trifluoromethyl; and
$R^5$ represents hydrogen or fluoro;
and to the salts (in particular pharmaceutically acceptable salts) of such compounds.

21) A further embodiment of the invention relates to compounds of formula ($I_{Ar}$) according to embodiment 19), wherein
$R^1$ represents heteroaryl-methyl, wherein the heteroaryl is a 5- to 10-membered monocyclic or bicyclic aromatic ring containing 2 or 3 nitrogen atoms, and wherein the heteroaryl is unsubstituted or mono- or di-substituted with methyl;
$R^2$ represents hydrogen or methyl;
X represents =N—;
Y represents =N—;
$R^{3S}$ represents hydrogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy or di-$(C_{1-2})$alkyl-amino;
$R^4$ represents hydrogen, fluoro or trifluoromethyl; and
$R^5$ represents hydrogen or fluoro;
and to the salts (in particular pharmaceutically acceptable salts) of such compounds.

22) A further embodiment of the invention relates to compounds of formula ($I_{Ar}$) according to any one of embodiments 19) to 21), wherein
$R^1$ represents heteroaryl-methyl, wherein the heteroaryl is selected from pyrazolyl, triazolyl, pyrrolo[2,3-b]pyridinyl, pyrazolo[3,4-b]pyridinyl, and imidazo[4,5-b]pyridinyl, and wherein the heteroaryl is unsubstituted or mono- or di-substituted with methyl;
and to the salts (in particular pharmaceutically acceptable salts) of such compounds.

23) A further embodiment of the invention relates to compounds of formula ($I_{Ar}$) according to any one of embodiments 19) to 21), wherein
$R^1$ represents (3,5-dimethyl-1H-1,2,4-triazol-1-yl)-methyl;
and to the salts (in particular pharmaceutically acceptable salts) of such compounds.

24) A further embodiment of the invention relates to compounds of formula ($I_{Ar}$) according to any one of embodiments 19), 20), 22) or 23), wherein
X and Y represent =CH—;
and to the salts (in particular pharmaceutically acceptable salts) of such compounds.

25) A further embodiment of the invention relates to compounds of formula ($I_{Ar}$) according to any one of embodiments 19), 20), 22) or 23), wherein
X represents =CH— and Y represents =N—;
and to the salts (in particular pharmaceutically acceptable salts) of such compounds.

26) A further embodiment of the invention relates to compounds of formula ($I_{Ar}$) according to any one of embodiments 19), 20), 22) or 23), wherein
X represents =N— and Y represents =N—;
and to the salts (in particular pharmaceutically acceptable salts) of such compounds.

27) A further embodiment of the invention relates to compounds of formula ($I_{Ar}$) according to any one of embodiments 25) or 26), wherein
$R^{3S}$ represents $(C_{1-4})$alkyl or $(C_{1-2})$fluoroalkyl;
and to the salts (in particular pharmaceutically acceptable salts) of such compounds.

28) A further embodiment of the invention relates to compounds of formula (I) according to any one of embodiments 1) to 27), wherein the carbon atom of the piperazine ring, which is attached to $R^2$, is achiral in case $R^2$ represents hydrogen and (R)-configurated in case $R^2$ represents methyl;
and to the salts (in particular pharmaceutically acceptable salts) of such compounds.

29) A further embodiment of the invention relates to compounds of formula (I) according to any one of embodiments 1) to 27), wherein the carbon atom of the piperazine ring, which is attached to $R^2$, is achiral in case $R^2$ represents hydrogen and (S)-configurated in case $R^2$ represents methyl;
and to the salts (in particular pharmaceutically acceptable salts) of such compounds.

30) Examples of compounds of formula (I) as defined in embodiment 1) are selected from the group consisting of:
2-(3,5-Dimethyl-pyrazol-1-yl)-1-{(R)-2-methyl-4-[2-(5-pyrazol-1-ylmethyl-thiazol-2-yl)-5-trifluoromethyl-1,2,3,4-tetrahydro-isoquinolin-8-yl]-piperazin-1-yl}-ethanone;
2-(3,5-Dimethyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone;
2-(3,5-Dimethyl-pyrazol-1-yl)-1-{(R)-4-[2-(4-ethyl-thiazol-2-yl)-5-trifluoromethyl-1,2,3,4-tetrahydro-isoquinolin-8-yl]-2-methyl-piperazin-1-yl}-ethanone;
1-{(R)-4-[2-(4-tert-Butyl-thiazol-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;
2-(3,5-Dimethyl-pyrazol-1-yl)-1-{(R)-2-methyl-4-[2-(4-pyridin-2-yl-thiazol-2-yl)-5-trifluoromethyl-1,2,3,4-tetrahydro-isoquinolin-8-yl]-piperazin-1-yl}-ethanone;
1-{(R)-4-[2-(5-Chloro-thiazol-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;
2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-thiazole-4-carbonitrile;
2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-thiazole-5-carbonitrile;
2-(3,5-Dimethyl-pyrazol-1-yl)-1-{(R)-2-methyl-4-[2-(6-methyl-benzothiazol-2-yl)-5-trifluoromethyl-1,2,3,4-tetrahydro-isoquinolin-8-yl]-piperazin-1-yl}-ethanone;
2-(3,5-Dimethyl-pyrazol-1-yl)-1-{(R)-4-[2-(6-fluoro-benzothiazol-2-yl)-5-trifluoromethyl-1,2,3,4-tetrahydro-isoquinolin-8-yl]-2-methyl-piperazin-1-yl}-ethanone;

2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-benzothiazole-6-carbonitrile;

1-[(R)-4-(2-Benzooxazol-2-yl-5-trifluoromethyl-1,2,3,4-tetrahydro-isoquinolin-8-yl)-2-methyl-piperazin-1-yl]-2-(3,5-dimethyl-pyrazol-1-yl)-ethanone;

1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;

1-{(R)-4-[2-(5-Bromo-pyrimidin-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;

1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;

2-Imidazo[4,5-b]pyridin-3-yl-1-[(R)-2-methyl-4-(2-phenyl-5-trifluoromethyl-1,2,3,4-tetrahydro-isoquinolin-8-yl)-piperazin-1-yl]-ethanone;

2-Imidazo[4,5-b]pyridin-3-yl-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone;

2-Imidazo[4,5-b]pyridin-3-yl-1-{(R)-4-[2-(3-methoxy-phenyl)-5-trifluoromethyl-1,2,3,4-tetrahydro-isoquinolin-8-yl]-2-methyl-piperazin-1-yl}-ethanone;

1-{(R)-4-[2-(4,6-Dimethoxy-[1,3,5]triazin-2-yl)-5-trifluoromethyl-1,2,3,4-tetrahydro-isoquinolin-8-yl]-2-methyl-piperazin-1-yl}-2-imidazo[4,5-b]pyridin-3-yl-ethanone;

1-{(R)-4-[2-(2-Ethoxy-pyrimidin-5-yl)-5-trifluoromethyl-1,2,3,4-tetrahydro-isoquinolin-8-yl]-2-methyl-piperazin-1-yl}-2-imidazo[4,5-b]pyridin-3-yl-ethanone;

1-{(R)-4-[2-(4-Chloro-phenyl)-5-trifluoromethyl-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(2-propyl-pyrimidin-5-yl)-5-trifluoromethyl-1,2,3,4-tetrahydro-isoquinolin-8-yl]-piperazin-1-yl}-ethanone;

2-(3,5-Dimethyl-[1,2,4]triazol-1-yl)-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone;

2-(3,5-Dimethyl-pyrazol-1-yl)-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone;

1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-2-pyrazol-1-yl-ethanone;

1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-2-[1,2,3]triazol-2-yl-ethanone;

1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-3-pyrazol-1-yl-propan-1-one;

1-{4-[2-(2-Ethoxy-pyrimidin-5-yl)-5-trifluoromethyl-1,2,3,4-tetrahydro-isoquinolin-8-yl]-piperazin-1-yl}-2-imidazo[4,5-b]pyridin-3-yl-ethanone;

2-(3,5-Dimethyl-pyrazol-1-yl)-1-{4-[2-(2-ethoxy-pyrimidin-5-yl)-5-trifluoromethyl-1,2,3,4-tetrahydro-isoquinolin-8-yl]-piperazin-1-yl}-ethanone;

2-(3,5-Dimethyl-[1,2,4]triazol-1-yl)-1-{4-[2-(2-ethoxy-pyrimidin-5-yl)-5-trifluoromethyl-1,2,3,4-tetrahydro-isoquinolin-8-yl]-piperazin-1-yl}-ethanone;

1-{4-[2-(2-Ethoxy-pyrimidin-5-yl)-5-trifluoromethyl-1,2,3,4-tetrahydro-isoquinolin-8-yl]-piperazin-1-yl}-2-pyrazolo[3,4-b]pyridin-1-yl-ethanone;

1-{4-[2-(2-Ethoxy-pyrimidin-5-yl)-5-trifluoromethyl-1,2,3,4-tetrahydro-isoquinolin-8-yl]-piperazin-1-yl}-2-pyrazolo[3,4-b]pyridin-2-yl-ethanone;

1-(2-{4-[2-(2-Ethoxy-pyrimidin-5-yl)-5-trifluoromethyl-1,2,3,4-tetrahydro-isoquinolin-8-yl]-piperazin-1-yl}-2-oxo-ethyl)-1,3-dihydro-indol-2-one;

1-{(S)-4-[2-(2-Ethoxy-pyrimidin-5-yl)-5-trifluoromethyl-1,2,3,4-tetrahydro-isoquinolin-8-yl]-2-methyl-piperazin-1-yl}-2-imidazo[4,5-b]pyridin-3-yl-ethanone;

2-(3,5-Dimethyl-pyrazol-1-yl)-1-{(S)-4-[2-(2-ethoxy-pyrimidin-5-yl)-5-trifluoromethyl-1,2,3,4-tetrahydro-isoquinolin-8-yl]-2-methyl-piperazin-1-yl}-ethanone;

1-{(S)-4-[2-(2-Ethoxy-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone;

2-(2,3-Dihydro-pyrrolo[2,3-b]pyridin-1-yl)-1-{(S)-4-[2-(2-ethoxy-pyrimidin-5-yl)-5-trifluoromethyl-1,2,3,4-tetrahydro-isoquinolin-8-yl]-2-methyl-piperazin-1-yl}-ethanone;

2-(3,5-Dimethyl-[1,2,4]triazol-1-yl)-1-{(R)-4-[2-(6-fluoro-benzothiazol-2-yl)-5-trifluoromethyl-1,2,3,4-tetrahydro-isoquinolin-8-yl]-2-methyl-piperazin-1-yl}-ethanone;

1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone;

1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-(3-methyl-pyrazol-1-yl)-ethanone;

1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-(5-methyl-pyrazol-1-yl)-ethanone;

2-(3,5-Dimethyl-[1,2,4]triazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone;

1-{(R)-2-Methyl-4-[5-trifluoromethyl-2-(4-trifluoromethyl-thiazol-2-yl)-1,2,3,4-tetrahydro-isoquinolin-8-yl]-piperazin-1-yl}-2-pyrazolo[3,4-b]pyridin-1-yl-ethanone;

2-(3-Methyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone;

2-(5-Methyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone;

1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3,5-dimethyl-[1,2,4]triazol-1-yl)-ethanone;

1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone;

1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone;

1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(5-methyl-pyrazol-1-yl)-ethanone;

1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3,5-dimethyl-[1,2,4]triazol-1-yl)-ethanone;

1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone;

1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(5-methyl-pyrazol-1-yl)-ethanone;

1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone;

2-(3,5-Dimethyl-[1,2,4]triazol-1-yl)-1-{(R)-4-[2-(2-ethoxy-pyrimidin-5-yl)-5-trifluoromethyl-1,2,3,4-tetrahydro-isoquinolin-8-yl]-2-methyl-piperazin-1-yl}-ethanone;
2-(3,5-Dimethyl-pyrazol-1-yl)-1-{(R)-4-[2-(2-ethoxy-pyrimidin-5-yl)-5-trifluoromethyl-1,2,3,4-tetrahydro-isoquinolin-8-yl]-2-methyl-piperazin-1-yl}-ethanone;
2-(3,5-Dimethyl-pyrazol-1-yl)-1-{(R)-2-methyl-4-[2-(5-phenyl-oxazol-2-yl)-5-trifluoromethyl-1,2,3,4-tetrahydro-isoquinolin-8-yl]-piperazin-1-yl}-ethanone;
1-[(R)-4-(2-Benzothiazol-2-yl-5-trifluoromethyl-1,2,3,4-tetrahydro-isoquinolin-8-yl)-2-methyl-piperazin-1-yl]-2-(3,5-dimethyl-pyrazol-1-yl)-ethanone;
2-(3,5-Dimethyl-[1,2,4]triazol-1-yl)-1-{(R)-4-[2-(2-ethyl-pyrimidin-5-yl)-5-trifluoromethyl-1,2,3,4-tetrahydro-isoquinolin-8-yl]-2-methyl-piperazin-1-yl}-ethanone;
2-(3,5-Dimethyl-[1,2,4]triazol-1-yl)-1-{(R)-2-methyl-4-[5-trifluoromethyl-2-(2-trifluoromethyl-pyrimidin-5-yl)-1,2,3,4-tetrahydro-isoquinolin-8-yl]-piperazin-1-yl}-ethanone;
8-[(R)-4-(2-Imidazo[4,5-b]pyridin-3-yl-acetyl)-3-methyl-piperazin-1-yl]-3,4-dihydro-1H-isoquinoline-2-carboxylic acid benzyl ester;
1-[(R)-4-(2-Cyclopropanecarbonyl-1,2,3,4-tetrahydro-isoquinolin-8-yl)-2-methyl-piperazin-1-yl]-2-imidazo[4,5-b]pyridin-3-yl-ethanone;
2-Imidazo[4,5-b]pyridin-3-yl-1-{(R)-4-[2-(4-methoxy-benzoyl)-1,2,3,4-tetrahydro-isoquinolin-8-yl]-2-methyl-piperazin-1-yl}-ethanone;
2-Imidazo[4,5-b]pyridin-3-yl-1-{(R)-2-methyl-4-[2-(2-pyridin-3-yl-acetyl)-1,2,3,4-tetrahydro-isoquinolin-8-yl]-piperazin-1-yl}-ethanone;
1-{8-[(R)-4-(2-Imidazo[4,5-b]pyridin-3-yl-acetyl)-3-methyl-piperazin-1-yl]-3,4-dihydro-1H-isoquinolin-2-yl}-3-(4-methoxy-phenyl)-propan-1-one;
2-Imidazo[4,5-b]pyridin-3-yl-1-{(R)-2-methyl-4-[2-(oxazole-4-carbonyl)-1,2,3,4-tetrahydro-isoquinolin-8-yl]-piperazin-1-yl}-ethanone;
2-Imidazo[4,5-b]pyridin-3-yl-1-{(R)-4-[2-(2-indol-1-yl-acetyl)-1,2,3,4-tetrahydro-isoquinolin-8-yl]-2-methyl-piperazin-1-yl}-ethanone;
1-{8-[(R)-4-(2-Imidazo[4,5-b]pyridin-3-yl-acetyl)-3-methyl-piperazin-1-yl]-3,4-dihydro-1H-isoquinolin-2-yl}-2-methyl-propan-1-one;
2-Imidazo[4,5-b]pyridin-3-yl-1-{(R)-4-[2-(2-methoxy-acetyl)-1,2,3,4-tetrahydro-isoquinolin-8-yl]-2-methyl-piperazin-1-yl}-ethanone;
1-[(R)-4-(2-Cyclopentanecarbonyl-1,2,3,4-tetrahydro-isoquinolin-8-yl)-2-methyl-piperazin-1-yl]-2-imidazo[4,5-b]pyridin-3-yl-ethanone;
1-[(R)-4-(2-Cyclohexanecarbonyl-1,2,3,4-tetrahydro-isoquinolin-8-yl)-2-methyl-piperazin-1-yl]-2-imidazo[4,5-b]pyridin-3-yl-ethanone;
2-Imidazo[4,5-b]pyridin-3-yl-1-{(R)-2-methyl-4-[2-((R)-1,2,3,4-tetrahydro-naphthalene-1-carbonyl)-1,2,3,4-tetrahydro-isoquinolin-8-yl]-piperazin-1-yl}-ethanone;
1-[(R)-4-(2-Benzoyl-1,2,3,4-tetrahydro-isoquinolin-8-yl)-2-methyl-piperazin-1-yl]-2-imidazo[4,5-b]pyridin-3-yl-ethanone;
2-Imidazo[4,5-b]pyridin-3-yl-1-{(R)-2-methyl-4-[2-(4-methyl-benzoyl)-1,2,3,4-tetrahydro-isoquinolin-8-yl]-piperazin-1-yl}-ethanone;
1-{(R)-4-[2-(4-Chloro-benzoyl)-1,2,3,4-tetrahydro-isoquinolin-8-yl]-2-methyl-piperazin-1-yl}-2-imidazo[4,5-b]pyridin-3-yl-ethanone;
1-{(R)-4-[2-(3,4-Dichloro-benzoyl)-1,2,3,4-tetrahydro-isoquinolin-8-yl]-2-methyl-piperazin-1-yl}-2-imidazo[4,5-b]pyridin-3-yl-ethanone;
1-{(R)-4-[2-(3-Dimethylamino-benzoyl)-1,2,3,4-tetrahydro-isoquinolin-8-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[2-(4-trifluoromethyl-benzoyl)-1,2,3,4-tetrahydro-isoquinolin-8-yl]-piperazin-1-yl}-ethanone;
2-Imidazo[4,5-b]pyridin-3-yl-1-[(R)-2-methyl-4-(2-phenylacetyl-1,2,3,4-tetrahydro-isoquinolin-8-yl)-piperazin-1-yl]-ethanone;
(R)-1-{8-[(R)-4-(2-Imidazo[4,5-b]pyridin-3-yl-acetyl)-3-methyl-piperazin-1-yl]-3,4-dihydro-1H-isoquinolin-2-yl}-2-phenyl-propan-1-one;
2-Imidazo[4,5-b]pyridin-3-yl-1-{(R)-2-methyl-4-[2-(1-phenyl-cyclopropanecarbonyl)-1,2,3,4-tetrahydro-isoquinolin-8-yl]-piperazin-1-yl}-ethanone;
2-Imidazo[4,5-b]pyridin-3-yl-1-{(R)-2-methyl-4-[2-(2-phenoxy-acetyl)-1,2,3,4-tetrahydro-isoquinolin-8-yl]-piperazin-1-yl}-ethanone;
3-(4-Chloro-phenyl)-1-{8-[(R)-4-(2-imidazo[4,5-b]pyridin-3-yl-acetyl)-3-methyl-piperazin-1-yl]-3,4-dihydro-1H-isoquinolin-2-yl}-propan-1-one;
1-{8-[(R)-4-(2-Imidazo[4,5-b]pyridin-3-yl-acetyl)-3-methyl-piperazin-1-yl]-3,4-dihydro-1H-isoquinolin-2-yl}-3-phenyl-propan-1-one;
3-(3,4-Dichloro-phenyl)-1-{8-[(R)-4-(2-imidazo[4,5-b]pyridin-3-yl-acetyl)-3-methyl-piperazin-1-yl]-3,4-dihydro-1H-isoquinolin-2-yl}-propan-1-one;
2-Imidazo[4,5-b]pyridin-3-yl-1-{(R)-2-methyl-4-[2-(quinoline-6-carbonyl)-1,2,3,4-tetrahydro-isoquinolin-8-yl]-piperazin-1-yl}-ethanone;
1-{(R)-4-[2-(2-Benzoimidazol-1-yl-acetyl)-1,2,3,4-tetrahydro-isoquinolin-8-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[2-(2-pyrazol-1-yl-acetyl)-1,2,3,4-tetrahydro-isoquinolin-8-yl]-piperazin-1-yl}-ethanone;
2-Imidazo[4,5-b]pyridin-3-yl-1-{(R)-2-methyl-4-[2-(2-morpholin-4-yl-acetyl)-1,2,3,4-tetrahydro-isoquinolin-8-yl]-piperazin-1-yl}-ethanone;
2-Imidazo[4,5-b]pyridin-3-yl-1-{(R)-2-methyl-4-[2-(2-methyl-2H-pyrazole-3-carbonyl)-1,2,3,4-tetrahydro-isoquinolin-8-yl]-piperazin-1-yl}-ethanone;
2-Imidazo[4,5-b]pyridin-3-yl-1-{(R)-2-methyl-4-[2-(5-methyl-pyridin-2-yl)-1,2,3,4-tetrahydro-isoquinolin-8-yl]-piperazin-1-yl}-ethanone;
1-{(R)-4-[2-(5-Fluoro-pyridin-2-yl)-1,2,3,4-tetrahydro-isoquinolin-8-yl]-2-methyl-piperazin-1-yl}-2-imidazo[4,5-b]pyridin-3-yl-ethanone;
2-Imidazo[4,5-b]pyridin-3-yl-1-{(R)-2-methyl-4-[2-(6-methyl-pyridin-3-yl)-1,2,3,4-tetrahydro-isoquinolin-8-yl]-piperazin-1-yl}-ethanone;
1-{(R)-4-[2-(4-Chloro-phenyl)-1,2,3,4-tetrahydro-isoquinolin-8-yl]-2-methyl-piperazin-1-yl}-2-imidazo[4,5-b]pyridin-3-yl-ethanone;
2-Imidazo[4,5-b]pyridin-3-yl-1-{(R)-4-[2-(2-methoxy-phenyl)-1,2,3,4-tetrahydro-isoquinolin-8-yl]-2-methyl-piperazin-1-yl}-ethanone;
4-{8-[(R)-4-(2-Imidazo[4,5-b]pyridin-3-yl-acetyl)-3-methyl-piperazin-1-yl]-3,4-dihydro-1H-isoquinolin-2-yl}-benzonitrile;
2-Imidazo[4,5-b]pyridin-3-yl-1-{(R)-2-methyl-4-[2-(4-trifluoromethyl-phenyl)-1,2,3,4-tetrahydro-isoquinolin-8-yl]-piperazin-1-yl}-ethanone;
2-Imidazo[4,5-b]pyridin-3-yl-1-{(R)-2-methyl-4-[2-(3-methoxy-phenyl)-1,2,3,4-tetrahydro-isoquinolin-8-yl]-2-methyl-piperazin-1-yl}-ethanone;

2-Imidazo[4,5-b]pyridin-3-yl-1-{(R)-2-methyl-4-[2-(4-trifluoromethoxy-phenyl)-1,2,3,4-tetrahydro-isoquinolin-8-yl]-piperazin-1-yl}-ethanone;

1-{(R)-4-[2-(4-Fluoro-phenyl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(6-trifluoromethyl-pyridin-3-yl)-1,2,3,4-tetrahydro-isoquinolin-8-yl]-piperazin-1-yl}-ethanone;

2-Imidazo[4,5-b]pyridin-3-yl-1-[(R)-2-methyl-4-(2-phenyl-1,2,3,4-tetrahydro-isoquinolin-8-yl)-piperazin-1-yl]-ethanone;

2-Imidazo[4,5-b]pyridin-3-yl-1-[(R)-2-methyl-4-(2-pyrimidin-2-yl-1,2,3,4-tetrahydro-isoquinolin-8-yl)-piperazin-1-yl]-ethanone;

2-Imidazo[4,5-b]pyridin-3-yl-1-{(R)-2-methyl-4-[2-(5-trifluoromethyl-pyridin-2-yl)-1,2,3,4-tetrahydro-isoquinolin-8-yl]-piperazin-1-yl}-ethanone;

2-Imidazo[4,5-b]pyridin-3-yl-1-[(R)-2-methyl-4-(2-pyridin-2-yl-1,2,3,4-tetrahydro-isoquinolin-8-yl)-piperazin-1-yl]-ethanone;

2-Imidazo[4,5-b]pyridin-3-yl-1-{(R)-4-[2-(4-methoxy-phenyl)-1,2,3,4-tetrahydro-isoquinolin-8-yl]-2-methyl-piperazin-1-yl}-ethanone;

2-Imidazo[4,5-b]pyridin-3-yl-1-[(R)-2-methyl-4-(2-pyrimidin-5-yl-1,2,3,4-tetrahydro-isoquinolin-8-yl)-piperazin-1-yl]-ethanone;

2-Imidazo[4,5-b]pyridin-3-yl-1-{(R)-2-methyl-4-[2-(2-trifluoromethyl-pyrimidin-5-yl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(5-methyl-pyrimidin-2-yl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(2-methyl-pyrimidin-5-yl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(2-propyl-pyrimidin-5-yl)-1,2,3,4-tetrahydro-isoquinolin-8-yl]-piperazin-1-yl}-ethanone;

2-Imidazo[4,5-b]pyridin-3-yl-1-{(R)-4-[2-(2-isopropoxy-pyrimidin-5-yl)-1,2,3,4-tetrahydro-isoquinolin-8-yl]-2-methyl-piperazin-1-yl}-ethanone;

2-Imidazo[4,5-b]pyridin-3-yl-1-((R)-2-methyl-4-{2-[2-(2,2,2-trifluoro-ethoxy)-pyrimidin-5-yl]-1,2,3,4-tetrahydro-isoquinolin-8-yl}-piperazin-1-yl)-ethanone;

2-Imidazo[4,5-b]pyridin-3-yl-1-[(R)-2-methyl-4-(2-thiazol-2-yl-1,2,3,4-tetrahydro-isoquinolin-8-yl)-piperazin-1-yl]-ethanone;

2-Imidazo[4,5-b]pyridin-3-yl-1-{(R)-2-methyl-4-[2-(4-methyl-thiazol-2-yl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(5-phenyl-thiazol-2-yl)-1,2,3,4-tetrahydro-isoquinolin-8-yl]-piperazin-1-yl}-ethanone;

1-{(R)-4-[2-(4,5-Dimethyl-thiazol-2-yl)-1,2,3,4-tetrahydro-isoquinolin-8-yl]-2-methyl-piperazin-1-yl}-2-imidazo[4,5-b]pyridin-3-yl-ethanone;

2-{8-[(R)-4-(2-Imidazo[4,5-b]pyridin-3-yl-acetyl)-3-methyl-piperazin-1-yl]-3,4-dihydro-1H-isoquinolin-2-yl}-thiazole-4-carbonitrile;

2-Imidazo[4,5-b]pyridin-3-yl-1-{(R)-4-[2-(2-methoxy-pyrimidin-5-yl)-1,2,3,4-tetrahydro-isoquinolin-8-yl]-2-methyl-piperazin-1-yl}-ethanone;

2-Imidazo[4,5-b]pyridin-3-yl-1-{(R)-4-[2-(6-methoxy-pyridazin-3-yl)-1,2,3,4-tetrahydro-isoquinolin-8-yl]-2-methyl-piperazin-1-yl}-ethanone;

2-Imidazo[4,5-b]pyridin-3-yl-1-{(R)-4-[2-(6-methoxy-pyrazin-2-yl)-1,2,3,4-tetrahydro-isoquinolin-8-yl]-2-methyl-piperazin-1-yl}-ethanone;

1-{(R)-4-[2-(4,6-Dimethoxy-[1,3,5]triazin-2-yl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-4-[2-(2-methoxy-pyrimidin-4-yl)-1,2,3,4-tetrahydro-isoquinolin-8-yl]-2-methyl-piperazin-1-yl}-ethanone;

1-{(R)-4-[2-(2-Ethoxy-pyrimidin-5-yl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(4-phenyl-thiazol-2-yl)-1,2,3,4-tetrahydro-isoquinolin-8-yl]-piperazin-1-yl}-ethanone;

2-(3,5-Dimethyl-[1,2,4]triazol-1-yl)-1-{(R)-2-methyl-4-[2-(2-trifluoromethyl-pyrimidin-5-yl)-1,2,3,4-tetrahydro-isoquinolin-8-yl]-piperazin-1-yl}-ethanone;

1-{(R)-4-[2-(2-Cyclopropyl-pyrimidin-5-yl)-1,2,3,4-tetrahydro-isoquinolin-8-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(R)-4-[2-(2-ethoxy-pyrimidin-5-yl)-1,2,3,4-tetrahydro-isoquinolin-8-yl]-2-methyl-piperazin-1-yl}-ethanone;

2-(3,5-Dimethyl-pyrazol-1-yl)-1-{(R)-4-[2-(2-ethoxy-pyrimidin-5-yl)-1,2,3,4-tetrahydro-isoquinolin-8-yl]-2-methyl-piperazin-1-yl}-ethanone;

1-{(R)-4-[2-(2-Ethoxy-pyrimidin-5-yl)-5-fluoro-1,2,3,4-tetrahydro-isoquinolin-8-yl]-2-methyl-piperazin-1-yl}-2-imidazo[4,5-b]pyridin-3-yl-ethanone;

2-(3,5-Dimethyl-pyrazol-1-yl)-1-{(R)-4-[2-(2-ethoxy-pyrimidin-5-yl)-5-fluoro-1,2,3,4-tetrahydro-isoquinolin-8-yl]-2-methyl-piperazin-1-yl}-ethanone;

2-(3,5-Dimethyl-[1,2,4]triazol-1-yl)-1-{(R)-4-[2-(2-ethoxy-pyrimidin-5-yl)-5-fluoro-1,2,3,4-tetrahydro-isoquinolin-8-yl]-2-methyl-piperazin-1-yl}-ethanone;

2-(3,5-Dimethyl-[1,2,4]triazol-1-yl)-1-{(R)-4-[5-fluoro-2-(2-trifluoromethyl-pyrimidin-5-yl)-1,2,3,4-tetrahydro-isoquinolin-8-yl]-2-methyl-piperazin-1-yl}-ethanone;

1-{(R)-4-[2-(2-Cyclopropyl-pyrimidin-5-yl)-5-fluoro-1,2,3,4-tetrahydro-isoquinolin-8-yl]-2-methyl-piperazin-1-yl}-2-(3,5-dimethyl-[1,2,4]triazol-1-yl)-ethanone;

1-{(R)-4-[2-(2-Ethoxy-pyrimidin-5-yl)-6-trifluoromethyl-1,2,3,4-tetrahydro-isoquinolin-8-yl]-2-methyl-piperazin-1-yl}-2-imidazo[4,5-b]pyridin-3-yl-ethanone;

8-[(R)-3-Methyl-4-(2-pyrazol-1-yl-acetyl)-piperazin-1-yl]-3,4-dihydro-1H-isoquinoline-2-carboxylic acid benzyl ester;

8-{(R)-4-[2-(3,5-Dimethyl-[1,2,4]triazol-1-yl)-acetyl]-3-methyl-piperazin-1-yl}-3,4-dihydro-1H-isoquinoline-2-carboxylic acid benzyl ester;

8-[4-(2-Imidazo[4,5-b]pyridin-3-yl-acetyl)-piperazin-1-yl]-3,4-dihydro-1H-isoquinoline-2-carboxylic acid benzyl ester;

8-[4-(2-Pyrrolo[2,3-b]pyridin-1-yl-acetyl)-piperazin-1-yl]-3,4-dihydro-1H-isoquinoline-2-carboxylic acid benzyl ester;

8-{4-[2-(3-Methyl-2-oxo-2,3-dihydro-benzoimidazol-1-yl)-acetyl]-piperazin-1-yl}-3,4-dihydro-1H-isoquinoline-2-carboxylic acid benzyl ester;

1-{2-[4-(2-Benzoyl-1,2,3,4-tetrahydro-isoquinolin-8-yl)-piperazin-1-yl]-2-oxo-ethyl}-3-methyl-1,3-dihydro-benzoimidazol-2-one;

1-Methyl-3-{2-oxo-2-[4-(2-phenylacetyl-1,2,3,4-tetrahydro-isoquinolin-8-yl)-piperazin-1-yl]-ethyl}-1,3-dihydro-benzoimidazol-2-one;

2-Imidazo[4,5-b]pyridin-3-yl-1-[4-(2-phenylmethanesulfo-
nyl-1,2,3,4-tetrahydro-isoquinolin-8-yl)-piperazin-1-yl]-
ethanone;
1-{(R)-4-[2-(4-Chloro-benzyl)-1,2,3,4-tetrahydro-isoquino-
lin-8-yl]-2-methyl-piperazin-1-yl}-2-imidazo[4,5-b]pyri-
din-3-yl-ethanone;
5-Bromo-8-[(R)-4-(2-imidazo[4,5-b]pyridin-3-yl-acetyl)-3-
methyl-piperazin-1-yl]-3,4-dihydro-1H-isoquinoline-2-
carboxylic acid benzyl ester;
8-[(R)-4-(2-Imidazo[4,5-b]pyridin-3-yl-acetyl)-3-methyl-
piperazin-1-yl]-5-trifluoromethyl-3,4-dihydro-1H-isoqui-
noline-2-carboxylic acid benzyl ester;
5-Cyano-8-[(R)-4-(2-imidazo[4,5-b]pyridin-3-yl-acetyl)-3-
methyl-piperazin-1-yl]-3,4-dihydro-1H-isoquinoline-2-
carboxylic acid benzyl ester; and
1-{(R)-4-[5,6-Difluoro-2-(2-trifluoromethyl-pyrimidin-5-
yl)-1,2,3,4-tetrahydro-isoquinolin-8-yl]-2-methyl-piper-
azin-1-yl}-2-(3,5-dimethyl-[1,2,4]triazol-1-yl)-ethanone;
or salts (in particular pharmaceutically acceptable salts) of
such compounds.

31) The invention, thus, relates to compounds of the
Formula (I) as defined in embodiment 1), compounds of the
Formula ($I_{Ar}$) as defined in embodiment 19), and to such
compounds further limited by the characteristics of any one
of embodiments 2) to 18) and 20) to 30), all under consid-
eration of their respective dependencies; to pharmaceuti-
cally acceptable salts thereof; and to the use of such com-
pounds as medicaments especially in the treatment of
disorders relating to a dysfunction of the CXCR3 receptor or
dysfunction of ligands signalling through CXCR3, such as
especially autoimmune disorders, inflammatory diseases,
infectious diseases, transplant rejection, fibrosis, neurode-
generative disorders and cancer. Especially the following
embodiments relating to the compounds of formulae (I) and
($I_{Ar}$) are thus possible and intended and herewith specifically
disclosed in individualized form: 1, 2+1, 3+1, 4+1, 5 6+1,
6+2+1, 7+1, 7+2+1, 7+3+1, 7+4+1, 7+5+1, 8+1, 8+2+1,
8+3+1, 8+4+1, 8+5+1, 9+1, 9+2+1, 10+1, 10+2+1, 10+6+1,
10+6+2+1, 10+7+1, 10+7+2+1, 10+7+3+1, 10+7+4+1,
10+7+5+1, 10+8+1, 10+8+2+1, 10+8+3+1, 10+8+4+1,
10+8+5+1, 10+9+1, 10+9+2+1, 11+1, 11+2+1, 11+4+1,
11+6+1, 11+6+2+1, 11+7+1, 11+7+2+1, 11+7+3+1, 11+7+
4+1, 11+7+5+1, 11+8+1, 11+8+2+1, 11+8+3+1, 11+8+4+1,
11+8+5+1, 11+9+1, 11+9+2+1, 12+1, 12+2+1, 12+4+1,
12+6+1, 12+6+2+1, 12+7+1, 12+7+2+1, 12+7+3+1, 12+7+
4+1, 12+7+5+1, 12+8+1, 12+8+2+1, 12+8+3+1, 12+8+4+1,
12+8+5+1, 12+9+1, 12+9+2+1, 13+1, 13+2+1, 13+4+1,
13+6+1, 13+6+2+1, 13+7+1, 13+7+2+1, 13+7+3+1, 13+7+
4+1, 13+7+5+1, 13+8+1, 13+8+2+1, 13+8+3+1, 13+8+4+1,
13+8+5+1, 13+9+1, 13+9+2+1, 14+1, 14+2+1, 14+3+1,
14+4+1, 14+5+1, 14+6+1, 14+6+2+1, 14+7+1, 14+7+2+1,
14+7+3+1, 14+7+4+1, 14+7+5+1, 14+8+1, 14+8+2+1,
14+8+3+1, 14+8+4+1, 14+8+5+1, 14+9+1, 14+9+2+1,
15+1, 15+6+1, 15+6+2+1, 15+7+1, 15+7+2+1, 15+7+3+1,
15+7+4+1, 15+7+5+1, 15+8+1, 15+8+2+1, 15+8+3+1,
15+8+4+1, 15+8+5+1, 15+9+1, 15+9+2+1, 16+1, 16+2+1,
16+3+1, 16+4+1, 16+5+1, 16+6+1, 16+6+2+1, 16+7+1;
16+7+2+1, 16+7+3+1, 16+7+4+1, 16+7+5+1, 16+8+1,
16+8+2+1, 16+8+3+1, 16+8+4+1, 16+8+5+1, 16+9+1,
16+9+2+1, 16+10+1, 16+10+2+1, 16+10+6+1, 16+10+6+
2+1, 16+10+7+1, 16+10+7+2+1, 16+10+7+3+1, 16+10+7+
4+1, 16+10+7+5+1, 16+10+8+1, 16+10+8+2+1, 16+10+8+
3+1, 16+10+8+4+1, 16+10+8+5+1, 16+10+9+1, 16+10+9+
2+1, 16+11+1, 16+11+2+1, 16+11+4+1, 16+11+6+1,
16+11+6+2+1, 16+11+7+1, 16+11+7+2+1, 16+11+7+3+1,
16+11+7+4+1, 16+11+7+5+1, 16+11+8+1, 16+11+8+2+1,
16+11+8+3+1, 16+11+8+4+1, 16+11+8+5+1, 16+11+9+1,
16+11+9+2+1, 16+12+1, 16+12+2+1, 16+12+4+1, 16+12+
6+1, 16+12+6+2+1, 16+12+7+1, 16+12+7+2+1, 16+12+7+
3+1, 16+12+7+4+1, 16+12+7+5+1, 16+12+8+1, 16+12+8+
2+1, 16+12+8+3+1, 16+12+8+4+1, 16+12+8+5+1, 16+12+
9+1, 16+12+9+2+1, 16+13+1, 16+13+2+1, 16+13+4+1,
16+13+6+1, 16+13+6+2+1, 16+13+7+1, 16+13+7+2+1,
16+13+7+3+1, 16+13+7+4+1, 16+13+7+5+1, 16+13+8+1,
16+13+8+2+1, 16+13+8+3+1, 16+13+8+4+1, 16+13+8+5+
1, 16+13+9+1, 16+13+9+2+1, 16+14+1, 16+14+2+1,
16+14+3+1, 16+14+4+1, 16+14+5+1, 16+14+6+1, 16+14+
6+2+1, 16+14+7+1, 16+14+7+2+1, 16+14+7+3+1, 16+14+
7+4+1, 16+14+7+5+1, 16+14+8+1, 16+14+8+2+1, 16+14+
8+3+1, 16+14+8+4+1, 16+14+8+5+1, 16+14+9+1, 16+14+
9+2+1, 16+15+1, 16+15+6+1, 16+15+6+2+1, 16+15+7+1,
16+15+7+2+1, 16+15+7+3+1, 16+15+7+4+1, 16+15+7+5+
1, 16+15+8+1, 16+15+8+2+1, 16+15+8+3+1, 16+15+8+4+
1, 16+15+8+5+1, 16+15+9+1, 16+15+9+2+1, 17+1, 17+2+
1, 17+3+1, 17+4+1, 17+5+1, 17+6+1, 17+6+2+1, 17+7+1,
17+7+2+1, 17+7+3+1, 17+7+4+1, 17+7+5+1, 17+8+1,
17+8+2+1, 17+8+3+1, 17+8+4+1, 17+8+5+1, 17+9+1,
17+9+2+1, 17+10+1, 17+10+2+1, 17+10+6+1, 17+10+6+
2+1, 17+10+7+1, 17+10+7+2+1, 17+10+7+3+1, 17+10+7+
4+1, 17+10+7+5+1, 17+10+8+1, 17+10+8+2+1, 17+10+8+
3+1, 17+10+8+4+1, 17+10+8+5+1, 17+10+9+1, 17+10+9+
2+1, 17+11+1, 17+11+2+1, 17+11+4+1, 17+11+6+1,
17+11+6+2+1, 17+11+7+1, 17+11+7+2+1, 17+11+7+3+1,
17+11+7+4+1, 17+11+7+5+1, 17+11+8+1, 17+11+8+2+1,
17+11+8+3+1, 17+11+8+4+1, 17+11+8+5+1, 17+11+9+1,
17+11+9+2+1, 17+12+1, 17+12+2+1, 17+12+4+1, 17+12+
6+1, 17+12+6+2+1, 17+12+7+1, 17+12+7+2+1, 17+12+7+
3+1, 17+12+7+4+1, 17+12+7+5+1, 17+12+8+1, 17+12+8+
2+1, 17+12+8+3+1, 17+12+8+4+12+8+5+1, 17+12+9+1,
17+12+9+2+1, 17+13+1, 17+13+2+1, 17+13+4+1, 17+13+
6+1, 17+13+6+2+1, 17+13+7+1, 17+13+7+2+1, 17+13+7+
3+1, 17+13+7+4+1, 17+13+7+5+1, 17+13+8+1, 17+13+8+
2+1, 17+13+8+3+1, 17+13+8+4+1, 17+13+8+5+1, 17+13+
9+1, 17+13+9+2+1, 17+14+1, 17+14+2+1, 17+14+3+1,
17+14+4+1, 17+14+5+1, 17+14+6+1, 17+14+6+2+1,
17+14+7+1, 17+14+7+2+1, 17+14+7+3+1, 17+14+7+4+1,
17+14+7+5+1, 17+14+8+1, 17+14+8+2+1, 17+14+8+3+1,
17+14+8+4+1, 17+14+8+5+1, 17+14+9+1, 17+14+9+2+1,
17+15+1, 17+15+6+1, 17+15+6+2+1, 17+15+7+1, 17+15+
7+2+1, 17+15+7+3+1, 17+15+7+4+1, 17+15+7+5+1,
17+15+8+1, 17+15+8+2+1, 17+15+8+3+1, 17+15+8+4+1,
17+15+8+5+1, 17+15+9+1, 17+15+9+2+1, 18+1, 18+2+1,
18+, 18+2+1, 18+6+1, 18+6+2+1, 18+7+1, 18+7+2+1,
18+7+3+1, 18+7+4+1, 18+7+5+1, 18+861, 18+8+2+1,
18+8+3+1, 18+8+4+1, 18+8+5+1, 18+9+1, 18+9+2+1,
18+10+1, 18+10+2+1, 18+10+6+1, 18+10+6+2+1, 18+10+
7+1, 18+10+7+2+1, 18+10+7+3+1, 18+10+7+4+1, 18+10+
7+5+1, 18+10+8+1, 18+10+8+2+1, 18+10+8+3+1, 18+10+
8+4+1, 18+10+8+5+1, 18+10+9+1, 18+10+9+2+1, 18+11+
1, 18+11+2+1, 18+11+4+1, 18+11+6+1, 18+11+6+2+1,
18+11+7+1, 18+11+7+2+1, 18+11+7+3+1, 18+11+7+4+1,
18+11+7+5+1, 18+11+8+1, 18+11+8+2+1, 18+11+8+3+1,
18+11+8+4+1, 18+11+8+5+1, 18+11+9+1, 18+11+9+2+1,
18+12+1, 18+12+2+1, 18+12+4+1, 18+12+6+1, 18+12+6+
2+1, 18+12+7+1, 18+12+7+2+1, 18+12+7+3+1, 18+12+7+
4+1, 18+12+7+5+1, 18+12+8+1, 18+12+8+2+1, 18+12+8+
3+1, 18+12+8+4+1, 18+12+8+5+1, 18+12+9+1, 18+12+9+
2+1, 18+13+1, 18+13+2+1, 18+13+4+1, 18+13+6+1,
18+13+6+2+1, 18+13+7+1, 18+13+7+2+1, 18+13+7+3+1,
18+13+7+4+1, 18+13+7+5+1, 18+13+8+1, 18+13+8+2+1,
18+13+8+3+1, 18+13+8+4+1, 18+13+8+5+1, 18+13+9+1,
18+13+9+2+1, 18+14+1, 18+14+2+1, 18+14+3+1, 18+14+
4+1, 18+14+5+1, 18+14+6+1, 18+14+6+2+1, 18+14+7+1,
18+14+7+2+1, 18+14+7+3+1, 18+14+7+4+1, 18+14+7+5+

1, 18+14+8+1, 18+14+8+2+1, 18+14+8+3+1, 18+14+8+4+1, 18+14+8+5+1, 18+14+9+1, 18+14+9+2+1, 18+15+1, 18+15+6+1, 18+15+6+2+1, 18+15+7+1, 18+15+7+2+1, 18+15+7+3+1, 18+15+7+4+1, 18+15+7+5+1, 18+15+8+1, 18+15+8+2+1, 18+15+8+3+1, 18+15+8+4+1, 18+15+8+5+1, 18+15+9+1, 18+15+9+2+1, 18+16+1, 18+16+2+1, 18+16+3+1, 18+16+4+1, 18+16+5+1, 18+16+6+1, 18+16+6+2+1, 18+16+7+1, 18+16+7+2+1, 18+16+7+3+1, 18+16+7+4+1, 18+16+7+5+1, 18+16+8+1, 18+16+8+2+1, 18+16+8+3+1, 18+16+8+4+1, 18+16+8+5+1, 18+16+9+1, 18+16+9+2+1, 18+16+10+1, 18+16+10+2+1, 18+16+10+6+1, 18+16+10+6+2+1, 18+16+10+7+1, 18+16+10+7+2+1, 18+16+10+7+3+1, 18+16+10+7+4+1, 18+16+10+7+5+1, 18+16+10+8+1, 18+16+10+8+2+1, 18+16+10+8+3+1, 18+16+10+8+4+1, 18+16+10+8+5+1, 18+16+10+9+1, 18+16+10+9+2+1, 18+16+11+1, 18+16+11+2+1, 18+16+11+4+1, 18+16+11+6+1, 18+16+11+6+2+1, 18+16+11+7+1, 18+16+11+7+2+1, 18+16+11+7+3+1, 18+16+11+7+4+1, 18+16+11+7+5+1, 18+16+11+8+1, 18+16+11+8+2+1, 18+16+11+8+3+1, 18+16+11+8+4+1, 18+16+11+8+5+1, 18+16+11+9+1, 18+16+11+9+2+1, 18+16+12+1, 18+16+12+2+1, 18+16+12+4+1, 18+16+12+6+1, 18+16+12+6+2+1, 18+16+12+7+1, 18+16+12+7+2+1, 18+16+12+7+3+1, 18+16+12+7+4+1, 18+16+12+7+5+1, 18+16+12+8+1, 18+16+12+8+2+1, 18+16+12+8+3+1, 18+16+12+8+4+1, 18+16+12+8+5+1, 18+16+12+9+1, 18+16+12+9+2+1, 18+16+13+1, 18+16+13+2+1, 18+16+13+4+1, 18+16+13+6+1, 18+16+13+6+2+1, 18+16+13+7+1, 18+16+13+7+2+1, 18+16+13+7+3+1, 18+16+13+7+4+1, 18+16+13+7+5+1, 18+16+13+8+1, 18+16+13+8+2+1, 18+16+13+8+3+1, 18+16+13+8+4+1, 18+16+13+8+5+1, 18+16+13+9+1, 18+16+13+9+2+1, 18+16+14+1, 18+16+14+2+1, 18+16+14+3+1, 18+16+14+4+1, 18+16+14+5+1, 18+16+14+6+1, 18+16+14+6+2+1, 18+16+14+7+1, 18+16+14+7+2+1, 18+16+14+7+3+1, 18+16+14+7+4+1, 18+16+14+7+5+1, 18+16+14+8+1, 18+16+14+8+2+1, 18+16+14+8+3+1, 18+16+14+8+4+1, 18+16+14+8+5+1, 18+16+14+9+1, 18+16+14+9+2+1, 18+16+15+1, 18+16+15+6+1, 18+16+15+6+2+1, 18+16+15+7+1, 18+16+15+7+2+1, 18+16+15+7+3+1, 18+16+15+7+4+1, 18+16+15+7+5+1, 18+16+15+8+1, 18+16+15+8+2+1, 18+16+15+8+3+1, 18+16+15+8+4+1, 18+16+15+8+5+1, 18+16+15+9+1, 18+16+15+9+2+1, 18+17+1, 18+17+2+1, 18+17+3+1, 18+17+4+1, 18+17+5+1, 18+17+6+1, 18+17+6+2+1, 18+17+7+1, 18+17+7+2+1, 18+17+7+3+1, 18+17+7+4+1, 18+17+7+5+1, 18+17+8+1, 18+17+8+2+1, 18+17+8+3+1, 18+17+8+4+1, 18+17+8+5+1, 18+17+9+1, 18+17+9+2+1, 18+17+10+1, 18+17+10+2+1, 18+17+10+6+1, 18+17+10+6+2+1, 18+17+10+7+1, 18+17+10+7+2+1, 18+17+10+7+3+1, 18+17+10+7+4+1, 18+17+10+7+5+1, 18+17+10+8+1, 18+17+10+8+2+1, 18+17+10+8+3+1, 18+17+10+8+4+1, 18+17+10+8+5+1, 18+17+10+9+1, 18+17+10+9+2+1, 18+17+11+1, 18+17+11+2+1, 18+17+11+4+1, 18+17+11+6+1, 18+17+11+6+2+1, 18+17+11+7+1, 18+17+11+7+2+1, 18+17+11+7+3+1, 18+17+11+7+4+1, 18+17+11+7+5+1, 18+17+11+8+1, 18+17+11+8+2+1, 18+17+11+8+3+1, 18+17+11+8+4+1, 18+17+11+8+5+1, 18+17+11+9+1, 18+17+11+9+2+1, 18+17+12+1, 18+17+12+2+1, 18+17+12+4+1, 18+17+12+6+1, 18+17+12+6+2+1, 18+17+12+7+1, 18+17+12+7+2+1, 18+17+12+7+3+1, 18+17+12+7+4+1, 18+17+12+7+5+1, 18+17+12+8+1, 18+17+12+8+2+1, 18+17+12+8+3+1, 18+17+12+8+4+1, 18+17+12+8+5+1, 18+17+12+9+1, 18+17+12+9+2+1, 18+17+13+1, 18+17+13+2+1, 18+17+13+4+1, 18+17+13+6+1, 18+17+13+6+2+1, 18+17+13+7+1, 18+17+13+7+2+1, 18+17+13+7+3+1, 18+17+13+7+4+1, 18+17+13+7+5+1, 18+17+13+8+1, 18+17+13+8+2+1, 18+17+13+8+3+1, 18+17+13+8+4+1, 18+17+13+8+5+1, 18+17+13+9+1, 18+17+13+9+2+1, 18+17+14+1, 18+17+14+2+1, 18+17+14+3+1, 18+17+14+4+1, 18+17+14+5+1, 18+17+14+6+1, 18+17+14+6+2+1, 18+17+14+7+1, 18+17+14+7+2+1, 18+17+14+7+3+1, 18+17+14+7+4+1, 18+17+14+7+5+1, 18+17+14+8+1, 18+17+14+8+2+1, 18+17+14+8+3+1, 18+17+14+8+4+1, 18+17+14+8+5+1, 18+17+14+9+1, 18+17+14+9+2+1, 18+17+15+1, 18+17+15+6+1, 18+17+15+6+2+1, 18+17+15+7+1, 18+17+15+7+2+1, 18+17+15+7+3+1, 18+17+15+7+4+1, 18+17+15+7+5+1, 18+17+15+8+1, 18+17+15+8+2+1, 18+17+15+8+3+1, 18+17+15+8+4+1, 18+17+15+8+5+1, 18+17+15+9+1, 18+17+15+9+2+1, 19+1, 20+19+1, 21+19+1, 22+19+1, 22+20+19+1, 22+21+19+1, 23+19+1, 23+20+19+1, 23+21+19+1, 24+19+1, 24+20+19+1, 24+22+19+1, 24+22+20+19+1, 24+22+21+19+1, 24+23+19+1, 24+23+20+19+1, 24+23+21+19+1, 25+19+1, 25+20+19+1, 25+22+19+1, 25+22+20+19+1, 25+22+21+19+1, 25+23+19+1, 25+23+20+19+1, 25+23+21+19+1, 26+19+1, 26+20+19+1, 26+22+19+1, 26+22+20+19+1, 26+22+21+19+1, 26+23+19+1, 26+23+20+19+1, 26+23+21+19+1, 27+25+19+1, 27+25+20+19+1, 27+25+22+19+1, 27+25+22+20+19+1, 27+25+22+21+19+1, 27+25+23+19+1, 27+25+23+20+19+1, 27+25+23+21+19+1, 27+26+19+1, 27+26+20+19+1, 27+26+22+19+1, 27+26+22+20+19+1, 27+26+22+21+19+1, 27+26+23+19+1, 27+26+23+20+19+1, 27+26+23+21+19+1, 28+1, 28+2+1, 28+3+1, 28+4+1, 28+5+1, 28+6+1, 28+6+2+1, 28+7+1, 28+7+2+1, 28+7+3+1, 28+7+4+1, 28+7+5+1, 28+8+1, 28+8+2+1, 28+8+3+1, 28+8+4+1, 28+8+5+1, 28+9+1, 28+9+2+1, 28+10+1, 28+10+2+1, 28+10+6+1, 28+10+6+2+1, 28+10+7+1, 28+10+7+2+1, 28+10+7+3+1, 28+10+7+4+1, 28+10+7+5+1, 28+10+8+1, 28+10+8+2+1, 28+10+8+3+1, 28+10+8+4+1, 28+10+8+5+1, 28+10+9+1, 28+10+9+2+1, 28+11+1, 28+11+2+1, 28+11+4+1, 28+11+6+1, 28+11+6+2+1, 28+11+7+1, 28+11+7+2+1, 28+11+7+3+1, 28+11+7+4+1, 28+11+7+5+1, 28+11+8+1, 28+11+8+2+1, 28+11+8+3+1, 28+11+8+4+1, 28+11+8+5+1, 28+11+9+1, 28+11+9+2+1, 28+14+1, 28+14+2+1, 28+14+3+1, 28+14+4+1, 28+14+5+1, 28+14+6+1, 28+14+6+2+1, 28+14+7+1, 28+14+7+2+1, 28+14+7+3+1, 28+14+7+4+1, 28+14+7+5+1, 28+14+8+1, 28+14+8+2+1, 28+14+8+3+1, 28+14+8+4+1, 28+14+8+5+1, 28+14+9+1, 28+14+9+2+1, 28+17+1, 28+17+2+1, 28+17+3+1, 28+17+4+1, 28+17+5+1, 28+17+6+1, 28+17+6+2+1, 28+17+7+1, 28+17+7+2+1, 28+17+7+3+1, 28+17+7+4+1, 28+17+7+5+1, 28+17+8+1, 28+17+8+2+1, 28+17+8+3+1, 28+17+8+4+1, 28+17+8+5+1, 28+17+9+1, 28+17+9+2+1, 28+17+10+1, 28+17+10+2+1, 28+17+10+6+1, 28+17+10+6+2+1, 28+17+10+7+1, 28+17+10+7+2+1, 28+17+10+7+3+1, 28+17+10+7+4+1, 28+17+10+7+5+1, 28+17+10+8+1, 28+17+10+8+2+1, 28+17+10+8+3+1, 28+17+10+8+4+1, 28+17+10+8+5+1, 28+17+10+9+1, 28+17+10+9+2+1, 28+17+11+1, 28+17+11+2+1, 28+17+11+4+1, 28+17+11+6+1, 28+17+11+6+2+1, 28+17+11+7+1, 28+17+11+7+2+1, 28+17+11+7+3+1, 28+17+11+7+4+1, 28+17+11+7+5+1, 28+17+11+8+1, 28+17+11+8+2+1, 28+17+11+8+3+1, 28+17+11+8+4+1, 28+17+11+8+5+1, 28+17+11+9+1, 28+17+11+9+2+1, 28+17+12+1, 28+17+12+2+1, 28+17+12+4+1, 28+17+12+6+1, 28+17+12+6+2+1, 28+17+12+7+1, 28+17+12+7+2+1, 28+17+12+7+3+1, 28+17+12+7+4+1, 28+17+12+7+5+1, 28+17+12+8+1, 28+17+12+8+2+1, 28+17+12+8+3+1, 28+17+12+8+4+1, 28+17+12+8+5+1, 28+17+12+9+1, 28+17+12+9+2+1, 28+17+13+1, 28+17+13+2+1, 28+17+13+4+1, 28+17+13+6+1, 28+17+13+6+2+1, 28+17+13+7+1, 28+17+13+7+2+1, 28+17+13+7+3+1, 28+17+13+7+4+1, 28+17+13+7+5+1, 28+17+13+8+1, 28+17+13+8+2+1, 28+17+13+8+3+1, 28+17+13+8+4+1, 28+17+13+8+5+1, 28+17+13+9+1, 28+17+13+9+2+1, 28+17+14+1, 28+17+14+2+1, 28+17+

14+3+1, 28+17+14+4+1, 28+17+14+5+1, 28+17+14+6+1, 28+17+14+6+2+1, 28+17+14+7+1, 28+17+14+7+2+1, 28+17+14+7+3+1, 28+17+14+7+4+1, 28+17+14+7+5+1, 28+17+14+8+1, 28+17+14+8+2+1, 28+17+14+8+3+1, 28+17+14+8+4+1, 28+17+14+8+5+1, 28+17+14+9+1, 28+17+14+9+2+1, 28+17+15+1, 28+17+15+6+1, 28+17+15+6+2+1, 28+17+15+7+1, 28+17+15+7+2+1, 28+17+15+7+3+1, 28+17+15+7+4+1, 28+17+15+7+5+1, 28+17+15+8+1, 28+17+15+8+2+1, 28+17+15+8+3+1, 28+17+15+8+4+1, 28+17+15+8+5+1, 28+17+15+9+1, 28+17+15+9+2+1, 28+19+1, 28+20+19+1, 28+21+19+1, 28+22+19+1, 28+22+20+19+1, 28+22+21+19+1, 28+23+19+1, 28+23+20+19+1, 28+23+21+19+1, 28+24+19+1, 28+24+20+19+1, 28+24+22+19+1, 28+24+22+20+19+1, 28+24+22+21+19+1, 28+24+23+19+1, 28+24+23+20+19+1, 28+24+23+21+19+1, 28+25+19+1, 28+25+20+19+1, 28+25+22+19+1, 28+25+22+20+19+1, 28+25+22+21+19+1, 28+25+23+19+1, 28+25+23+20+19+1, 28+25+23+21+19+1, 28+26+19+1, 28+26+20+19+1, 28+26+22+19+1, 28+26+22+20+19+1, 28+26+22+21+19+1, 28+26+23+19+1, 28+26+23+20+19+1, 28+26+23+21+19+1, 29+1, 29+2+1, 29+3+1, 29+4+1, 29+5+1, 29+6+1, 29+6+2+1, 29+7+1, 29+7+2+1, 29+7+3+1, 29+7+4+1, 29+7+5+1, 29+8+1, 29+8+2+1, 29+8+3+1, 29+8+4+1, 29+8+5+1, 29+9+1, 29+9+2+1, 29+10+1, 29+10+2+1, 29+10+6+1, 29+10+6+2+1, 29+10+7+1, 29+10+7+2+1, 29+10+7+3+1, 29+10+7+4+1, 29+10+7+5+1, 29+10+8+1, 29+10+8+2+1, 29+10+8+3+1, 29+10+8+4+1, 29+10+8+5+1, 29+10+9+1, 29+10+9+2+1, 29+11+1, 29+11+2+1, 29+11+4+1, 29+11+6+1, 29+11+6+2+1, 29+11+7+1, 29+11+7+2+1, 29+11+7+3+1, 29+11+7+4+1, 29+11+7+5+1, 29+11+8+1, 29+11+8+2+1, 29+11+8+3+1, 29+11+8+4+1, 29+11+8+5+1, 29+11+9+1, 29+11+9+2+1, 29+14+1, 29+14+2+1, 29+14+3+1, 29+14+4+1, 29+14+5+1, 29+14+6+1, 29+14+6+2+1, 29+14+7+1, 29+14+7+2+1, 29+14+7+3+1, 29+14+7+4+1, 29+14+7+5+1, 29+14+8+1, 29+14+8+2+1, 29+14+8+3+1, 29+14+8+4+1, 29+14+8+5+1, 29+14+9+1, 29+14+9+2+1, 29+17+1, 29+17+2+1, 29+17+3+1, 29+17+4+1, 29+17+5+1, 29+17+6+1, 29+17+6+2+1, 29+17+7+1, 29+17+7+2+1, 29+17+7+3+1, 29+17+7+4+1, 29+17+7+5+1, 29+17+8+1, 29+17+8+2+1, 29+17+8+3+1, 29+17+8+4+1, 29+17+8+5+1, 29+17+9+1, 29+17+9+2+1, 29+17+10+1, 29+17+10+2+1, 29+17+10+6+1, 29+17+10+6+2+1, 29+17+10+7+1, 29+17+10+7+2+1, 29+17+10+7+3+1, 29+17+10+7+4+1, 29+17+10+7+5+1, 29+17+10+8+1, 29+17+10+8+2+1, 29+17+10+8+3+1, 29+17+10+8+4+1, 29+17+10+8+5+1, 29+17+10+9+1, 29+17+10+9+2+1, 29+17+11+1, 29+17+11+2+1, 29+17+11+4+1, 29+17+11+6+1, 29+17+11+6+2+1, 29+17+11+7+1, 29+17+11+7+2+1, 29+17+11+7+3+1, 29+17+11+7+4+1, 29+17+11+7+5+1, 29+17+11+8+1, 29+17+11+8+2+1, 29+17+11+8+3+1, 29+17+11+8+4+1, 29+17+11+8+5+1, 29+17+11+9+1, 29+17+11+9+2+1, 29+17+12+1, 29+17+12+2+1, 29+17+12+4+1, 29+17+12+6+1, 29+17+12+6+2+1, 29+17+12+7+1, 29+17+12+7+2+1, 29+17+12+7+3+1, 29+17+12+7+4+1, 29+17+12+7+5+1, 29+17+12+8+1, 29+17+12+8+2+1, 29+17+12+8+3+1, 29+17+12+8+4+1, 29+17+12+8+5+1, 29+17+12+9+1, 29+17+12+9+2+1, 29+17+13+1, 29+17+13+2+1, 29+17+13+4+1, 29+17+13+6+1, 29+17+13+6+2+1, 29+17+13+7+1, 29+17+13+7+2+1, 29+17+13+7+3+1, 29+17+13+7+4+1, 29+17+13+7+5+1, 29+17+13+8+1, 29+17+13+8+2+1, 29+17+13+8+3+1, 29+17+13+8+4+1, 29+17+13+8+5+1, 29+17+13+9+1, 29+17+13+9+2+1, 29+17+14+1, 29+17+14+2+1, 29+17+14+3+1, 29+17+14+4+1, 29+17+14+5+1, 29+17+14+6+1, 29+17+14+6+2+1, 29+17+14+7+1, 29+17+14+7+2+1, 29+17+14+7+3+1, 29+17+14+7+4+1, 29+17+14+7+5+1, 29+17+14+8+1, 29+17+14+8+2+1, 29+17+14+8+3+1, 29+17+14+8+4+1, 29+17+14+8+5+1, 29+17+14+9+1, 29+17+14+9+2+1, 29+17+15+1, 29+17+15+6+1, 29+17+15+6+2+1, 29+17+15+7+1, 29+17+15+7+2+1, 29+17+15+7+3+1, 29+17+15+7+4+1, 29+17+15+7+5+1, 29+17+15+8+1, 29+17+15+8+2+1, 29+17+15+8+3+1, 29+17+15+8+4+1, 29+17+15+8+5+1, 29+17+15+9+1, 29+17+15+9+2+1, 29+19+1, 29+20+19+1, 29+21+19+1, 29+22+19+1, 29+22+20+19+1, 29+22+21+19+1, 29+23+19+1, 29+23+20+19+1, 29+23+21+19+1, 29+24+19+1, 29+24+20+19+1, 29+24+22+19+1, 29+24+22+20+19+1, 29+24+22+21+19+1, 29+24+23+19+1, 29+24+23+20+19+1, 29+24+23+21+19+1, 29+25+19+1, 29+25+20+19+1, 29+25+22+19+1, 29+25+22+20+19+1, 29+25+22+21+19+1, 29+25+23+19+1, 29+25+23+20+19+1, 29+25+23+21+19+1, 29+26+19+1, 29+26+20+19+1, 29+26+22+19+1, 29+26+22+20+19+1, 29+26+22+21+19+1, 29+26+23+19+1, 29+26+23+20+19+1, 29+26+23+21+19+1, and 30+1; in the list above the numbers refer to the embodiments according to their numbering provided hereinabove whereas "+" indicates the dependency from another embodiment. The different individualized embodiments are separated by commas. In other words, "6+2+1" for example refers to embodiment 6) depending on embodiment 2), depending on embodiment 1), i.e. embodiment "6+2+1" corresponds to the compounds of embodiment 1) further limited by the features of the embodiments 2) and 6).

Where the plural form is used for compounds, salts, pharmaceutical compositions, diseases or the like, this is intended to mean also a single compound, salt, pharmaceutical composition, disease or the like.

Any reference to a compound of Formula (I) as defined in any one of embodiments 1) to 31) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The present invention also includes isotopically labelled, especially $^2$H (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of Formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

The compounds of formula (I) as defined in any one of embodiments 1) to 31) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of Formula (I) as defined in any one of embodiments 1) to 31).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

Another aspect of the invention concerns a method for the prevention or the treatment of a disease or disorder as mentioned below in a patient comprising the administration to said patient of a pharmaceutically active amount of a compound of Formula (I) as defined in any one of embodiments 1) to 31) or a pharmaceutically acceptable salt thereof.

The compounds according to Formula (I) as defined in any one of embodiments 1) to 31), or pharmaceutically acceptable salts thereof, are useful for the prevention or treatment of disorders relating to a dysfunction of the CXCR3 receptor or dysfunction of ligands signalling through CXCR3.

Such disorders relating to a dysfunction of the CXCR3 receptor or its ligands are diseases or disorders where a modulator of a human CXCR3 receptor is required. The above mentioned disorders may in particular be defined as comprising autoimmune disorders, inflammatory diseases, infectious diseases, transplant rejection, fibrosis, neurodegenerative disorders and cancer.

Autoimmune disorders may be defined as comprising rheumatoid arthritis (RA); multiple sclerosis (MS); inflammatory bowel disease (IBD; comprising Crohn's disease and ulcerative colitis); systemic lupus erythematosus (SLE); psoriasis; psoriatic arthritis; lupus nephritis; interstitial cystitis; celiac disease; antiphospholipid syndrome; thyroiditis such as Hashimoto's thyroiditis; lymphocytic thyroiditis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis.

Inflammatory diseases may be defined as comprising asthma; COPD; atherosclerosis; myocarditis; dry eye syndrome (comprising Sjögren's dry eye syndrome); myopathies (comprising inflammatory myopathies); sarcoidosis; pulmonary arterial hypertension, especially associated with sarcoidosis; and obesity.

Infectious diseases may be defined as comprising diseases mediated by various infectious agents and complications resulting threrefrom; such as malaria, cerebral malaria, leprosy, tuberculosis, influenza, toxoplasma gondii, dengue, hepatitis B and C, herpes simplex, leishmania, chlamydia trachomatis, lyme disease, west nile virus.

Transplant rejection may be defined as comprising rejection of transplanted organs such as kidney, liver, heart, lung, pancreas, cornea, and skin; graft-versus-host diseases; and chronic allograft vasculopathy.

Fibrosis may be defined as comprising liver cirrhosis (comprising primary biliary cirrhosis (PBC) and autoimmune hepatitis), idiopathic pulmonary fibrosis, renal fibrosis, endomyocardial fibrosis, systemic sclerosis, and arthrofibrosis.

Neurodegenerative disorders may be defined as comprising neurodegeneration and conditions involving neuronal death such as multiple sclerosis (including relapsing remitting multiple sclerosis and progressive multiple sclerosis), Alzheimer's disease, Parkinson's disease, Huntington's chorea, HIV associated dementia, prion mediated neurodegeneration, epilepsy, stroke, cerebral ischemia, cerebral palsy, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, narcolepsy, glossopharyngeal neuralgia, mild cognitive decline, cognitive decline, spinal muscular atrophy, and cerebral malaria.

Cancer may be defined as comprising all sorts of cancers such as large intestine cancer, rectal cancer, breast cancer, lung cancer, non-small cell lung cancer, prostate cancer, esophagal cancer, stomach cancer, liver cancer, bile duct cancer, spleen cancer, kidney cancer, urinary bladder cancer, uterine cancer, ovarian cancer, cervical cancer, testicular cancer, thyroid cancer, pancreas cancer, brain tumor, blood tumor, basophil adenoma, prolactinoma, hyperprolactinemia, adenomas, endometrial cancer, colon cancer; chronic lymphocytic leukemia (CLL); and especially the metastatic spread of those cancers.

Especially, compounds of Formula (I) according to any one of embodiments 1) to 31), or pharmaceutically acceptable salts thereof, are suitable for the prevention or treatment of diseases selected from one, several or all of the following groups of diseases and disorders:
1) Autoimmune disorders selected from rheumatoid arthritis (RA); multiple sclerosis (MS); inflammatory bowel disease (IBD; comprising Crohn's disease and ulcerative colitis); systemic lupus erythematosus (SLE); psoriasis; lupus nephritis; and type I diabetes;
2) Inflammatory diseases selected from COPD; dry eye syndrome (comprising Sjögren's dry eye syndrome); myopathies (comprising inflammatory myopathies); and sarcoidosis;
3) Transplant rejection selected from graft-versus-host diseases;
4) Fibrosis selected from liver cirrhosis (comprising primary biliary cirrhosis (PBC) and autoimmune hepatitis); and
5) Neurodegenerative disorders selected from Guillain-Barré syndrome.

Preparation of Compounds of Formula (I)

A further aspect of the invention is a process for the preparation of compounds of Formula (I). Compounds according to Formula (I) of the present invention can be prepared from commercially available or well known starting materials according to the methods described in the experimental part; by analogous methods; or according to the general sequence of reactions outlined below, wherein $R^1$, $R^2$, $R^3$, $R^4$, $R^5$ and $R^6$ are as defined for Formula (I). Other abbreviations used herein are explicitly defined, or are as defined in the experimental section. In some instances the generic groups $R^1$, $R^2$, $R^3$, $R^4$, $R^5$ and $R^6$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

General Preparation Routes:

Preparation of the Compounds of Formula (I)

Scheme 1

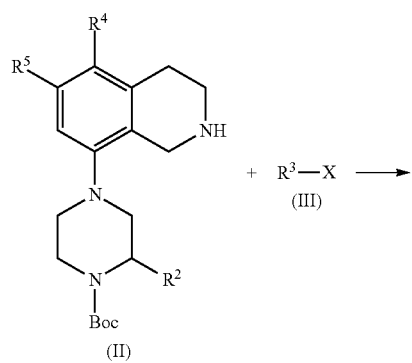

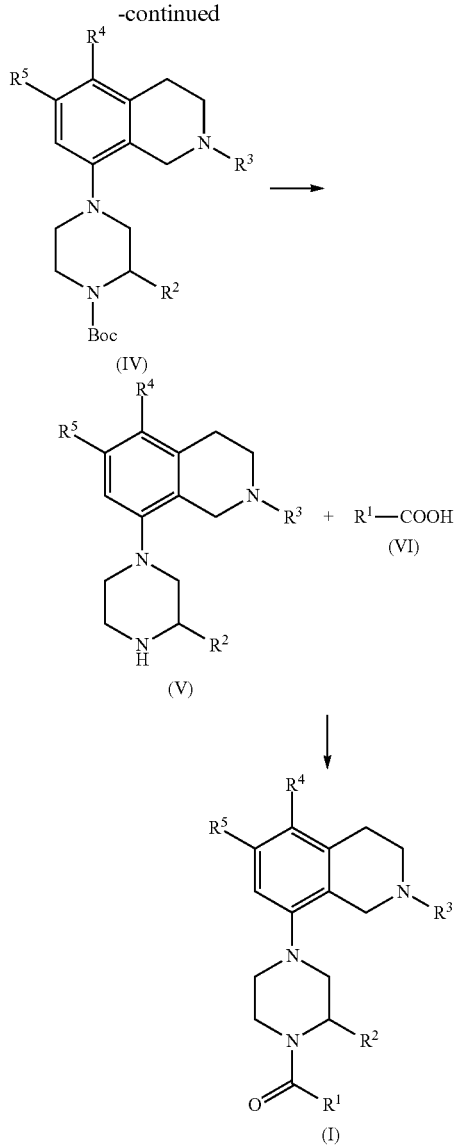

The compounds of formula (I) wherein $R^3$ represents aryl, heteraryl, or Cbz can be obtained following the synthetic pathway described in Scheme 1. A compound of formula (II) can be coupled to a compound of formula (III) wherein $R^3$ represents aryl or heteraryl and X represents chlorine, bromine or iodine, performing a Buchwald type reaction, using a catalyst such as $Pd(dba)_2$ or $Pd(OAc)_2$, in presence of a ligand such as DavePhos or RuPhos, in presence of a base such as KOtBu or NaOtBu, in toluene and heating at a temperature between 80° C. and 90° C. A compound of formula (II) can also be protected on the nitrogen atom with a Cbz group, using standard conditions known to one skilled in the art, like reacting with benzyl chloroformate in presence of TEA in DCM and at a temperature of about 0° C. The Boc protecting group of the intermediate of formula (IV) can be subsequently cleaved under standard acidic conditions, preferably using HCl in a suitable solvent such as EA, dioxane, $Et_2O$, MeOH, EtOH or a mixture thereof and at a temperature of about RT to give the compound of formula (V). Finally the compound of formula (I) can be prepared by coupling the compound of formula (V) with a carboxylic acid derivative of formula (VI) using standard peptide coupling methods such as HOBT, EDCI, DCC, HATU, HOAT, or a combination thereof, or a polymer supported form thereof, optionally in presence of a suitable base such as TEA, DIPEA or N-methylmorpholine and in a suitable solvent such as DCM, THF, DMF or a mixture thereof, preferably at a temperature of about RT.

Alternatively, the compounds of formula (I) wherein $R^3$ is different from Cbz can be prepared from compounds of formula (I) wherein $R^3$ represents Cbz following the route described in Scheme 2.

aromatic nucleophilic substitution type reaction with a compound of formula (III) wherein $R^3$ represents heteroaryl and X represents chlorine, in presence of a base such as TEA or DIPEA, in a suitable solvent such as MeCN and heating at a temperature of about 80° C. Furthermore, the compound of formula (VII) can be reacted with a carboxylic acid derivative of formula (III) wherein $R^3$ represents $R^6$-carbonyl and X represents —OH, using standard conditions for an amide coupling type reaction such as those already described for Scheme 1. In addition, the compound of formula (VII) can be reacted with a sulfonyl chloride derivative of formula (III) wherein $R^3$ represents aryl-($C_{1-2}$)alkyl-sulfonyl and X represents chlorine, in presence of a base such as DIPEA or TEA, in a solvent such as DCM, THF or DMF and at a temperature of about 0° C. Alternatively, the compound of formula (VII) can be submitted to an alkylation type reaction with a compound of formula (III) wherein $R^3$ represents aryl-($C_{1-2}$)alkyl and X represents chlorine, bromine or iodine, in presence of a base such as TEA or DIPEA, in a solvent such as DCM, THF, DMF or EtOH and at a temperature of about RT.

Compounds of formula (IV) wherein $R^4$ represents bromine, cyano or trifluoromethyl and $R^5$ represents hydrogen can be prepared by an alternative route starting from a compound of formula (IV) wherein $R^4$ and $R^5$ both represent hydrogen, as shown in Scheme 3.

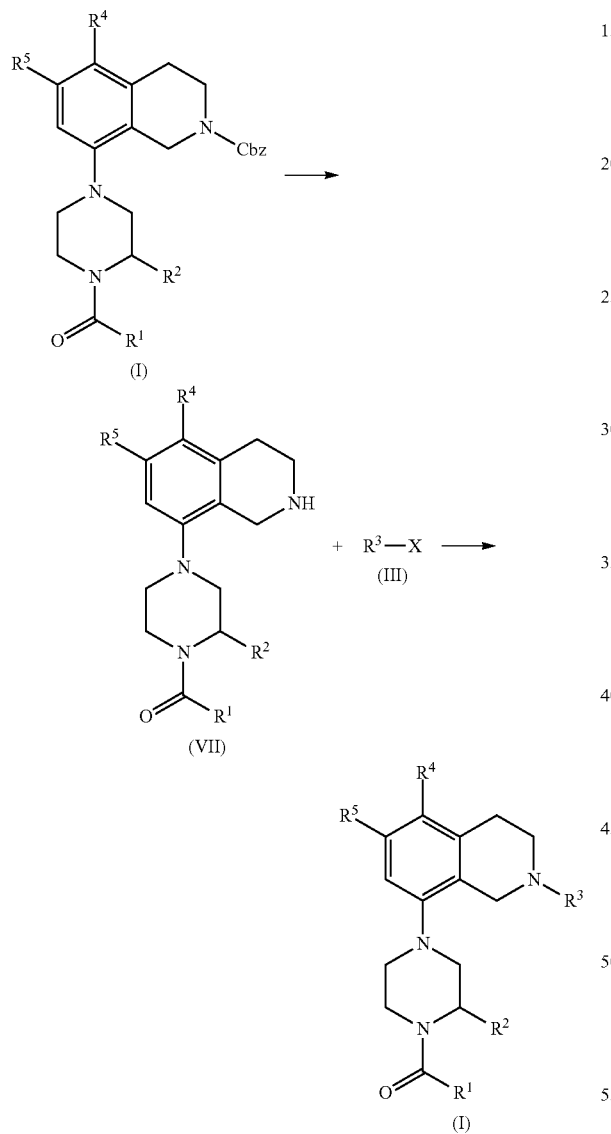

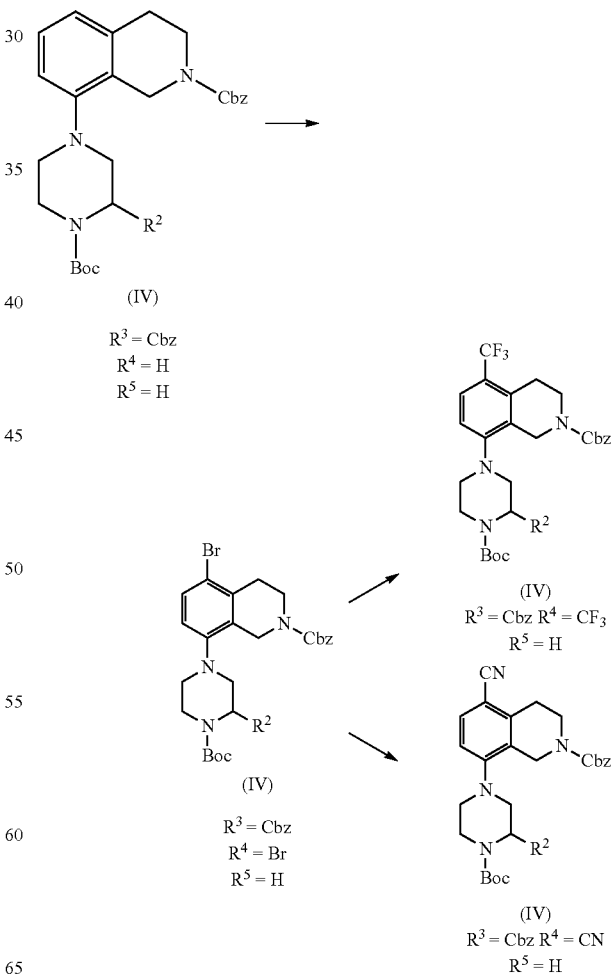

The compound of formula (I) wherein $R^3$ is Cbz can be treated with ammonium formate and Pd/C in refluxing MeOH. The resulting compound of formula (VII) can be submitted to a Buchwald type reaction with a compound of formula (III), using the conditions already described for Scheme 1. Alternative conditions for the Buchwald reaction can be $Pd_2(dba)_3$ as palladium source in presence of 2-(dicyclohexylphosphino)biphenyl as ligand, using NaOtBu as base, in DME and heating at a temperature of about 100° C. The compound of formula (VII) can also be engaged in an A compound of formula (IV) wherein $R^3$ represents Cbz and $R^4$ and $R^5$ both represent hydrogen can be brominated in para position to the piperazine ring using NBS in MeCN at a temperature of about RT to give a compound of formula (IV) wherein $R^3$ represents Cbz, $R^4$ represents bromine and $R^5$ represents hydrogen. Further, the compound of formula (IV) wherein $R^3$ represents Cbz, $R^4$ represents bromine and $R^5$ represents hydrogen can be transferred into a compound of formula (IV) wherein $R^3$ represents Cbz, $R^4$ represents trifluoromethyl or cyano and $R^5$ represents hydrogen. For instance, the bromine atom can be replaced by a boronic ester group, using standard conditions such as bis(pinacolato)diboron in presence of 1,1-bis(diphenylphosphino)ferrocene]-dichloropalladium(II), DCM complex and KOAc in dioxane and heating at a temperature of about 80° C. The boronic ester group can be subsequently converted to a trifluoromethyl group using CuI, 1,10-phenanthroline, 3,3-dimethyl-1-(trifluoromethyl)-1,2-benziodoxole and $K_2CO_3$ in DME and heating at a temperature of about 35° C. to give a compound of formula (IV) wherein $R^3$ represents Cbz, $R^4$ represents trifluoromethyl and $R^5$ represents hydrogen. Furthermore, the bromine atom of the compound of formula (IV) wherein $R^3$ represents Cbz, $R^4$ represents bromine and $R^5$ represents hydrogen can be replaced by a cyano group using standard conditions such as CuCN in NMP and heating at a temperature of about 130° C.

Preparation of the Compounds of Formula (II)

The compounds of formula (II) can be prepared following a procedure outlined in Scheme 4.

Scheme 4

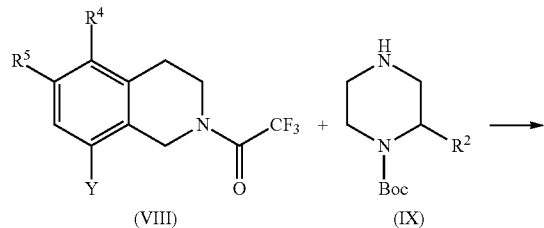

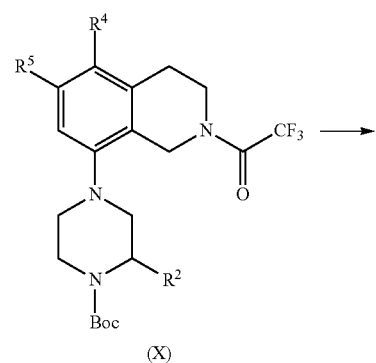

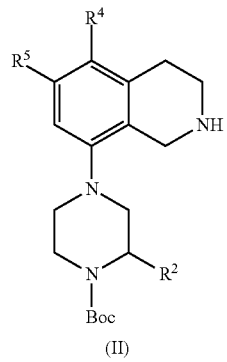

A compound of formula (VIII) wherein Y represents chlorine or bromine can be reacted with an amine derivative of formula (IX) in a Buchwald type reaction, using $Pd_2(dba)_3$ as catalyst, rac-2,2'-bis(diphenylphosphino)-1,1'-binaphthalene as ligand and $Cs_2CO_3$ as base, in toluene and heating at a temperature of about 120° C., to provide the compound of formula (X). The trifluoroacetyl protecting group of the compound of formula (X) can be cleaved using standard basic conditions such as $K_2CO_3$ in a mixture of EtOH and water and heating at a temperature of about 90° C.

Alternatively, the compounds of formula (II) wherein $R^4$ and $R^5$ both represent hydrogen can be prepared according to the procedure described in Scheme 5.

Scheme 5

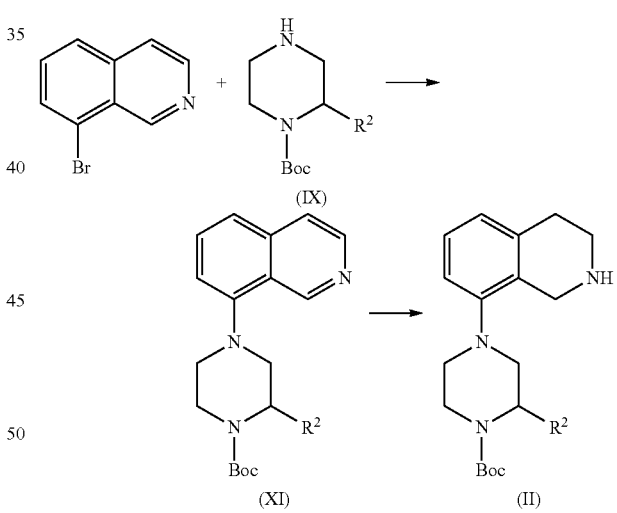

8-Bromoisoquinoline and an amine derivative of formula (IX) can be submitted to a Buchwald type reaction, using a catalyst such as $Pd_2(dba)_3$, in presence of a ligand such as rac-2,2'-bis(diphenylphosphino)-1,1'-binaphthalene, in presence of a base such as NaOtBu, in toluene and heating at a temperature of about 90° C. The resulting compound of formula (XI) can be reduced to the tetrahydroisoquinoline derivative of formula (II) using platinum(IV) oxide in a solvent such as isopropanol and under hydrogen pressure of about 6 bars.

Preparation of the Compounds of Formula (VII)

An alternative pathway to synthesize the compounds of formula (VII) is shown hereafter in Scheme 6.

Scheme 6

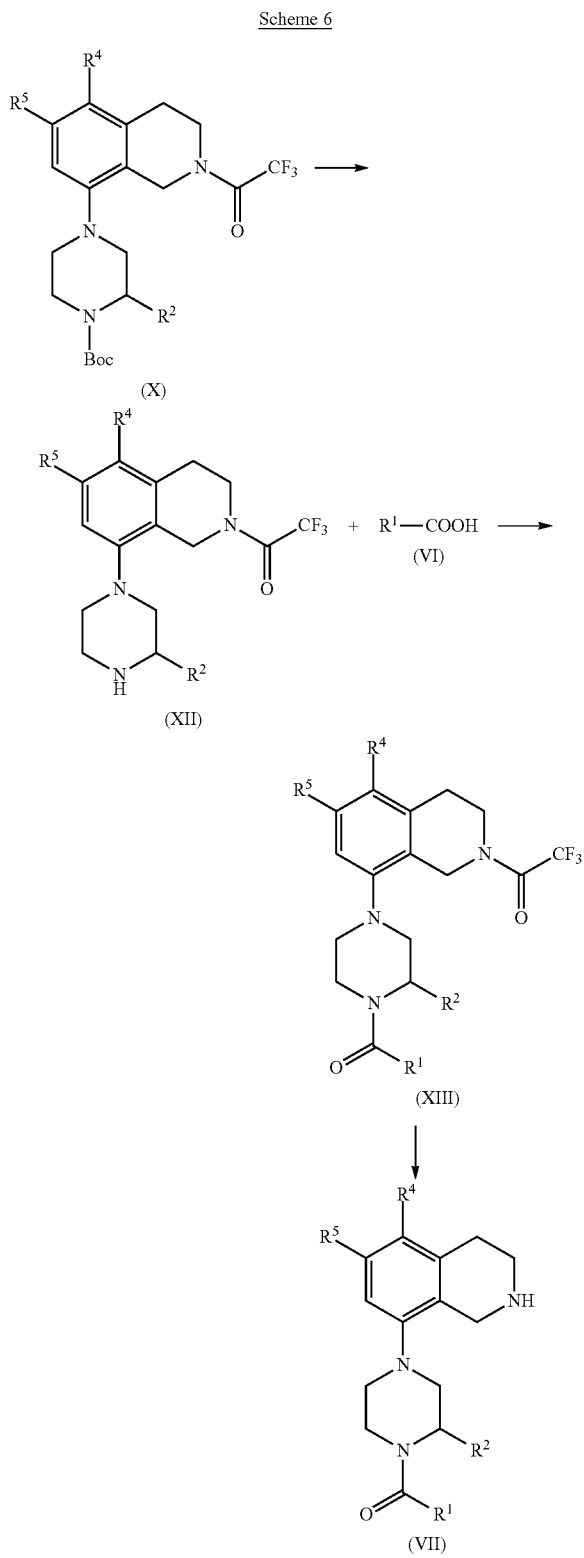

The compounds of formula (VII) can be obtained starting from a compound of formula (X) in three consecutive steps, namely Boc cleavage, followed by an amide coupling reaction with a carboxylic acid derivative of formula (VI) and finally by trifluoroacetyl removal using reaction conditions as described above.

Preparation of the Compounds of Formula (VIII)

The compounds of formula (VIII) can be prepared according to the synthetic routes described in Scheme 7.

The compounds of formula (VIII) wherein $R^4$ represents fluorine, $R^5$ represents hydrogen and Y represents bromine can be prepared starting from 8-bromo-5-fluoro-1,2,3,4-tetrahydro-isoquinoline hydrochloride (WO2013/093842). The amine function is protected as a trifluoroacetyl group using standard conditions, using trifluoroacetic anhydride in pyridine and cooling the reaction mixture at a temperature of about 0° C.

The compounds of formula (VIII) wherein $R^4$ and $R^5$ both represent fluorine and Y represents bromine can be prepared in two steps starting from commercially available 5,6-difluoro-1,2,3,4-tetrahydroisoquinoline. The amine function is protected as a trifluoroacetyl group as described above. The resulting intermediate is brominated in para-position to the $R^4$-group using bromine, in presence of a catalyst such as $FeCl_3$, in DCM and at a temperature from about 0° C. up to about RT.

The compounds of formula (VIII) wherein either $R^4$ or $R^5$ represents trifluoromethyl, the other of them represents hydrogen and Y represents chlorine can be prepared in three steps starting from the respective commercially available 2-(3-chloro-trifluoromethyl-phenyl)acetonitrile derivatives. The cyano group of the starting compound can be reduced to a aminomethyl group using $BH_3$-THF complex in THF at a temperature from about 0° C. up to about 75° C. The amine function is protected as a trifluoroacetyl group as described above. Finally the trifluoroacetamide derivative can be cyclized to give the compound of formula (VIII) by reaction with paraformaldehyde in a mixture of AcOH and $H_2SO_4$ and at a temperature of about RT. Other compounds of formula (VIII) wherein Y represents chlorine or bromine may be prepared in analogy.

Scheme 7

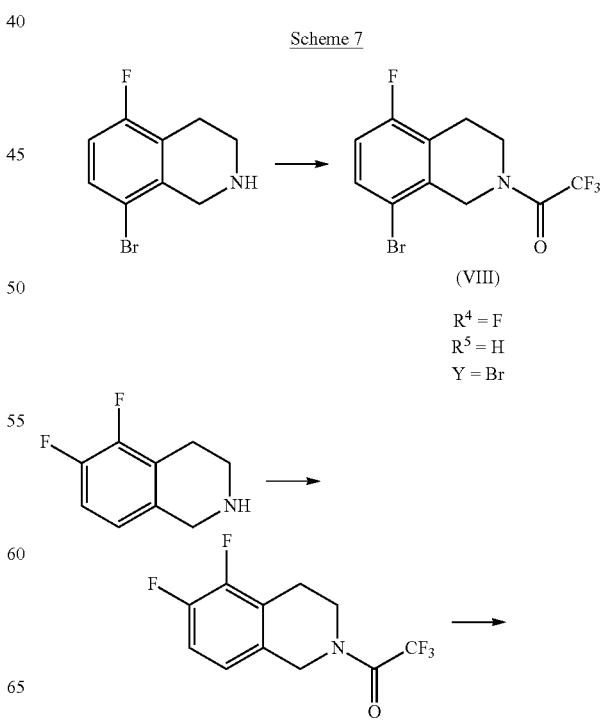

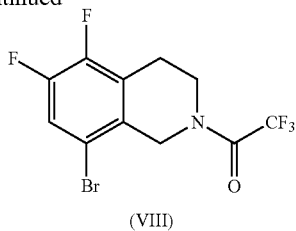

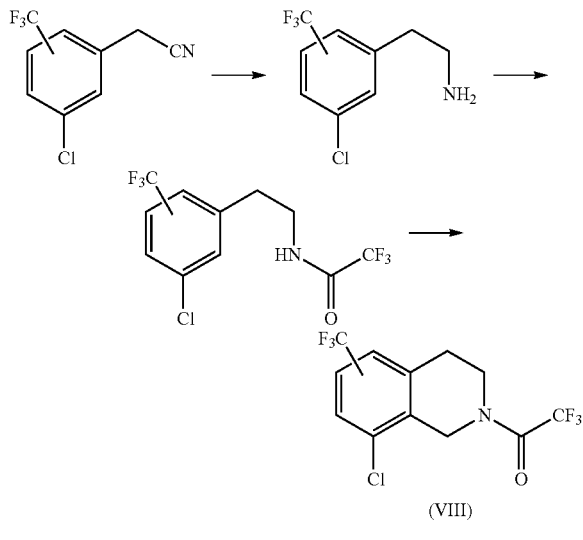

Compounds of formula (VI) are commercially available or can be synthesized according to the procedures given in WO2013/114332 or in the experimental part.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Daicel ChiralPak IC (5 m) column. Typical conditions of chiral HPLC are an isocratic mixture of eluent A (EtOH or iPrOH, in presence or absence of an amine such as TEA, DEA) and eluent B (hexane or MeCN), at a flow rate of 0.8 to 16 mL/min.

EXPERIMENTAL SECTION

Abbrevations (as Used Herein and in the Description Above)

Ac acetyl
aq. aqueous
BINAP rac-2,2'-bis(diphenylphosphino)-1,1'-binaphthalene
Boc tert.-butyloxycarbonyl
Brine saturated aqueous NaCl solution
BSA Bovine serum albumine
Bu butyl (such as in tBuLi=tert.-BuLi=tertiary butyl lithium)
Cbz benzyloxycarbonyl
CC column chromatography on silica gel
CHO Chinese hamster ovary
CV column volume
d doublet
DavePhos 2-dicyclohexylphosphino-2'-(N,N-dimethyl-amino)biphenyl
dba dibenzylideneacetone
DCC 1,3-dicyclohexylcarbodiimide
DCM dichloromethane
DEA diethylamine
DIPEA N-ethyldiisopropylamine
DME 1,2-dimethoxyethane
DMF dimethylformamide
DMSO dimethylsulfoxide
EA ethyl acetate
EDCI N-(3-dimethylaminopropyl)-N'-ethylcarbodiimide (as HCl salt)
Eq equivalent
Et ethyl
EtOH ethanol
FBS fetal bovine serum
FLIPR Fluorescent imaging plate reader
Fluo-4-AM 2-{[2-(2-{5-[bis(carboxymethyl)amino]-2-methylphenoxy}ethoxy)-4-(2,7-difluoro-6-hydroxy-3-oxo-3H-xanthen-9-yl)phenyl](carboxymethyl)amino}acetic acid
G418 (2R,3S,4R,5R,6S)-5-amino-6-[(1R,2S,3S,4R,6S)-4,6-diamino-3-[(2R,3R,4R,5R)-3,5-dihydroxy-5-methyl-4-methylaminooxan-2-yl]oxy-2-hydroxycyclohexyl]oxy-2-(1-hydroxyethyl)oxane-3,4-diol
h hour(s)
HATU 2-(7-Aza-1H-benzotriazole-1-yl)-1,1,3,3-tetramethyluronium hexafluorophosphate
HBSS Hank's balanced salt solution
HEPES 4-(2-hydroxyethyl)-piperazine-1-ethanesulfonic acid
Hept heptane
HOAT 7-aza-1-hydroxybenzotriazole
HOBT 1-hydroxybenzotriazole, hydrate
HPLC high performance liquid chromatography
iPr isopropyl
LC liquid chromatography
m multiplet
M molarity [mol L$^{-1}$]
Me methyl
MS mass spectrometry
min minute(s)
N normality
NaOtBu sodium tert. (tertiary) butoxide
NBS N-bromo-succinimide
NMP 1-methyl-2-pyrrolidone
org. organic
Pd/C palladium on carbon
Ph phenyl
PL- Polymer supported
PL-HCO$_3$ StratoSpheres™ Solid Phase Extraction cartridges containing a HCO3⁻ quaternary amine salt
q quadruplet
RT room temperature
RuPhos 2-dicyclohexylphosphino-2',6'-diisopropoxybiphenyl
s singulet
Sat. Saturated
Si-DCC Silicabond DCC
t triplet
TEA triethylamine
TFA trifluoroacetic acid
THF tetrahydrofuran
t$_R$ retention time I. Chemistry The following examples illustrate the preparation of biologically active compounds of the invention but do not at all limit the scope thereof.

General:

All temperatures are stated in degrees Celsius (° C.). Unless otherwise indicated, the reactions take place at RT under an argon atmosphere and are run in a flame dried round-bottomed flask equipped with a magnetic stir bar.

Characterization Methods Used:

The LC-MS retention times have been obtained using the following elution conditions:

A) LC-MS (A):

Acquity UPLC CSH C18 1.7 μm 2.1×50 mm ID column from Waters, thermostated in the Acquity UPLC Column Manager (60° C.) was used. The two elution solvents were as follows: solvent A=water+0.05% formic acid; solvent B=acetonitrile+0.045% formic acid. The eluent flow rate was 1 mL/min and the characteristics of the eluting mixture proportion in function of the time t from start of the elution are summarized in the table below (a linear gradient being used between two consecutive time points):

| t (min)       | 0  | 1.4 | 1.8 | 1.9 | 2.0 |
|---------------|----|-----|-----|-----|-----|
| Solvent A (%) | 98 | 5   | 2   | 2   | 98  |
| Solvent B (%) | 2  | 95  | 98  | 98  | 2   |

B) LC-MS (B):

Zorbax SB-Aq, 3.5 m, 4.6×50 mm column thermostated at 40° C. The two elution solvents were as follows: solvent A=water+0.04% TFA; solvent B=acetonitrile. The eluent flow rate was 4.5 mL/min and the characteristics of the eluting mixture proportion in function of the time t from start of the elution are summarized in the table below (a linear gradient being used between two consecutive time points):

| t (min)       | 0  | 1.0 | 1.45 | 1.55 |
|---------------|----|-----|------|------|
| Solvent A (%) | 95 | 5   | 5    | 95   |
| Solvent B (%) | 5  | 95  | 95   | 5    |

C) LC-MS (C):

Waters XBridge C18, 5 m, 4.6×50 mm column not thermostated. The two elution solvents were as follows: solvent A=water+0.1% NH$_4$OH; solvent B=acetonitrile. The eluent flow rate was 4.5 mL/min and the characteristics of the eluting mixture proportion in function of the time t from start of the elution are summarized in the table below (a linear gradient being used between two consecutive time points):

| t (min)       | 0  | 0.75 | 1.45 | 1.55 |
|---------------|----|------|------|------|
| Solvent A (%) | 95 | 5    | 5    | 95   |
| Solvent B (%) | 5  | 95   | 95   | 5    |

D) LC-MS (D):

Accucore C18, 2.6 μm, 2.1×50 mm column thermostated at 40° C. The two elution solvents were as follows: solvent A=acetonitrile; solvent B=water+0.05% NH$_4$OH+2% acetonitrile. The eluent flow rate was 1.2 mL/min and the characteristics of the eluting mixture proportion in function of the time t from start of the elution are summarized in the table below (a linear gradient being used between two consecutive time points):

| t (min)       | 0  | 2.1 | 2.4 | 2.45 | 2.60 |
|---------------|----|-----|-----|------|------|
| Solvent A (%) | 5  | 95  | 95  | 5    | 5    |
| Solvent B (%) | 95 | 5   | 5   | 95   | 95   |

E) LC-MS (E):

Accucore C18, 2.6 m, 2.1×50 mm column thermostated at 40° C. The two elution solvents were as follows: solvent A=acetonitrile; solvent B=water+0.05% NH$_4$OH+2% acetonitrile. The eluent flow rate was 1.2 mL/min and the characteristics of the eluting mixture proportion in function of the time t from start of the elution are summarized in the table below (a linear gradient being used between two consecutive time points):

| t (min)       | 0  | 1.2 | 1.5 | 1.55 | 1.7 |
|---------------|----|-----|-----|------|-----|
| Solvent A (%) | 5  | 95  | 95  | 5    | 5   |
| Solvent B (%) | 95 | 5   | 5   | 95   | 95  |

Preparative LC-MS Methods Used:

The purifications by preparative LC-MS have been performed using the conditions described hereafter.

I) Preparative LC-MS (I):

A X-Bridge column (Waters Prep C18, 10 μm, 30×75 mm) was used. The two elution solvents were as follows: solvent A=water+0.5% NH$_4$OH; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min)       | 0  | 3.5 | 6.0 | 6.2 | 6.6 |
|---------------|----|-----|-----|-----|-----|
| Solvent A (%) | 70 | 5   | 5   | 70  | 70  |
| Solvent B (%) | 30 | 95  | 95  | 30  | 30  |

II) Preparative LC-MS (II):

A Gemini column (Phenomenex NX 10 m, 30×1000 mm) was used. The two elution solvents were as follows: solvent A=water+0.5% NH$_4$OH; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 7.8 | 9.2 | 9.5 | 10.0 |
|---------------|----|-----|-----|-----|-----|------|
| Solvent A (%) | 60 | 60  | 5   | 5   | 60  | 60   |
| Solvent B (%) | 40 | 40  | 95  | 95  | 40  | 40   |

III) Preparative LC-MS (III):

A X-Bridge column (Waters C18, 10 μm, 30×75 mm) was used. The two elution solvents were as follows: solvent A=water+0.5% NH$_4$OH; solvent B=acetonitrile. The eluent flow rate was 75 mL/min and the characteristics of the eluting mixture proportion in function of the time t from start of the elution are summarized in the tables below (a linear gradient being used between two consecutive time points):

| t (min)       | 0  | 4.0 | 6.0 | 6.2 | 6.6 |
|---------------|----|-----|-----|-----|-----|
| Solvent A (%) | 80 | 5   | 5   | 80  | 80  |
| Solvent B (%) | 20 | 95  | 95  | 20  | 20  |

IV) Preparative LC-MS (IV):

A XBridge column (Waters Prep C18 5 μm, 19×50 mm) was used. The two elution solvents were as follows: solvent A=water+0.1% formic acid; solvent B=acetonitrile+0.1% formic acid. The eluent flow rate was 40 mL/min and the characteristics of the eluting mixture proportion in function of the time t from start of the elution are summarized in the tables below (a linear gradient being used between two consecutive time points):

| t (min)       | 0  | 0.2 | 0.3 | 3.2 | 3.3 | 4.3 | 4.4 |
|---------------|----|-----|-----|-----|-----|-----|-----|
| Solvent A (%) | 60 | 60  | 50  | 20  | 95  | 95  | 5   |
| Solvent B (%) | 40 | 40  | 50  | 80  | 5   | 5   | 95  |

V) Preparative LC-MS (V):

A XBridge column (Waters Prep C18 5 μm, 19×50 mm) was used. The two elution solvents were as follows: solvent A=water+0.1% HCOOH; solvent B=acetonitrile+0.1% HCOOH. The eluent flow rate was 40 mL/min and the characteristics of the eluting mixture proportion in function of the time t from start of the elution are summarized in the tables below (a linear gradient being used between two consecutive time points):

| t (min)       | 0  | 0.2 | 0.3 | 3.2 | 3.3 | 4.3 | 4.4 |
|---------------|----|-----|-----|-----|-----|-----|-----|
| Solvent A (%) | 90 | 90  | 80  | 50  | 95  | 95  | 5   |
| Solvent B (%) | 10 | 10  | 20  | 50  | 5   | 5   | 95  |

VI) Preparative LC-MS (VI):

A Waters column (XBridge Prep C 18 10 μm, 19×50 mm) was used. The two elution solvents were as follows: solvent A=water+0.1% NH$_4$OH; solvent B=acetonitrile+0.1% NH$_4$OH. The eluent flow rate was 40 mL/min and the characteristics of the eluting mixture proportion in function of the time t from start of the elution are summarized in the tables below (a linear gradient being used between two consecutive time points):

| t (min)       | 0.0 | 0.3 | 4.2 | 4.3 | 5.3 | 6.0 |
|---------------|-----|-----|-----|-----|-----|-----|
| Solvent A (%) | 95  | 35  | 5   | 5   | 5   | 95  |
| Solvent B (%) | 5   | 65  | 95  | 95  | 95  | 5   |

VII) Preparative LC-MS (VII):

A Waters column (XBridge Prep C18, 10 μm, 19×50 mm) was used. The two elution solvents were as follows: solvent A=water+0.1% NH$_4$OH; solvent B=acetonitrile+0.1% NH$_4$OH. The eluent flow rate was 40 mL/min and the characteristics of the eluting mixture proportion in function of the time t from start of the elution are summarized in the tables below (a linear gradient being used between two consecutive time points):

| t (min)       | 0  | 0.3 | 4.2 | 4.3 | 5.3 | 6.0 |
|---------------|----|-----|-----|-----|-----|-----|
| Solvent A (%) | 75 | 50  | 20  | 5   | 5   | 95  |
| Solvent B (%) | 25 | 50  | 80  | 95  | 95  | 5   |

VIII) Preparative LC-MS (VIII):

A Gemini column (Phenomenex NX 10 jm, 30×1000 mm) was used. The two elution solvents were as follows: solvent A=water+0.5% NH$_4$OH; solvent B=acetonitrile. The eluent flow rate was 100 mL/min and the characteristics of the eluting mixture proportion in function of the time t from start of the elution are summarized in the tables below (a linear gradient being used between two consecutive time points):

| t (min)       | 0  | 0.6 | 7.8 | 9.2 | 9.5 | 10 |
|---------------|----|-----|-----|-----|-----|----|
| Solvent A (%) | 80 | 80  | 5   | 5   | 80  | 80 |
| Solvent B (%) | 20 | 20  | 95  | 95  | 20  | 20 |

Preparative Chiral HPLC Methods Used:

The purifications by preparative chiral HPLC have been performed using the conditions described hereafter.

I) Preparative chiral HPLC (I):

A ChiralPak IC column (5 m, 20×250 mm) was used. The elution solvent was MeCN/EtOH/DEA 50/50/0.1, run for 10 min and at a flow rate of 16 mL/min.

Example 1: 2-(3,5-Dimethyl-pyrazol-1-yl)-1-{(R)-2-methyl-4-[2-(5-pyrazol-1-ylmethyl-thiazol-2-yl)-5-trifluoromethyl-1,2,3,4-tetrahydro-isoquinolin-8-yl]-piperazin-1-yl}-ethanone 1.1.
2-(5-Chloro-2-trifluoromethyl-phenyl)-ethylamine To an ice cold solution of 2-(5-chloro-2-(trifluoromethyl)phenyl)acetonitrile (5 g) in THF (250 mL) was added slowly a solution of boran-tetrahydrofuran-complex (89 mL, 1M). The resulting solution was stirred at 0° C. for 5 min and heated at 75° C. for 1 h30. The reaction mixture was cooled down in an ice bath and 2N HCl was added. The stirring was continued at 0° C. for 10 min. To the resulting clear solution was added Na$_2$CO$_3$ until pH 8 and the mixture was extracted with EA. The aq. layers were extracted with EA, the combined org. layers were dried (Na$_2$SO$_4$) and evaporated in vacuo to afford 5.02 g of yellow oil. LC-MS (B): $t_R$=0.58 min; [M+H]$^+$: 224.10.

1.2. N-[2-(5-Chloro-2-trifluoromethyl-phenyl)-ethyl]-2,2,2-trifluoro-acetamide

To a solution of intermediate 1.1 (5 g) in DCM (56 mL) at 0° C. was added pyridine (8.98 mL) followed by trifluoroacetic anhydride (4.7 mL). The reaction mixture was stirred at 0° C. for 1 h and quenched by addition of ice/water. The resulting mixture was extracted with DCM. The org. layers were washed with 1M HCl, brine, were dried (Na$_2$SO$_4$) and evaporated in vacuo to give 6.43 g of rosa solid. LC-MS (B): $t_R$=0.93 min. $^1$H-NMR (CDCl$_3$): 7.63 (d, 1H, 9.0 Hz); 7.38 (m, 2H); 6.42 (s, 1H); 3.65 (q, 2H, 7.0 Hz and 14.1 Hz); 3.08 (t, 2H, 7.3 Hz).

1.3. 1-(8-Chloro-5-trifluoromethyl-3,4-dihydro-1H-isoquinolin-2-yl)-2,2,2-trifluoro-ethanone To a flask charged with paraformaldehyde (95%, 1.27 g) and intermediate 1.2 (6.43 g) was added a solution of AcOH (37 mL) and H$_2$SO$_4$ (56 mL). The mixture was stirred at RT for 1 h and cooled down to 0° C. Ice/water was added and the resulting mixture was extracted with EA. The org. layers were washed with sat. NaHCO$_3$, dried (Na$_2$SO$_4$) and evaporated in vacuo to afford 6.1 g of yellow oil. LC-MS (B): t$_R$=0.98 min. $^1$H-NMR (CDCl$_3$): 7.57 (d, 1H, 8.5 Hz); 7.44 (d, 1H, 8.5 Hz); 4.87 (s, 1.3H); 4.85 (s, 0.7H); 3.91 (dt, 2H, 17.8 Hz, 6.0 Hz); 3.15 (m, 2H).

1.4. (R)-2-Methyl-4-[2-(2,2,2-trifluoro-acetyl)-5-trifluoromethyl-1,2,3,4-tetrahydro-isoquinolin-8-yl]-piperazine-1-carboxylic acid tert-butyl ester To a solution of intermediate 1.3 (6.1 g) in toluene (122 mL) was added (R)-1-N-Boc-2-methylpiperazine (5.68 g), BINAP (145 mg) and Cs$_2$CO$_3$ (8.87 g). The mixture was degased under vacuum and backfilled with argon three times. Tris(dibenzylideneaceton)-dipalladium(0) (421 mg) was added and degasing was repeated. The reaction mixture was stirred under argon at 120° C. overnight. After cooling down, aq. K$_2$CO$_3$ (20%) and EA were added. The phases were separated, the org. layer was dried (Na$_2$SO$_4$) and evaporated in vacuo. CC (Biotage, SNAP 100 g cartridge, solvent A: Hept; solvent B: EA; gradient in % B: 12 for 4CV, 12 to 74 over 7CV) afforded 5.84 g of yellow powder. LC-MS (B): t$_R$=1.07 min; [M+H]$^+$: 496.21.

1.5. 2,2,2-Trifluoro-1-[8-((R)-3-methyl-piperazin-1-yl)-5-trifluoromethyl-3,4-dihydro-1H-isoquinolin-2-yl]-ethanone, hydrochloride salt A mixture of intermediate 1.4 (3.69 g) in HCl (4M in dioxane, 37 mL) was stirred for 1.5 h. The solvent was removed under reduced pressure to afford 3.22 g of beige solid. LC-MS (B): t$_R$=0.71 min; [M+H]$^+$: 396.24.

1.6. 1-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-2,2,2-trifluoro-ethanone A mixture of intermediate 1.5 (3.21 g), (3,5-dimethyl-1H-pyrazol-1-yl)acetic acid (1.26 g) and HATU (3.12 g) in DIPEA (3.95 mL) and DCM (59 mL) was stirred at RT overnight. NaHCO$_3$ and DCM were added, the phases were separated and the org. layer was evaporated in vacuo. The crude was purified by CC (Biotage, SNAP 100 g cartridge, solvent A: Hept; solvent B: EA; gradient in % B: 25 for 2CV, 25 to 100 over 5CV, 100 for 6CV) to afford 3.9 g of yellow solid. LC-MS (B): t$_R$=0.92 min; [M+H]$^+$: 532.24.

1.7. 2-(3, 5-Dimethyl-pyrazol-1-yl)-1-[(R)-2-methyl-4-(5-trifluoromethyl-1,2,3,4-tetrahydro-isoquinolin-8-yl)-piperazin-1-yl]-ethanone A mixture of intermediate 1.6 (2.13 g) and K$_2$CO$_3$ (1.11 g) in EtOH/water (39 mL/39 mL) was stirred for 0.5 h at 90° C. EtOH was removed under vacuo and the remaining aq. mixture was extracted with EA. The combined org. layers were dried (Na$_2$SO$_4$) and evaporated off to afford 1.66 g of yellow foam. LC-MS (B): t$_R$=0.63 min; [M+H]$^+$: 436.25.

1.8. 2-(3, 5-Dimethyl-pyrazol-1-yl)-1-{(R)-2-methyl-4-[2-(5-pyrazol-1-ylmethyl-thiazol-2-yl)-5-trifluoromethyl-1,2, 3, 4-tetrahydro-isoquinolin-8-yl]-piperazin-1-yl}-ethanone To a vial charged with 2-chloro-5-(1H-pyrazol-1-ylmethyl)-1,3-thiazole (40 mg) under argon was added a solution of intermediate 1.7 (43.5 mg) in degased toluene (1 mL), bis(dibenzylideneacetone)palladium (0) (3.45 mg), DavePhos (7.87 mg) and potassium tert-butoxide (34.7 mg). The mixture was degased and heated at 80° C. under argon overnight. Toluene was removed in vacuo and the residue was taken up in DCM/water. The phases were separated and the org. layer was evaporated off. The crude was dissolved in DMF (0.6 mL) and purified by preparative LC-MS (I) to afford 11 mg of beige powder. LC-MS (A): t$_R$=1.13 min; [M+H]$^+$: 599.4.

Example 2 to Example 15 were synthesized starting from the appropriate chloro or bromo heteroaryl derivative and following the procedure described in Example 1, step 1.8. LC-MS data of Example 2 to Example 15 are listed in the table below. The LC-MS conditions used were LC-MS (A) for Examples 2 to 6 and 8 to 15. The LC-MS conditions used were LC-MS (C) for Example 7.

| Example No | Name | t$_R$ | [M + H]$^+$ |
|---|---|---|---|
| 2 | 2-(3,5-Dimethyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone | 1.37 | 587.4 |
| 3 | 2-(3,5-Dimethyl-pyrazol-1-yl)-1-{(R)-4-[2-(4-ethyl-thiazol-2-yl)-5-trifluoromethyl-1,2,3,4-tetrahydro-isoquinolin-8-yl]-2-methyl-piperazin-1-yl}-ethanone | 1.21 | 547.4 |
| 4 | 1-{(R)-4-[2-(4-tert.-Butyl-thiazol-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone | 1.5 | 575.4 |
| 5 | 2-(3,5-Dimethyl-pyrazol-1-yl)-1-{(R)-2-methyl-4-[2-(4-pyridin-2-yl-thiazol-2-yl)-5-trifluoromethyl-1,2,3,4-tetrahydro-isoquinolin-8-yl]-piperazin-1-yl}-ethanone | 1.19 | 596.4 |
| 6 | 1-{(R)-4-[2-(5-Chloro-thiazol-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone | 1.36 | 553.3 |
| 7 | 2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-thiazole-4-carbonitrile | 0.96 | 544.0 |
| 8 | 2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-thiazole-5-carbonitrile | 1.24 | 544.4 |
| 9 | 2-(3,5-Dimethyl-pyrazol-1-yl)-1-{(R)-2-methyl-4-[2-(6-methyl-benzothiazol-2-yl)-5-trifluoromethyl-1,2,3,4-tetrahydro-isoquinolin-8-yl]-piperazin-1-yl}-ethanone | 1.4 | 583.4 |

-continued

| Example No | Name | $t_R$ | $[M + H]^+$ |
|---|---|---|---|
| 10 | 2-(3,5-Dimethyl-pyrazol-1-yl)-1-{(R)-4-[2-(6-fluoro-benzothiazol-2-yl)-5-trifluoromethyl-1,2,3,4-tetrahydro-isoquinolin-8-yl]-2-methyl-piperazin-1-yl}-ethanone | 1.38 | 587.4 |
| 11 | 2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-benzothiazole-6-carbonitrile | 1.32 | 594.4 |
| 12 | 1-[(R)-4-(2-Benzooxazol-2-yl-5-trifluoromethyl-1,2,3,4-tetrahydro-isoquinolin-8-yl)-2-methyl-piperazin-1-yl]-2-(3,5-dimethyl-pyrazol-1-yl)-ethanone | 1.29 | 553.4 |
| 13 | 1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone | 1.2 | 557.4 |
| 14 | 1-{(R)-4-[2-(5-Bromo-pyrimidin-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone | 1.42 | 592.3 |
| 15 | 1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone | 1.22 | 554.4 |

Example 16: 2-Imidazo[4,5-b]pyridin-3-yl-1-[(R)-2-methyl-4-(2-phenyl-5-trifluoromethyl-1,2,3,4-tetrahydro-isoquinolin-8-yl)-piperazin-1-yl]-ethanone 16.1. (R)-2-Methyl-4-(5-trifluoromethyl-1,2,3,4-tetrahydro-isoquinolin-8-yl)-piperazine-1-carboxylic acid tert-butyl ester This compound was prepared using a method analogous to that of Example 1 step 1.7, intermediate 1.4 replacing intermediate 1.6. LC-MS (B): $t_R$=0.74 min; [M+H]$^+$: 400.34.

16.2. (R)-2-Methyl-4-(2-phenyl-5-trifluoromethyl-1,2,3,4-tetrahydro-isoquinolin-8-yl)-piperazine-1-carboxylic acid tert-butyl ester This compound was prepared using a method analogous to that of Example 1 step 1.8, intermediate 16.1 replacing intermediate 1.7 and iodobenzene replacing 2-chloro-5-(1H-pyrazol-1-ylmethyl)-1,3-thiazole. The compound was however purified by CC (Biotage, SNAP 10 g cartridge, solvent A: Hept; solvent B: EA; gradient in % B: 12 for 4CV, 12 to 100 over 10CV, 100 for 2CV). LC-MS (B): $t_R$=1.11 min; [M+H]$^+$: 476.24.

16.3. 8-((R)-3-Methyl-piperazin-1-yl)-2-phenyl-5-trifluoromethyl-1,2,3,4-tetrahydro-isoquinolin, hydrochloride salt This compound was prepared using a method analogous to that of Example 1 step 1.5, intermediate 16.2 replacing intermediate 1.4. LC-MS (B): $t_R$=0.75 min; [M+H]$^+$: 376.31.

16.4. 2-Imidazo[4,5-b]pyridin-3-yl-1-[(R)-2-methyl-4-(2-phenyl-5-trifluoromethyl-1,2,3,4-tetrahydro-isoquinolin-8-yl)-piperazin-1-yl]-ethanone This compound was prepared using a method analogous to that of Example 1 step 1.6, intermediate 16.3 replacing intermediate 1.5 and imidazo[4,5-b]pyridin-3-yl-acetic acid replacing (3,5-dimethyl-1H-pyrazol-1-yl)acetic acid. The compound was however purified by preparative LC-MS (II). LC-MS (A): $t_R$=1.27 min; [M+H]$^+$: 535.3.

Example 17: 2-Imidazo[4,5-b]pyridin-3-yl-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone This compound was prepared in three steps using a method analogous to that of Example 16 step 16.2 to 16.4, 5-bromo-2-methoxypyrimidine replacing iodobenzene in step 16.2. LC-MS (A): $t_R$=1.07 min; [M+H]$^+$: 567.4.

Example 18: 2-Imidazo[4,5-b]pyridin-3-yl-1-{(R)-4-[2-(3-methoxy-phenyl)-5-trifluoromethyl-1,2,3,4-tetrahydro-isoquinolin-8-yl]-2-methyl-piperazin-1-yl}-ethanone This compound was prepared in three steps using a method analogous to that of Example 16 step 16.2 to 16.4, 3-bromoanisole replacing iodobenzene in step 16.2. LC-MS (A): $t_R$=1.26 min; [M+H]$^+$: 565.4.

Example 19: 1-{(R)-4-[2-(4,6-Dimethoxy-[1,3,5]triazin-2-yl)-5-trifluoromethyl-1,2,3,4-tetrahydro-isoquinolin-8-yl]-2-methyl-piperazin-1-yl}-2-imidazo[4,5-b]pyridin-3-yl-ethanone This compound was prepared in three steps using a method analogous to that of Example 16 step 16.2 to 16.4, 2-chloro-4,6-dimethoxy-1,3,5-triazine replacing iodobenzene in step 16.2. LC-MS (A): $t_R$=1.16 min; [M+H]$^+$: 598.4.

Example 20: 1-{(R)-4-[2-(2-Ethoxy-pyrimidin-5-yl)-5-trifluoromethyl-1,2,3,4-tetrahydro-isoquinolin-8-yl]-2-methyl-piperazin-1-yl}-2-imidazo[4,5-b]pyridin-3-yl-ethanone This compound was prepared in three steps using a method analogous to that of Example 16 step 16.2 to 16.4, 5-bromo-2-ethoxypyrimidine replacing iodobenzene in step 16.2. LC-MS (A): $t_R$=1.13 min; [M+H]$^+$: 581.4.

Example 21: 1-{(R)-4-[2-(4-Chloro-phenyl)-5-trifluoromethyl-1,2,3,4-tetrahydro-isoquinolin-8-yl]-2-methyl-piperazin-1-yl}-2-imidazo[4,5-b]pyridin-3-yl-ethanone This compound was prepared in three steps using a method analogous to that of Example 16 step 16.2 to 16.4, 1,4-dichlorobenzene replacing iodobenzene in step 16.2. LC-MS (A): $t_R$=1.35 min; [M+H]$^+$: 569.4.

Example 22: 2-Imidazo[4,5-b]pyridin-3-yl-1-{(R)-2-methyl-4-[2-(2-propyl-pyrimidin-5-yl)-5-trifluoromethyl-1,2,3,4-tetrahydro-isoquinolin-8-yl]-piperazin-1-yl}-ethanone This compound was prepared in three steps using a method analogous to that of Example 16 step 16.2 to 16.4, 5-bromo-2-(n-propyl)pyrimidine replacing iodobenzene in step 16.2. LC-MS (A): $t_R$=1.13 min; [M+H]$^+$: 579.4.

Example 23: 2-(3,5-Dimethyl-[1,2,4]triazol-1-yl)-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone 23.1. (R)-4-[2-(2-Methoxy-pyrimidin-5-yl)-5-trifluoromethyl-1,2,3,4-tetrahydro-isoquinolin-8-yl]-2-methyl-piperazine-1-carboxylic acid tert-butyl ester This compound was prepared using a method analogous to that of Example 1 step 1.8, intermediate 16.1 replacing intermediate 1.7 and 5-bromo-2-methoxypyrimidine replacing 2-chloro-5-(1H-pyrazol-1-ylmethyl)-1,3-thiazole. It was nevertheless necessary to add more equivalents of base, catalyst and ligand to drive the reaction forward. The crude was purified by CC (solvent A: Hept; solvent B: EA; gradient in % B: 12 for 4CV, 12 to 100 over 10CV, 100 for 2CV). LC-MS (B): $t_R$=1.08 min; [M+H]$^+$: 508.26.

23.2. 2-(2-Methoxy-pyrimidin-5-yl)-8-((R)-3-methyl-piperazin-1-yl)-5-trifluoromethyl-1,2,3,4-tetrahydro-isoquinoline A solution of intermediate 23.1 (660 mg) in HCl (6.6 mL, 4M in dioxane) and MeOH (2.2 mL) was stirred at RT for 1.5 h. The solvent was removed under vacuo. The crude was suspended in MeCN/water, the suspension was filtered off and the resulting solution was purified by preparative LC-MS (III) to afford 170 mg of yellow powder. LC-MS (B): $t_R$=0.69 min; [M+H]$^+$: 408.36.

23.3. 2-(3,5-Dimethyl-[1, 2, 4]triazol-1-yl)-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone This compound was prepared using a method analogous to that of Example 1 step 1.6, intermediate 23.2 replacing intermediate 1.5 and (3,5-dimethyl-[1,2,4]triazol-1-yl)-acetic acid replacing (3,5-dimethyl-1H-pyrazol-1-yl)acetic acid. The compound was however purified by preparative LC-MS (III) followed by preparative chiral HPLC (I). LC-MS (A): $t_R$=1.01 min; [M+H]$^+$: 545.4.

Example 24: 2-(3,5-Dimethyl-pyrazol-1-yl)-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone This compound was prepared using a method analogous to that of Example 23 step 23.3, (3,5-dimethyl-1H-pyrazol-1-yl)acetic acid replacing (3,5-dimethyl-[1,2,4]triazol-1-yl)-acetic acid. LC-MS (A): $t_R$=1.15 min; [M+H]$^+$: 544.4.

Example 25: 1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-2-pyrazol-1-yl-ethanone This compound was prepared using a method analogous to that of Example 23 step 23.3, 2-(1H-pyrazol-1-yl)acetic acid replacing (3,5-dimethyl-[1,2,4]triazol-1-yl)-acetic acid. LC-MS (A): $t_R$=1.10 min; [M+H]$^+$: 516.4.

Example 26: 1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-2-[1,2,3]triazol-2-yl-ethanone This compound was prepared using a method analogous to that of Example 23 step 23.3, 2-(2H-1,2,3-triazol-2-yl) acetic acid replacing (3,5-dimethyl-[1,2,4]triazol-1-yl)-acetic acid. LC-MS (A): $t_R$=1.11 min; [M+H]$^+$: 517.3.

Example 27: 1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-3-pyrazol-1-yl-propan-1-one This compound was prepared using a method analogous to that of Example 23 step 23.3, 3-(1H-pyrazol-1-yl)propanoic acid replacing (3,5-dimethyl-[1,2,4]triazol-1-yl)-acetic acid. LC-MS (A): $t_R$=1.13 min; [M+H]$^+$: 530.4.

Example 28: 1-{4-[2-(2-Ethoxy-pyrimidin-5-yl)-5-trifluoromethyl-1,2,3,4-tetrahydro-isoquinolin-8-yl]-piperazin-1-yl}-2-imidazo[4,5-b]pyridin-3-yl-ethanone 28.1. 4-[2-(2,2,2-Trifluoro-acetyl)-5-trifluoromethyl-1,2,3,4-tetrahydro-isoquinolin-8-yl]-piperazine-1-carboxylic acid tert-butyl ester This compound was prepared using a method analogous to that of Example 1 step 1.4, 1-N-Boc-piperazine replacing (R)-1-N-Boc-2-methylpiperazine. LC-MS (B): $t_R$=1.05 min; [M+H]$^+$: 482.03.

28.2. 4-(5-Trifluoromethyl-1,2,3,4-tetrahydro-isoquinolin-8-yl)-piperazine-1-carboxylic acid tert-butyl ester This compound was prepared using a method analogous to that of Example 1 step 1.7, intermediate 28.1 replacing intermediate 1.6. LC-MS (B): $t_R$=0.73 min; [M+H]$^+$: 386.10.

28.3. 4-[2-(2-Ethoxy-pyrimidin-5-yl)-5-trifluoromethyl-1,2,3,4-tetrahydro-isoquinolin-8-yl]-piperazine-1-carboxylic acid tert-butyl ester This compound was prepared using a method analogous to that of Example 1 step 1.8, intermediate 28.2 replacing intermediate 1.7 and 5-bromo-2-ethoxypyrimidine replacing 2-chloro-5-(1H-pyrazol-1-ylmethyl)-1,3-thiazole. The crude was nevertheless purified by CC (Biotage, SNAP 25 g cartridge, solvent A: Hept; solvent B: EA; gradient in % B: 12 for 4CV, 12 to 100 over 10CV, 100 for 2CV). LC-MS (B): $t_R$=1.06 min; [M+H]$^+$: 508.31.

28.4. 2-(2-Ethoxy-pyrimidin-5-yl)-8-piperazin-1-yl-5-trifluoromethyl-1,2,3,4-tetrahydro-isoquinoline, hydrochloride salt This compound was prepared using a method analogous to that of Example 1 step 1.5, intermediate 28.3 replacing intermediate 1.4. LC-MS (B): $t_R$=0.70 min; [M+H]$^+$: 408.25.

28.5. 1-{4-[2-(2-Ethoxy-pyrimidin-5-yl)-5-trifluoromethyl-1,2,3,4-tetrahydro-isoquinolin-8-yl]-piperazin-1-yl}-2-imidazo[4,5-b]pyridin-3-yl-ethanone This compound was prepared using a method analogous to that of Example 1 step 1.6, intermediate 28.4 replacing intermediate 1.5 and imidazo[4,5-b]pyridin-3-yl-acetic acid replacing (3,5-dimethyl-1H-pyrazol-1-yl)acetic acid. The compound was however purified by preparative LC-MS (III). LC-MS (A): $t_R$=1.1 min; [M+H]$^+$: 567.4.

Example 29 to Example 33 were synthesized starting from the appropriate acetic acid derivative and following the procedure described in Example 28, step 28.5. LC-MS data of Example 29 to Example 33 are listed in the table below. The LC-MS conditions used were LC-MS (A).

| Example No | Name | $t_R$ | [M + H]$^+$ |
|---|---|---|---|
| 29 | 2-(3,5-Dimethyl-pyrazol-1-yl)-1-{4-[2-(2-ethoxy-pyrimidin-5-yl)-5-trifluoromethyl-1,2,3,4-tetrahydro-isoquinolin-8-yl]-piperazin-1-yl}-ethanone | 1.18 | 544.4 |
| 30 | 2-(3,5-Dimethyl-[1,2,4]triazol-1-yl)-1-{4-[2-(2-ethoxy-pyrimidin-5-yl)-5-trifluoromethyl-1,2,3,4-tetrahydro-isoquinolin-8-yl]-piperazin-1-yl}-ethanone | 1.04 | 545.4 |
| 31 | 1-{4-[2-(2-Ethoxy-pyrimidin-5-yl)-5-trifluoromethyl-1,2,3,4-tetrahydro-isoquinolin-8-yl]-piperazin-1-yl}-2-pyrazolo[3,4-b]pyridin-1-yl-ethanone | 1.18 | 567.4 |
| 32 | 1-{4-[2-(2-Ethoxy-pyrimidin-5-yl)-5-trifluoromethyl-1,2,3,4-tetrahydro-isoquinolin-8-yl]-piperazin-1-yl}-2-pyrazolo[3,4-b]pyridin-2-yl-ethanone | 1.06 | 567.4 |
| 33 | 1-(2-{4-[2-(2-Ethoxy-pyrimidin-5-yl)-5-trifluoromethyl-1,2,3,4-tetrahydro-isoquinolin-8-yl]-piperazin-1-yl}-2-oxo-ethyl)-1,3-dihydro-indol-2-one | 1.22 | 581.4 |

Example 34: 1-{(S)-4-[2-(2-Ethoxy-pyrimidin-5-yl)-5-trifluoromethyl-1,2,3,4-tetrahydro-isoquinolin-8-yl]-2-methyl-piperazin-1-yl}-2-imidazo[4,5-b]pyridin-3-yl-ethanone

34.1. (S)-2-Methyl-4-[2-(2,2,2-trifluoro-acetyl)-5-trifluoromethyl-1,2,3,4-tetrahydro-isoquinolin-8-yl]-piperazine-1-carboxylic acid tert-butyl ester This compound was prepared using a method analogous to that of Example 1 step 1.4, (S)-1-N-Boc-2-methylpiperazine replacing (R)-1-N-Boc-2-methylpiperazine. LC-MS (B): $t_R$=1.07 min; [M+H]$^+$: 496.26.

34.2. (S)-2-Methyl-4-(5-trifluoromethyl-1,2,3,4-tetrahydro-isoquinolin-8-yl)-piperazine-1-carboxylic acid tert-butyl ester This compound was prepared using a method analogous to that of Example 1 step 1.7, intermediate 34.1 replacing intermediate 1.6. LC-MS (B): $t_R$=0.76 min; [M+H]$^+$: 400.31

34.3. (S)-4-[2-(2-Ethoxy-pyrimidin-5-yl)-5-trifluoromethyl-1,2,3,4-tetrahydro-isoquinolin-8-yl]-2-methyl-piperazine-1-carboxylic acid tert-butyl ester This compound was prepared using a method analogous to that of Example 1 step 1.8, intermediate 34.2 replacing intermediate 1.7 and 5-bromo-2-ethoxypyrimidine replacing 2-chloro-5-(1H-pyrazol-1-ylmethyl)-1,3-thiazole. The crude was nevertheless purified by CC (Biotage, SNAP 25 g cartridge, solvent A: Hept; solvent B: EA; gradient in % B: 8 for 4CV, 8 to 66 over 10CV, 66 for 2CV). LC-MS (B): $t_R$=1.09 min; [M+H]$^+$: 522.31.

34.4. 2-(2-Ethoxy-pyrimidin-5-yl)-8-((S)-3-methyl-piperazin-1-yl)-5-trifluoromethyl-1,2,3,4-tetrahydro-isoquinoline, hydrochloride salt This compound was prepared using a method analogous to that of Example 1 step 1.5, intermediate 34.3 replacing intermediate 1.4. LC-MS (B): $t_R$=0.71 min; [M+H]$^+$: 422.26.

34.5. 1-{(S)-4-[2-(2-Ethoxy-pyrimidin-5-yl)-5-trifluoromethyl-1,2,3,4-tetrahydro-isoquinolin-8-yl]-2-methyl-piperazin-1-yl}-2-imidazo[4,5-b]pyridin-3-yl-ethanone This compound was prepared using a method analogous to that of Example 1 step 1.6, intermediate 34.4 replacing intermediate 1.5 and imidazo[4,5-b]pyridin-3-yl-acetic acid replacing (3,5-dimethyl-1H-pyrazol-1-yl)acetic acid. The compound was however purified by preparative LC-MS (III). LC-MS (A): $t_R$=1.13 min; [M+H]$^+$: 581.4.

Example 35 to Example 37 were synthesized starting from the appropriate acetic acid derivative and following the procedure described in Example 34, step 34.5. Example 35 and 37 were however purified by preparative LC-MS (I). LC-MS data of Example 35 to Example 37 are listed in the table below. The LC-MS conditions used were LC-MS (A).

| Example No | Name | $t_R$ | $[M + H]^+$ |
|---|---|---|---|
| 35 | 2-(3,5-Dimethyl-pyrazol-1-yl)-1-{(S)-4-[2-(2-ethoxy-pyrimidin-5-yl)-5-trifluoromethyl-1,2,3,4-tetrahydro-isoquinolin-8-yl]-2-methyl-piperazin-1-yl}-ethanone | 1.22 | 558.4 |
| 36 | 1-{(S)-4-[2-(2-Ethoxy-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone | 1.2 | 544.4 |
| 37 | 2-(2,3-Dihydro-pyrrolo[2,3-b]pyridin-1-yl)-1-{(S)-4-[2-(2-ethoxy-pyrimidin-5-yl)-5-trifluoromethyl-1,2,3,4-tetrahydro-isoquinolin-8-yl]-2-methyl-piperazin-1-yl}-ethanone | 0.88 | 582.4 |

Example 38: 2-(3,5-Dimethyl-[1,2,4]triazol-1-yl)-1-{(R)-4-[2-(6-fluoro-benzothiazol-2-yl)-5-trifluoromethyl-1,2,3,4-tetrahydro-isoquinolin-8-yl]-2-methyl-piperazin-1-yl}-ethanone 38.1. (R)-4-[2-(6-Fluoro-benzothiazol-2-yl)-5-trifluoromethyl-1,2,3,4-tetrahydro-isoquinolin-8-yl]-2-methyl-piperazine-1-carboxylic acid tert-butyl ester This compound was prepared using a method analogous to that of Example 1 step 1.8, intermediate 16.1 replacing intermediate 1.7 and 2-chloro-6-fluorobenzothiazole replacing 2-chloro-5-(1H-pyrazol-1-ylmethyl)-1,3-thiazole. The crude was purified by CC (solvent A: Hept; solvent B: EA; gradient in % B: 12 for 4CV, 12 to 100 over 10CV, 100 for 2CV). LC-MS (B): $t_R$=1.13 min; $[M+H]^+$: 551.20.

38.2. 2-(6-Fluoro-benzothiazol-2-yl)-8-((R)-3-methyl-piperazin-1-yl)-5-trifluoromethyl-1,2,3,4-tetrahydro-isoquinoline, hydrochloride salt This compound was prepared using a method analogous to that of Example 1 step 1.5, intermediate 38.1 replacing intermediate 1.4. LC-MS (B): $t_R$=0.78 min; $[M+H]^+$: 451.18.

38.3. 2-(3, 5-Dimethyl-[1, 2, 4]triazol-1-yl)-1-{(R)-4-[2-(6-fluoro-benzothiazol-2-yl)-5-trifluoromethyl-1,2,3,4-tetrahydro-isoquinolin-8-yl]-2-methyl-piperazin-1-yl}-ethanone To a vial charged with (3,5-dimethyl-[1,2,4]triazol-1-yl)-acetic acid (18.6 mg) was added a solution of intermediate 38.2 (45 mg) in DMF/DIPEA (0.8 mL/0.2 mL) followed by HATU (45.6 mg). The mixture was stirred at RT for 2 h under argon and filtered through a PL-HCO$_3$ cartridge preconditioned with DCM/MeOH (1/1). The solvents were removed in vacuo and the residue taken up in DMSO/DMF (0.5 mL, 3/2) was purified by preparative LC-MS (IV) to afford 30 mg of beige powder. LC-MS (A): $t_R$=1.25 min; $[M+H]^+$: 588.4.

Example 39 to Example 52 were synthesized starting from the appropriate acetic acid derivative (A1 to A4) and the appropriate amine derivative (B1 to B4) following the procedure described in Example 38, step 38.3.

Acetic acid derivative: A1: (3,5-dimethyl-[1,2,4]triazol-1-yl)-acetic acid; A2: pyrazolo[3,4-b]pyridin-1-yl-acetic acid; A3: (3-methyl-1H-pyrazol-1-yl)acetic acid; A4: (5-methyl-1H-pyrazol-1-yl)acetic acid.

Amine derivative: B1: intermediate 38.2;

B2: 8-((R)-3-Methyl-piperazin-1-yl)-5-trifluoromethyl-2-(4-trifluoromethyl-thiazol-2-yl)-1,2,3,4-tetrahydro-isoquinoline, hydrochloride salt. This compound was prepared using a method analogous to that of Example 38 steps 38.1 and 38.2, 2-bromo-4-(trifluoromethyl)thiazole replacing 2-chloro-6-fluorobenzothiazole in step 38.1. LC-MS (B): $t_R$=0.78 min; $[M+H]^+$: 451.14.

B3: 2-(2-Cyclopropyl-pyrimidin-5-yl)-8-((R)-3-methyl-piperazin-1-yl)-5-trifluoromethyl-1,2,3,4-tetrahydro-isoquinoline, hydrochloride salt. This compound was prepared using a method analogous to that of Example 38 steps 38.1 and 38.2, 5-bromo-2-cyclopropylpyrimidine replacing 2-chloro-6-fluorobenzothiazole in step 38.1. LC-MS (B): $t_R$=0.69 min; $[M+H]^+$: 418.04.

B4: Dimethyl-{5-[8-((R)-3-methyl-piperazin-1-yl)-5-trifluoromethyl-3,4-dihydro-1H-isoquinolin-2-yl]-pyrimidin-2-yl}-amine, hydrochloride salt. This compound was prepared using a method analogous to that of Example 38 steps 38.1 and 38.2, 5-bromo-2-(dimethylamino)pyrimidine replacing 2-chloro-6-fluorobenzothiazole in step 38.1. LC-MS (B): $t_R$=0.65 min; $[M+H]^+$: 421.27.

Acetic acid and amine derivatives for the synthesis of Example 39 to Example 50 and LC-MS data are listed in the table below. The LC-MS conditions used were LC-MS (A).

| Example No | Name | Acetic acid derivative | Amine derivative | $t_R$ | $[M + H]^+$ |
|---|---|---|---|---|---|
| 39 | 1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone | A2 | B1 | 1.38 | 610.3 |
| 40 | 1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-(3-methyl-pyrazol-1-yl)-ethanone | A3 | B1 | 1.36 | 573.4 |
| 41 | 1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-(5-methyl-pyrazol-1-yl)-ethanone | A4 | B1 | 1.36 | 573.3 |

-continued

| Example No | Name | Acetic acid derivative | Amine derivative | $t_R$ | $[M + H]^+$ |
|---|---|---|---|---|---|
| 42 | 2-(3,5-Dimethyl-[1,2,4]triazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone | A1 | B2 | 1.24 | 588.4 |
| 43 | 1-{(R)-2-Methyl-4-[5-trifluoromethyl-2-(4-trifluoromethyl-thiazol-2-yl)-1,2,3,4-tetrahydro-isoquinolin-8-yl]-piperazin-1-yl}-2-pyrazolo[3,4-b]pyridin-1-yl-ethanone | A2 | B2 | 1.37 | 610.4 |
| 44 | 2-(3-Methyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone | A3 | B2 | 1.35 | 573.3 |
| 45 | 2-(5-Methyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone | A4 | B2 | 1.35 | 573.3 |
| 46 | 1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3,5-dimethyl-[1,2,4]triazol-1-yl)-ethanone | A1 | B3 | 1.07 | 555.4 |
| 47 | 1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone | A2 | B3 | 1.22 | 577.4 |
| 48 | 1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone | A3 | B3 | 1.19 | 540.4 |
| 49 | 1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(5-methyl-pyrazol-1-yl)-ethanone | A4 | B3 | 1.19 | 540.4 |
| 50 | 1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3,5-dimethyl-[1,2,4]triazol-1-yl)-ethanone | A1 | B4 | 1.05 | 558.4 |
| 51 | 1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone | A3 | B4 | 1.17 | 543.4 |
| 52 | 1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(5-methyl-pyrazol-1-yl)-ethanone | A4 | B4 | 1.17 | 543.4 |

Example 53: 1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone This compound was prepared using a method analogous to that of Example 1 step 1.6, pyrazolo[3,4-b]pyridin-1-yl-acetic acid replacing (3,5-dimethyl-[1,2,4]triazol-1-yl)-acetic acid and the amine derivative B4 (described in the synthesis of Examples 39 to 52) replacing intermediate 1.5. The compound was however purified by preparative LC-MS (IV followed by III). LC-MS (A): $t_R$=1.20 min; [M+H]$^+$: 580.4.

Example 54: 2-(3,5-Dimethyl-[1,2,4]triazol-1-yl)-1-{(R)-4-[2-(2-ethoxy-pyrimidin-5-yl)-5-trifluoromethyl-1,2,3,4-tetrahydro-isoquinolin-8-yl]-2-methyl-piperazin-1-yl}-ethanone This compound was prepared using a method analogous to that of Example 1 step 1.6, (3,5-dimethyl-[1,2,4]triazol-1-yl)-acetic acid replacing (3,5-dimethyl-1H-pyrazol-1-yl) acetic acid and intermediate 20.2 replacing intermediate 1.5. The compound was however purified by preparative LC-MS (III). LC-MS (A): $t_R$=1.07 min; [M+H]$^+$: 559.4.

Example 55: 2-(3,5-Dimethyl-pyrazol-1-yl)-1-{(R)-4-[2-(2-ethoxy-pyrimidin-5-yl)-5-trifluoromethyl-1,2,3,4-tetrahydro-isoquinolin-8-yl]-2-methyl-piperazin-1-yl}-ethanone This compound was prepared using a method analogous to that of Example 1 step 1.8, 5-bromo-2-ethoxypyrimidine replacing 2-chloro-5-(1H-pyrazol-1-ylmethyl)-1,3-thiazole. The compound was however purified by preparative LC-MS (III). LC-MS (A): $t_R$=1.22 min; [M+H]$^+$: 558.4.

Example 56: 2-(3,5-Dimethyl-pyrazol-1-yl)-1-{(R)-2-methyl-4-[2-(5-phenyl-oxazol-2-yl)-5-trifluoromethyl-1,2,3,4-tetrahydro-isoquinolin-8-yl]-piperazin-1-yl}-ethanone This compound was prepared using a method analogous to that of Example 1 step 1.8, 2-chloro-5-phenyloxazole replacing 2-chloro-5-(1H-pyrazol-1-ylmethyl)-1,3-thiazole. The compound was however purified by preparative LC-MS (I). LC-MS (A): $t_R$=1.33 min; [M+H]$^+$: 579.4.

Example 57: 1-[(R)-4-(2-Benzothiazol-2-yl-5-trifluoromethyl-1,2,3,4-tetrahydro-isoquinolin-8-yl)-2-methyl-piperazin-1-yl]-2-(3,5-dimethyl-pyrazol-1-yl)-ethanone This compound was prepared using a method analogous to that of Example 1 step 1.8, 2-bromobenzothiazole replacing 2-chloro-5-(1H-pyrazol-1-ylmethyl)-1,3-thiazole. The compound was however purified by preparative LC-MS (I). LC-MS (A): $t_R$=1.35 min; [M+H]$^+$: 569.4.

Example 58: 2-(3,5-Dimethyl-[1,2,4]triazol-1-yl)-1-{(R)-4-[2-(2-ethyl-pyrimidin-5-yl)-5-trifluoromethyl-1,2,3,4-tetrahydro-isoquinolin-8-yl]-2-methyl-piperazin-1-yl}-ethanone

58.1. (R)-4-[2-(2-Ethyl-pyrimidin-5-yl)-5-trifluoromethyl-1,2,3,4-tetrahydro-isoquinolin-8-yl]-2-methyl-piperazine-1-carboxylic acid tert-butyl ester This compound was prepared using a method analogous to that of Example 1 step 1.8, intermediate 16.1 replacing intermediate 1.7 and 5-bromo-2-ethylpyrimidine replacing 2-chloro-5-(1H-pyrazol-1-ylmethyl)-1,3-thiazole. The crude was purified by CC (solvent A: Hept; solvent B: EA; gradient in % B: 8 for 4CV, 8 to 66 over 10CV, 66 for 2CV). LC-MS (B): $t_R$=1.03 min; [M+H]$^+$: 506.27.

58.2. 2-(2-Ethyl-pyrimidin-5-yl)-8-((R)-3-methyl-piperazin-1-yl)-5-trifluoromethyl-1,2,3,4-tetrahydro-isoquinoline, hydrochloride salt This compound was prepared using a method analogous to that of Example 1 step 1.5, intermediate 58.1 replacing intermediate 1.4. LC-MS (B): $t_R$=0.67 min; [M+H]$^+$: 406.27.

58.3. 2-(3, 5-Dimethyl-[1, 2, 4]triazol-1-yl)-1-{(R)-4-[2-(2-ethyl-pyrimidin-5-yl)-5-trifluoromethyl-1,2, 3, 4-tetrahydro-isoquinolin-8-yl]-2-methyl-piperazin-1-yl}-ethanone This compound was prepared using a method analogous to that of Example 1 step 1.6, (3,5-dimethyl-[1,2,4]triazol-1-yl)-acetic acid replacing (3,5-dimethyl-1H-pyrazol-1-yl) acetic acid and intermediate 58.2 replacing intermediate 1.5. The compound was however purified by preparative LC-MS (III). LC-MS (A): $t_R$=1.01 min; [M+H]$^+$: 543.4.

Example 59: 2-(3,5-Dimethyl-[1,2,4]triazol-1-yl)-1-{(R)-2-methyl-4-[5-trifluoromethyl-2-(2-trifluoromethyl-pyrimidin-5-yl)-1,2,3,4-tetrahydro-isoquinolin-8-yl]-piperazin-1-yl}-ethanone

59.1. (R)-2-Methyl-4-[5-trifluoromethyl-2-(2-trifluoromethyl-pyrimidin-5-yl)-1,2,3,4-tetrahydro-isoquinolin-8-yl]-piperazine-1-carboxylic acid tert-butyl ester This compound was prepared using a method analogous to that of Example 1 step 1.8, intermediate 16.1 replacing intermediate 1.7 and 5-bromo-2-(trifluoromethyl)pyrimidine replacing 2-chloro-5-(1H-pyrazol-1-ylmethyl)-1,3-thiazole. The crude was purified by CC (solvent A: Hept; solvent B: EA; gradient in % B: 8 for 4CV, 8 to 66 over 10CV, 66 for 2CV). LC-MS (B): $t_R$=1.10 min; [M+H]$^+$: 546.04.

59.2. 8-((R)-3-Methyl-piperazin-1-yl)-5-tfrifluoromehyl-2-(2-trifluoromethyl-pyrimidin-5-yl)-1,2,3,4-tetrahydro-isoquinoline, hydrochloride salt This compound was prepared using a method analogous to that of Example 1 step 1.5, intermediate 59.1 replacing intermediate 1.4. LC-MS (B): $t_R$=0.76 min; [M+MeCN+H]$^+$: 487.16.

59.3. 2-(3, 5-Dimethyl-[1, 2, 4]triazol-1-yl)-1-{(R)-2-methyl-4-[5-trifluoromethyl-2-(2-trifluoromethyl-pyrimidin-5-yl)-1,2,3,4-tetrahydro-isoquinolin-8-yl]-piperazin-1-yl}-ethanone This compound was prepared using a method analogous to that of Example 1 step 1.6, (3,5-dimethyl-[1,2,4]triazol-1-yl)-acetic acid replacing (3,5-dimethyl-1H-pyrazol-1-yl) acetic acid and intermediate 59.2 replacing intermediate 1.5. The compound was however purified by preparative LC-MS (III). LC-MS (A): $t_R$=1.13 min; [M+H]$^+$: 583.4.

Example 60: 8-[(R)-4-(2-Imidazo[4,5-b]pyridin-3-yl-acetyl)-3-methyl-piperazin-1-yl]-3,4-dihydro-1H-isoquinoline-2-carboxylic acid benzyl ester

60.1. (R)-4-Isoquinolin-8-yl-2-methyl-piperazine-1-carboxylic acid tert-butyl ester To a solution of 8-bromoisoquinoline (5.3 g) in toluene (120 mL) was added successively (R)-1-N-Boc-2-methyl-piperazine (4.84 g), tris(dibenzylideneacetone)dipalladium (0) (1.17 g), rac-2,2'-bis(diphenylphosphino)-1,1'-binaphthalene (2.38 g) and sodium tert-butoxide (3.42 g). The reaction mixture was stirred at 90° C. under argon for 3 h, cooled down and filtered through celite. The plug was washed with EA and the resulting solution was evaporated to dryness. The crude was purified by CC (Biotage, SNAP 100 g cartridge, solvent A: Hept; solvent B: EA; gradient in % B: 15 for 3CV, 15 to 50 over 4CV, 50 for 4CV) to afford 8.15 g of brown foam. LC-MS (B): $t_R$=0.70 min; [M+H]$^+$: 328.26.

60.2. (R)-2-Methyl-4-(1,2,3,4-tetrahydro-isoquinolin-8-yl)-piperazine-1-carboxylic acid tert-butyl ester To a solution of intermediate 60.1 (8.15 g) in isopropanol was added platinum(IV) oxide (6.5 g, CAS 1314-15-4)

under argon. The flask was evacuated and backfilled with argon three times, then evacuated and backfilled with hydrogen twice. The resulting mixture was stirred for 45 h under hydrogen (6 bars). After removel of hydrogen, the mixture was slowly filtered off and solids were carefully washed with isopropanol and MeOH. The solution was evaporated in vacuo to afford 7.98 g of black foam. LC-MS (C): $t_R$=0.92 min; [M+H]$^+$: 332.25.

60.3. 8-((R)-4-tert-Butoxycarbonyl-3-methyl-piperazin-1-yl)-3,4-dihydro-1H-isoquinoline-2-carboxylic acid benzyl ester To an ice-cold solution of intermediate 60.2 (7.98 g) and TEA (10.27 mL) in DCM (160 mL) was added benzyl chloroformate (3.98 mL). The reaction mixture was stirred for 2 h at 0° C., 0.2 eq of benzyl chloroformate was added and the mixture was further stirred for 1 h at 0° C. Citric acid 10% was added and the phases were separated. The aq. phase was washed with DCM, the combined org. layers were dried (Na$_2$SO$_4$) and concentrated in vacuo. The crude was purified by CC (silica gel, EA/Hept 3/7) to afford 8.26 g of yellow oil. LC-MS (B): $t_R$=1.07 min; [M+H]$^+$: 466.13.

60.4. 8-((R)-3-Methyl-piperazin-1-yl)-3,4-dihydro-1H-isoquinoline-2-carboxylic acid benzyl ester, hydrochloride salt This compound was prepared using a method analogous to that of Example 1 step 1.5, intermediate 60.4 replacing intermediate 1.4. LC-MS (B): $t_R$=0.72 min; [M+H]$^+$: 366.13.

60.5. 8-[(R)-4-(2-Imidazo[4,5-b]pyridin-3-yl-acetyl)-3-methyl-piperazin-1-yl]-3,4-dihydro-1H-isoquinoline-2-carboxylic acid benzyl ester This compound was prepared using a method analogous to that of Example 1 step 1.6, imidazo[4,5-b]pyridin-3-yl-acetic acid replacing (3,5-dimethyl-1H-pyrazol-1-yl)acetic acid and intermediate 60.4 replacing intermediate 1.5. The compound was however purified by CC (Biotage; first purification: SNAP 100 g cartridge, solvent A: DCM; solvent B: MeOH; gradient in % B: 1 for 4CV, 1 to 10 over 10CV, 10 for 6CV; second purification: FLASH C18 70 g cartridge, solvent A: water; solvent B: MeCN; gradient in % B: 10 for 4CV, 10 to 100 over 10CV, 100 for 1CV). LC-MS (A): $t_R$=1.11 min; [M+H]$^+$: 525.4.

Example 61: 1-[(R)-4-(2-Cyclopropanecarbonyl-1,2,3,4-tetrahydro-isoquinolin-8-yl)-2-methyl-piperazin-1-yl]-2-imidazo[4,5-b]pyridin-3-yl-ethanone

61.1. 2-Imidazo[4,5-b]pyridin-3-yl-1-[(R)-2-methyl-4-(1,2,3,4-tetrahydro-isoquinolin-8-yl)-piperazin-1-yl]-ethan one To a solution of intermediate 60.5 (1.82 g) in dry MeOH (100 mL) was added Pd/C (10%, 185 mg) and ammonium formate (1.09 g). The reaction mixture was refluxed for 1 h, cooled down, filtered through celite and concentrated to dryness. The resulting solid was washed with MeCN, the resulting suspension was filtered off and evaporated in vacuo. The crude was purified by CC (FLASH C18 20 g cartridge, solvent A: water; solvent B: MeCN; gradient in % B: 5 for 2CV, 5 to 100 over 10CV, 100 for 1CV) to afford 1.32 g of colorless oil. LC-MS (C): $t_R$=0.70 min; [M+H]$^+$: 391.20.

61.2. 1-[(R)-4-(2-Cyclopropanecarbonyl-1,2,3,4-tetrahydro-isoquinolin-8-yl)-2-methyl-piperazin-1-yl]-2-imidazo[4,5-b]pyridin-3-yl-ethan one To cyclopropanecarboxylic acid (10.3 mg) were added a solution of intermediate 61.1 (39 mg) in DMF/DIPEA (0.54 mL, 5/1) and a solution of HOAT (16.3 mg) in DMF (0.45 mL), followed by Si-DCC (0.93 mmol/g, 323 mg). The reaction mixture was stirred at RT for 3 h and at 50° C. for 2 h, and was filtered through a PL-HCO$_3$ cartridge preconditioned with DCM/MeOH (1/1). The cartridge was flushed with DCM/MeOH 1/1 and the resulting solution was evaporated in vacuo. The crude was purified by preparative LC-MS (V) to afford 21 mg of white powder. LC-MS (A): $t_R$=0.88 min; [M+H]$^+$: 459.4.

Example 62 to Example 89 were synthesized starting from the appropriate acetic acid derivative and following a procedure analogous to that of Example 61, step 61.2. LC-MS data of Example 62 to Example 89 are listed in the table below. The LC-MS conditions used were LC-MS (A).

| Example No | Name | $t_R$ | [M + H]$^+$ |
|---|---|---|---|
| 62 | 2-Imidazo[4,5-b]pyridin-3-yl-1-{(R)-4-[2-(4-methoxy-benzoyl)-1,2,3,4-tetrahydro-isoquinolin-8-yl]-2-methyl-piperazin-1-yl}-ethanone | 0.94 | 525.4 |
| 63 | 2-Imidazo[4,5-b]pyridin-3-yl-1-{(R)-2-methyl-4-[2-(2-pyridin-3-yl-acetyl)-1,2,3,4-tetrahydro-isoquinolin-8-yl]-piperazin-1-yl}-ethanone | 0.62 | 510.4 |
| 64 | 1-{8-[(R)-4-(2-Imidazo[4,5-b]pyridin-3-yl-acetyl)-3-methyl-piperazin-1-yl]-3,4-dihydro-1H-isoquinolin-2-yl}-3-(4-methoxy-phenyl)-propan-1-one | 1.01 | 553.4 |
| 65 | 2-Imidazo[4,5-b]pyridin-3-yl-1-{(R)-2-methyl-4-[2-(oxazole-4-carbonyl)-1,2,3,4-tetrahydro-isoquinolin-8-yl]-piperazin-1-yl}-ethanone | 0.81 | 486.4 |
| 66 | 2-Imidazo[4,5-b]pyridin-3-yl-1-{(R)-4-[2-(2-indol-1-yl-acetyl)-1,2,3,4-tetrahydro-isoquinolin-8-yl]-2-methyl-piperazin-1-yl}-ethanone | 1.04 | 548.4 |
| 67 | 1-{8-[(R)-4-(2-Imidazo[4,5-b]pyridin-3-yl-acetyl)-3-methyl-piperazin-1-yl]-3,4-dihydro-1H-isoquinolin-2-yl}-2-methyl-propan-1-one | 0.9 | 461.4 |
| 68 | 2-Imidazo[4,5-b]pyridin-3-yl-1-{(R)-4-[2-(2-methoxy-acetyl)-1,2,3,4-tetrahydro-isoquinolin-8-yl]-2-methyl-piperazin-1-yl}-ethanone | 0.79 | 463.4 |

| Example No | Name | $t_R$ | $[M + H]^+$ |
|---|---|---|---|
| 69 | 1-[(R)-4-(2-Cyclopentanecarbonyl-1,2,3,4-tetrahydro-isoquinolin-8-yl)-2-methyl-piperazin-1-yl]-2-imidazo[4,5-b]pyridin-3-yl-ethanone | 1.00 | 487.4 |
| 70 | 1-[(R)-4-(2-Cyclohexanecarbonyl-1,2,3,4-tetrahydro-isoquinolin-8-yl)-2-methyl-piperazin-1-yl]-2-imidazo[4,5-b]pyridin-3-yl-ethanone | 1.04 | 501.4 |
| 71 | 2-Imidazo[4,5-b]pyridin-3-yl-1-{(R)-2-methyl-4-[2-((R)-1,2,3,4-tetrahydro-naphthalene-1-carbonyl)-1,2,3,4-tetrahydro-isoquinolin-8-yl]-piperazin-1-yl}-ethanone | 1.08 | 549.5 |
| 72 | 1-[(R)-4-(2-Benzoyl-1,2,3,4-tetrahydro-isoquinolin-8-yl)-2-methyl-piperazin-1-yl]-2-imidazo[4,5-b]pyridin-3-yl-ethanone | 0.93 | 495.4 |
| 73 | 2-Imidazo[4,5-b]pyridin-3-yl-1-{(R)-2-methyl-4-[2-(4-methyl-benzoyl)-1,2,3,4-tetrahydro-isoquinolin-8-yl]-piperazin-1-yl}-ethanone | 0.99 | 509.4 |
| 74 | 1-{(R)-4-[2-(4-Chloro-benzoyl)-1,2,3,4-tetrahydro-isoquinolin-8-yl]-2-methyl-piperazin-1-yl}-2-imidazo[4,5-b]pyridin-3-yl-ethanone | 1.01 | 529.4 |
| 75 | 1-{(R)-4-[2-(3,4-Dichloro-benzoyl)-1,2,3,4-tetrahydro-isoquinolin-8-yl]-2-methyl-piperazin-1-yl}-2-imidazo[4,5-b]pyridin-3-yl-ethanone | 1.08 | 563.3 |
| 76 | 1-{(R)-4-[2-(3-Dimethylamino-benzoyl)-1,2,3,4-tetrahydro-isoquinolin-8-yl]-2-methyl-piperazin-1-yl}-2-imidazo[4,5-b]pyridin-3-yl-ethanone | 0.95 | 538.4 |
| 77 | 2-Imidazo[4,5-b]pyridin-3-yl-1-{(R)-2-methyl-4-[2-(4-trifluoromethyl-benzoyl)-1,2,3,4-tetrahydro-isoquinolin-8-yl]-piperazin-1-yl}-ethanone | 1.04 | 563.4 |
| 78 | 2-Imidazo[4,5-b]pyridin-3-yl-1-[(R)-2-methyl-4-(2-phenylacetyl-1,2,3,4-tetrahydro-isoquinolin-8-yl)-piperazin-1-yl]-ethanone | 0.97 | 509.4 |
| 79 | (R)-1-{8-[(R)-4-(2-Imidazo[4,5-b]pyridin-3-yl-acetyl)-3-methyl-piperazin-1-yl]-3,4-dihydro-1H-isoquinolin-2-yl}-2-phenyl-propan-1-one | 1.04 | 523.4 |
| 80 | 2-Imidazo[4,5-b]pyridin-3-yl-1-{(R)-2-methyl-4-[2-(1-phenyl-cyclopropanecarbonyl)-1,2,3,4-tetrahydro-isoquinolin-8-yl]-piperazin-1-yl}-ethanone | 1.02 | 535.4 |
| 81 | 2-Imidazo[4,5-b]pyridin-3-yl-1-{(R)-2-methyl-4-[2-(2-phenoxy-acetyl)-1,2,3,4-tetrahydro-isoquinolin-8-yl]-piperazin-1-yl}-ethanone | 0.99 | 525.4 |
| 82 | 3-(4-Chloro-phenyl)-1-{8-[(R)-4-(2-imidazo[4,5-b]pyridin-3-yl-acetyl)-3-methyl-piperazin-1-yl]-3,4-dihydro-1H-isoquinolin-2-yl}-propan-1-one | 1.1 | 557.4 |
| 83 | 1-{8-[(R)-4-(2-Imidazo[4,5-b]pyridin-3-yl-acetyl)-3-methyl-piperazin-1-yl]-3,4-dihydro-1H-isoquinolin-2-yl}-3-phenyl-propan-1-one | 1.03 | 523.4 |
| 84 | 3-(3,4-Dichloro-phenyl)-1-{8-[(R)-4-(2-imidazo[4,5-b]pyridin-3-yl-acetyl)-3-methyl-piperazin-1-yl]-3,4-dihydro-1H-isoquinolin-2-yl}-propan-1-one | 1.16 | 591.3 |
| 85 | 2-Imidazo[4,5-b]pyridin-3-yl-1-{(R)-2-methyl-4-[2-(quinoline-6-carbonyl)-1,2,3,4-tetrahydro-isoquinolin-8-yl]-piperazin-1-yl}-ethanone | 0.81 | 546.4 |
| 86 | 1-{(R)-4-[2-(2-Benzoimidazol-1-yl-acetyl)-1,2,3,4-tetrahydro-isoquinolin-8-yl]-2-methyl-piperazin-1-yl}-2-imidazo[4,5-b]pyridin-3-yl-ethanone | 0.68 | 549.4 |
| 87 | 2-Imidazo[4,5-b]pyridin-3-yl-1-{(R)-2-methyl-4-[2-(2-pyrazol-1-yl-acetyl)-1,2,3,4-tetrahydro-isoquinolin-8-yl]-piperazin-1-yl}-ethanone | 0.79 | 499.4 |
| 88 | 2-Imidazo[4,5-b]pyridin-3-yl-1-{(R)-2-methyl-4-[2-(2-morpholin-4-yl-acetyl)-1,2,3,4-tetrahydro-isoquinolin-8-yl]-piperazin-1-yl}-ethanone | 0.53 | 518.4 |
| 89 | 2-Imidazo[4,5-b]pyridin-3-yl-1-{(R)-2-methyl-4-[2-(2-methyl-2H-pyrazole-3-carbonyl)-1,2,3,4-tetrahydro-isoquinolin-8-yl]-piperazin-1-yl}-ethanone | 0.82 | 499.4 |

Example 90: 2-Imidazo[4,5-b]pyridin-3-yl-1-{(R)-2-methyl-4-[2-(5-methyl-pyridin-2-yl)-1,2,3,4-tetrahydro-isoquinolin-8-yl]-piperazin-1-yl}-ethanone 90.1. (R)-2-Methyl-4-[2-(5-methyl-pyridin-2-yl)-1,2,3,4-tetrahydro-isoquinolin-8-yl]-piperazine-1-carboxylic acid tert-butyl ester To a vial charged with 2-bromo-5-methylpyridine (51.6 mg) under argon was successively added toluene (0.4 mL), potassium tert-butoxide (58.2 mg), a solution of intermediate 60.2 (49.7 mg) in toluene (0.2 mL), a solution of DavePhos (9.8 mg) in toluene (0.1 mL) and a fine suspension of bis(dibenzylideneacetone)palladium (0) (4.73 mg) in toluene (0.3 mL). The resulting mixture was stirred at 80° C. under argon for 17 h. The solvent was removed and the residue was taken up in DCM/water (4 mL/3 mL). The layers were separated and the org. phase was concentrated in vacuo. The resulting crude was taken up in DMSO/MeCN (0.5 mL/0.1 mL) and purified by preparative LC-MS (VI) to afford 10 mg of yellow oil. LC-MS (D): $t_R$=2.08 min; $[M+H]^+$: 423.0.

90.2. (R)-8-(3-methylpiperazin-1-yl)-2-(5-methyl-2-(5-methylpyridin-2-yl)-1,2,3,4-tetrahydroisoquinoline, hydrochloride salt This compound was prepared using a method analogous to that of Example 23 step 23.2, intermediate 90.1 replacing intermediate 23.1. LC-MS (E): $t_R$=1.15 min; $[M+H]^+$: 323.1.

90.3. 2-Imidazo[4,5-b]pyridin-3-yl-1-{(R)-2-methyl-4-[2-(5-methyl-pyridin-2-yl)-1,2,3,4-tetrahydro-isoquinolin-8-yl]-piperazin-1-yl}-ethanone To a vial charged with intermediate 90.2 (23.7 mg) was successively added DMF/DCM (0.2 mL, 1/1), a solution of imidazo[4,5-b]pyridin-3-yl-acetic acid (12.8 mg) in DMF (0.12 mL), DIPEA (0.054 mL) and a solution of HATU (24 mg) in DMF (0.126 mL). The reaction mixture was stirred at RT under argon for 17 h. DCM/DMF (0.5 mL, 1/1) and PL-HCO$_3$ (1.8 mmol/g, 133 mg) were added and the stirring was pursued for 1 h. The mixture was filtered off, the resin was washed with DMF/DCM and the resulting solution was evaporated in vacuo. The residue was taken up in DMSO/MeCN (0.4 mL/0.05 mL) and purified by preparative LC-MS (VII) to afford 6 mg of beige solid. LC-MS (A): $t_R$=0.64 min; $[M+H]^+$: 482.4.

Example 91 to Example 100 were synthesized in three steps following a procedure analogous to that of Example 90 steps 90.1 to 90.3, starting from the appropriate bromo derivative replacing 2-bromo-5-methylpyridine in step 90.1. LC-MS data of Example 91 to Example 100 are listed in the table below. The LC-MS conditions used were LC-MS (A).

Example 101: 2-Imidazo[4,5-b]pyridin-3-yl-1-[(R)-2-methyl-4-(2-phenyl-1,2,3,4-tetrahydro-isoquinolin-8-yl)-piperazin-1-yl]-ethanone A mixture of intermediate 61.1 (50 mg), bromobenzene (23.3 mg), sodium tert-butoxide (16.9 mg), tris(dibenzylideneaceton)-dipalladium(0) (17.6 mg) and 2-(dicyclohexylphosphino)biphenyl (13.4 mg) in DME (1 mL) was stirred at 100° C. under argon overnight. DCM/water were added and the phases were separated. The org. layer was evaporated in vacuo. The residue was purified by preparative LC-MS (II) to afford 2 mg of white powder. LC-MS (A): $t_R$=1.12 min; $[M+H]^+$: 467.4.

Example 102: 2-Imidazo[4,5-b]pyridin-3-yl-1-[(R)-2-methyl-4-(2-pyrimidin-2-yl-1,2,3,4-tetrahydro-isoquinolin-8-yl)-piperazin-1-yl]-ethanone A mixture of intermediate 61.1 (20 mg), 2-chloropyrimidine (9.07 mg) and TEA (0.0107 mL) in MeCN (1 mL) was stirred at 80° C. under argon overnight. The solvent was removed in vacuo and the residue was purified by preparative LC-MS (VIII) to afford 6 mg of white powder. LC-MS (A): $t_R$=0.98 min; $[M+H]^+$: 469.4.

Example 103: 2-Imidazo[4,5-b]pyridin-3-yl-1-{(R)-2-methyl-4-[2-(5-trifluoromethyl-pyridin-2-yl)-1,2,3,4-tetrahydro-isoquinolin-8-yl]-piperazin-1-yl}-ethanone

103. 1. (R)-2-Methyl-4-[2-(5-trifluoromethyl-pyridin-2-yl)-1,2,3,4-tetrahydro-isoquinolin-8-yl]-piperazine-1-carboxylic acid tert-butyl ester This compound was prepared using a method analogous to that of Example 1 step 1.8, intermediate 60.2 replacing

| Example No | Name | $t_R$ | $[M + H]^+$ |
| --- | --- | --- | --- |
| 91 | 1-{(R)-4-[2-(5-Fluoro-pyridin-2-yl)-1,2,3,4-tetrahydro-isoquinolin-8-yl]-2-methyl-piperazin-1-yl}-2-imidazo[4,5-b]pyridin-3-yl-ethanone | 1.08 | 486.4 |
| 92 | 2-Imidazo[4,5-b]pyridin-3-yl-1-{(R)-2-methyl-4-[2-(6-methyl-pyridin-3-yl)-1,2,3,4-tetrahydro-isoquinolin-8-yl]-piperazin-1-yl}-ethanone | 0.62 | 482.4 |
| 93 | 1-{(R)-4-[2-(4-Chloro-phenyl)-1,2,3,4-tetrahydro-isoquinolin-8-yl]-2-methyl-piperazin-1-yl}-2-imidazo[4,5-b]pyridin-3-yl-ethanone | 1.25 | 501.4 |
| 94 | 2-Imidazo[4,5-b]pyridin-3-yl-1-{(R)-4-[2-(2-methoxy-phenyl)-1,2,3,4-tetrahydro-isoquinolin-8-yl]-2-methyl-piperazin-1-yl}-ethanone | 0.92 | 497.4 |
| 95 | 4-{8-[(R)-4-(2-Imidazo[4,5-b]pyridin-3-yl-acetyl)-3-methyl-piperazin-1-yl]-3,4-dihydro-1H-isoquinolin-2-yl}-benzonitrile | 1.11 | 492.4 |
| 96 | 2-Imidazo[4,5-b]pyridin-3-yl-1-{(R)-2-methyl-4-[2-(4-trifluoromethyl-phenyl)-1,2,3,4-tetrahydro-isoquinolin-8-yl]-piperazin-1-yl}-ethanone | 1.29 | 535.4 |
| 97 | 2-Imidazo[4,5-b]pyridin-3-yl-1-{(R)-4-[2-(3-methoxy-phenyl)-1,2,3,4-tetrahydro-isoquinolin-8-yl]-2-methyl-piperazin-1-yl}-ethanone | 1.13 | 497.4 |
| 98 | 2-Imidazo[4,5-b]pyridin-3-yl-1-{(R)-2-methyl-4-[2-(4-trifluoromethoxy-phenyl)-1,2,3,4-tetrahydro-isoquinolin-8-yl]-piperazin-1-yl}-ethanone | 1.3 | 551.4 |
| 99 | 1-{(R)-4-[2-(4-Fluoro-phenyl)-1,2,3,4-tetrahydro-isoquinolin-8-yl]-2-methyl-piperazin-1-yl}-2-imidazo[4,5-b]pyridin-3-yl-ethanone | 1.14 | 485.4 |
| 100 | 2-Imidazo[4,5-b]pyridin-3-yl-1-{(R)-2-methyl-4-[2-(6-trifluoromethyl-pyridin-3-yl)-1,2,3,4-tetrahydro-isoquinolin-8-yl]-piperazin-1-yl}-ethanone | 1.14 | 536.4 | intermediate 1.7 and 2-bromo-5-(trifluoromethyl)pyridine replacing 2-chloro-5-(1H-pyrazol-1-ylmethyl)-1,3-thiazole. LC-MS (B): $t_R$=1.09 min; [M+H]$^+$: 477.05.

103.2. 8-((R)-3-Methyl-piperazin-1-yl)-2-(5-trifluoromethyl-pyridin-2-yl)-1,2,3,4-tetrahydro-isoquinoline, hydrochloride salt This compound was prepared using a method analogous to that of Example 1 step 1.5, intermediate 103.1 replacing intermediate 1.4. LC-MS (B): $t_R$=0.72 min; [M+H]$^+$: 376.91.

103.3. 2-Imidazo[4,5-b]pyridin-3-yl-1-{(R)-2-methyl-4-[2-(5-trifluoromethyl-pyridin-2-yl)-1,2,3,4-tetrahydro-isoquinolin-8-yl]-piperazin-1-yl}-ethanone This compound was prepared using a method analogous to that of Example 1 step 1.6, intermediate 103.2 replacing intermediate 1.5 and imidazo[4,5-b]pyridin-3-yl-acetic acid replacing (3,5-dimethyl-1H-pyrazol-1-yl)acetic acid. LC-MS (A): $t_R$=1.23 min; [M+H]$^+$: 536.3.

Example 104 to Example 117 were synthesized in three steps following a procedure analogous to that of Example 103 steps 103.1 to 103.3, starting from the appropriate chloro, bromo or iodo derivative replacing 2-bromo-5-(trifluoromethyl)pyridine in step 103.1. LC-MS data of Example 104 to Example 117 are listed in the table below. The LC-MS conditions used were LC-MS (A), except for Examples 105, 111, 115 whereby the LC-MS conditions used were LC-MS (B).

| Example No | Name | Chloro, bromo or iodo derivative | $t_R$ | [M + H]$^+$ |
|---|---|---|---|---|
| 104 | 2-Imidazo[4,5-b]pyridin-3-yl-1-[(R)-2-methyl-4-(2-pyridin-2-yl-1,2,3,4-tetrahydro-isoquinolin-8-yl)-piperazin-1-yl]-ethanone | 2-Chloro-pyridine | 0.62 | 468.4 |
| 105 | 2-Imidazo[4,5-b]pyridin-3-yl-1-{(R)-4-[2-(4-methoxy-phenyl)-1,2,3,4-tetrahydro-isoquinolin-8-yl]-2-methyl-piperazin-1-yl}-ethanone | 4-Iodo-anisole | 0.65 | 496.9 |
| 106 | 2-Imidazo[4,5-b]pyridin-3-yl-1-[(R)-2-methyl-4-(2-pyrimidin-5-yl-1,2,3,4-tetrahydro-isoquinolin-8-yl)-piperazin-1-yl]-ethanone | 5-Bromo-pyrimidine | 0.85 | 469.4 |
| 107 | 2-Imidazo[4,5-b]pyridin-3-yl-1-{(R)-2-methyl-4-[2-(2-trifluoromethyl-pyrimidin-5-yl)-1,2,3,4-tetrahydro-isoquinolin-8-yl]-piperazin-1-yl}-ethanone | 5-Bromo-2-(trifluoromethyl)pyrimidine | 1.08 | 537.4 |
| 108 | 2-Imidazo[4,5-b]pyridin-3-yl-1-{(R)-2-methyl-4-[2-(5-methyl-pyrimidin-2-yl)-1,2,3,4-tetrahydro-isoquinolin-8-yl]-piperazin-1-yl}-ethanone | 2-Bromo-5-methylpyrimidine | 1.03 | 483.4 |
| 109 | 2-Imidazo[4,5-b]pyridin-3-yl-1-{(R)-2-methyl-4-[2-(2-methyl-pyrimidin-5-yl)-1,2,3,4-tetrahydro-isoquinolin-8-yl]-piperazin-1-yl}-ethanone | 5-Bromo-2-methylpyrimidine | 0.85 | 483.4 |
| 110 | 2-Imidazo[4,5-b]pyridin-3-yl-1-{(R)-2-methyl-4-[2-(2-propyl-pyrimidin-5-yl)-1,2,3,4-tetrahydro-isoquinolin-8-yl]-piperazin-1-yl}-ethanone | 5-Bromo-2-(n-propyl)pyrimidine | 1 | 511.4 |
| 111 | 2-Imidazo[4,5-b]pyridin-3-yl-1-{(R)-4-[2-(2-isopropoxy-pyrimidin-5-yl)-1,2,3,4-tetrahydro-isoquinolin-8-yl]-2-methyl-piperazin-1-yl}-ethanone | 5-Bromo-2-isopropoxy pyrimidine | 0.83 | 527.2 |
| 112 | 2-Imidazo[4,5-b]pyridin-3-yl-1-((R)-2-methyl-4-{2-[2-(2,2,2-trifluoro-ethoxy)-pyrimidin-5-yl]-1,2,3,4-tetrahydro-isoquinolin-8-yl}-piperazin-1-yl)-ethanone | 2-Bromo-2-(2,2,2-trifluoroethoxy)pyrimidine | 1.11 | 567.4 |
| 113 | 2-Imidazo[4,5-b]pyridin-3-yl-1-[(R)-2-methyl-4-(2-thiazol-2-yl-1,2,3,4-tetrahydro-isoquinolin-8-yl)-piperazin-1-yl]-ethanone | 2-Bromo-thiazole | 0.8 | 474.3 |
| 114 | 2-Imidazo[4,5-b]pyridin-3-yl-1-{(R)-2-methyl-4-[2-(4-methyl-thiazol-2-yl)-1,2,3,4-tetrahydro-isoquinolin-8-yl]-piperazin-1-yl}-ethanone | 2-Bromo-4-methylthiazole | 1.06 | 488.3 |
| 115 | 2-Imidazo[4,5-b]pyridin-3-yl-1-{(R)-2-methyl-4-[2-(5-phenyl-thiazol-2-yl)-1,2,3,4-tetrahydro-isoquinolin-8-yl]-piperazin-1-yl}-ethanone | 2-Bromo-5-phenylthiazole | 0.81 | 550.0 |
| 116 | 1-{(R)-4-[2-(4,5-Dimethyl-thiazol-2-yl)-1,2,3,4-tetrahydro-isoquinolin-8-yl]-2-methyl-piperazin-1-yl}-2-imidazo[4,5-b]pyridin-3-yl-ethanone | 2-Bromo-4,5-dimethylthiazole | 0.72 | 502.4 |

| Example No | Name | Chloro, bromo or iodo derivative | $t_R$ | $[M + H]^+$ |
|---|---|---|---|---|
| 117 | 2-{8-[(R)-4-(2-Imidazo[4,5-b]pyridin-3-yl-acetyl)-3-methyl-piperazin-1-yl]-3,4-dihydro-1H-isoquinolin-2-yl}-thiazole-4-carbonitrile | 2-Bromo-4-cyanothiazole | 1.05 | 499.3 |

Example 118 to Example 122 were synthesized in three steps following a procedure analogous to that of Example 103 steps 103.1 to 103.3, starting from the appropriate chloro or bromo derivative replacing 2-bromo-5-(trifluoromethyl)pyridine in step 103.1, and using a 3/1 mixture of 4M HCl in dioxane/MeOH instead of 4M HCl in dioxane in step 103.2. LC-MS data of Example 118 to Example 122 are listed in the table below. The LC-MS conditions used were LC-MS (A).

| Example No | Name | Chloro or bromo derivative | $t_R$ | $[M + H]^+$ |
|---|---|---|---|---|
| 118 | 2-Imidazo[4,5-b]pyridin-3-yl-1-{(R)-4-[2-(2-methoxy-pyrimidin-5-yl)-1,2,3,4-tetrahydro-isoquinolin-8-yl]-2-methyl-piperazin-1-yl}-ethanone | 5-Bromo-2-methoxy pyrimidine | 0.94 | 499.4 |
| 119 | 2-Imidazo[4,5-b]pyridin-3-yl-1-{(R)-4-[2-(6-methoxy-pyridazin-3-yl)-1,2,3,4-tetrahydro-isoquinolin-8-yl]-2-methyl-piperazin-1-yl}-ethanone | 3-Chloro-6-methoxy pyridazine | 0.69 | 499.4 |
| 120 | 2-Imidazo[4,5-b]pyridin-3-yl-1-{(R)-4-[2-(6-methoxy-pyrazin-2-yl)-1,2,3,4-tetrahydro-isoquinolin-8-yl]-2-methyl-piperazin-1-yl}-ethanone | 2-Chloro-6-methoxy pyrazine | 1.04 | 499.4 |
| 121 | 1-{(R)-4-[2-(4,6-Dimethoxy-[1,3,5]triazin-2-yl)-1,2,3,4-tetrahydro-isoquinolin-8-yl]-2-methyl-piperazin-1-yl}-2-imidazo[4,5-b]pyridin-3-yl-ethanone | 2-Chloro-4,6-dimethoxy-triazine | 1.03 | 530.4 |
| 122 | 2-Imidazo[4,5-b]pyridin-3-yl-1-{(R)-4-[2-(2-methoxy-pyrimidin-4-yl)-1,2,3,4-tetrahydro-isoquinolin-8-yl]-2-methyl-piperazin-1-yl}-ethanone | 2-Methoxy-4-bromo-pyrimidine | 0.83 | 499.4 |

Example 123: 1-{(R)-4-[2-(2-Ethoxy-pyrimidin-5-yl)-1,2,3,4-tetrahydro-isoquinolin-8-yl]-2-methyl-piperazin-1-yl}-2-imidazo[4,5-b]pyridin-3-yl-ethanone This compound was synthesized in three steps following a procedure analogous to that of Example 103 steps 103.1 to 103.3, 5-bromo-2-ethoxypyrimidine replacing 2-bromo-5-(trifluoromethyl)pyridine in step 103.1, and using a 3/1 mixture of 4M HCl in dioxane/EtOH instead of 4M HCl in dioxane in step 103.2. LC-MS (A): $t_R$=1.01 min; $[M+H]^+$: 513.4.

Example 124: 2-Imidazo[4,5-b]pyridin-3-yl-1-{(R)-2-methyl-4-[2-(4-phenyl-thiazol-2-yl)-1,2,3,4-tetrahydro-isoquinolin-8-yl]-piperazin-1-yl}-ethanone

124.1. (R)-2-Methyl-4-[2-(4-phenyl-thiazol-2-yl)-1,2,3,4-tetrahydro-isoquinolin-8-yl]-piperazine-1-carboxylic acid tert-butyl ester To a vial charged with 2-chloro-4-(phenyl)thiazole (14 mg) under argon was added a solution of intermediate 60.2 (20 mg) in degased toluene (1 mL), palladium(II) diacetate (1.35 mg), RuPhos (2.82 mg) and sodium tert-butoxide (7.17 mg). The mixture was degased and heated at 85° C. under argon overnight. Toluene was removed in vacuo and the residue was purified by CC (Biotage; SNAP 10 g cartridge, solvent A: Hept; solvent B: EA; gradient in % B: 12 for 4CV, 12 to 100 over 10CV, 100 for 2CV, MeOH for 4CV) to afford 13 mg of beige powder. LC-MS (B): $t_R$=1.11 min; $[M+H]^+$: 491.27.

124.2. 2-Imidazo[4,5-b]pyridin-3-yl-1-{(R)-2-methyl-4-[2-(4-phenyl-thiazol-2-yl)-1,2,3,4-tetrahydro-isoquinolin-8-yl]-piperazin-1-yl}-ethanone This compound was prepared in two steps following a procedure analogous to that of Example 103 steps 103.2 to 103.3, intermediate 124.1 replacing intermediate 103.1 in step 103.2. LC-MS (A): $t_R$=1.30 min; $[M+H]^+$: 550.4.

Example 125: 2-(3,5-Dimethyl-[1,2,4]triazol-1-yl)-1-{(R)-2-methyl-4-[2-(2-trifluoromethyl-pyrimidin-5-yl)-1,2,3,4-tetrahydro-isoquinolin-8-yl]-piperazin-1-yl}-ethanone This compound was synthesized in three steps following a procedure analogous to that of Example 103 steps 103.1 to 103.3, 5-bromo-2-(trifluoromethyl)pyrimidine replacing 2-bromo-5-(trifluoromethyl)pyridine in step 103.1, and (3,5-dimethyl-[1,2,4]triazol-1-yl)-acetic acid replacing imidazo[4,5-b]pyridin-3-yl-acetic acid in step 103.3. LC-MS (A): $t_R$=1.01 min; $[M+H]^+$: 515.4.

Example 126: 1-{(R)-4-[2-(2-Cyclopropyl-pyrimidin-5-yl)-1,2,3,4-tetrahydro-isoquinolin-8-yl]-2-methyl-piperazin-1-yl}-2-(3,5-dimethyl-[1,2,4]triazol-1-yl)-ethanone This compound was synthesized in three steps following a procedure analogous to that of Example 103 steps 103.1 to 103.3, 5-bromo-2-(cyclopropyl)pyrimidine replacing 2-bromo-5-(trifluoromethyl)pyridine in step 103.1, and (3,5-dimethyl-[1,2,4]triazol-1-yl)-acetic acid replacing imidazo[4,5-b]pyridin-3-yl-acetic acid in step 103.3. LC-MS (A): $t_R$=0.93 min; [M+H]$^+$: 487.4.

Example 127: 2-(3,5-Dimethyl-[1,2,4]triazol-1-yl)-1-{(R)-4-[2-(2-ethoxy-pyrimidin-5-yl)-1,2,3,4-tetrahydro-isoquinolin-8-yl]-2-methyl-piperazin-1-yl}-ethanone This compound was synthesized in three steps following a procedure analogous to that of Example 103 steps 103.1 to 103.3, 5-bromo-2-ethoxypyrimidine replacing 2-bromo-5-(trifluoromethyl)pyridine in step 103.1, using a 3/1 mixture of 4M HCl in dioxane/EtOH instead of 4M HCl in dioxane in step 103.2, and (3,5-dimethyl-[1,2,4]triazol-1-yl)-acetic acid replacing imidazo[4,5-b]pyridin-3-yl-acetic acid in step 103.3. LC-MS (C): $t_R$=0.79 min; [M]$^+$: 491.27

Example 128: 2-(3,5-Dimethyl-pyrazol-1-yl)-1-{(R)-4-[2-(2-ethoxy-pyrimidin-5-yl)-1,2,3,4-tetrahydro-isoquinolin-8-yl]-2-methyl-piperazin-1-yl}-ethanone This compound was synthesized in three steps following a procedure analogous to that of Example 103 steps 103.1 to 103.3, 5-bromo-2-ethoxypyrimidine replacing 2-bromo-5-(trifluoromethyl)pyridine in step 103.1, using a 3/1 mixture of 4M HCl in dioxane/EtOH instead of 4M HCl in dioxane in step 103.2, and (3,5-dimethyl-pyrazol-1-yl)-acetic acid replacing imidazo[4,5-b]pyridin-3-yl-acetic acid in step 103.3. LC-MS (A): $t_R$=1.10 min; [M+H]$^+$: 490.4.

Example 129: 1-{(R)-4-[2-(2-Ethoxy-pyrimidin-5-yl)-5-fluoro-1,2,3,4-tetrahydro-isoquinolin-8-yl]-2-methyl-piperazin-1-yl}-2-imidazo[4,5-b]pyridin-3-yl-ethanone

129.1. 1-(8-Bromo-5-fluoro-3,4-dihydro-1H-isoquinolin-2-yl)-2,2,2-trifluoro-ethanone To an ice-cold suspension of 8-bromo-5-fluoro-1,2,3,4-tetrahydro-isoquinoline hydrochloride (1.9 g, WO2013/093842) in DCM (18 mL) was added pyridine (2.87 mL) followed by trifluoroacetic anhydride (1.5 mL). The resulting solution was stirred at 0° C. for 45 min and water was added. The layers were separated and the aq. phase was extracted with DCM. The combined org. phases were washed with 1M HCl and brine, were dried (MgSO$_4$) and evaporated in vacuo to afford 2.15 g of brown oil. LC-MS (B): $t_R$=0.94 min.

129.2. (R)-4-[5-Fluoro-2-(2,2,2-trifluoro-acetyl)-1,2,3,4-tetrahydro-isoquinolin-8-yl]-2-methyl-piperazine-1-carboxylic acid tert-butyl ester This compound was prepared using a method analogous to that of Example 1 step 1.4, intermediate 129.1 replacing intermediate 1.3. LC-MS (B): $t_R$=1.04 min; [M+H]$^+$: 446.26.

129.3. (R)-4-(5-Fluoro-1,2,3,4-tetrahydro-isoquinolin-8-yl)-2-methyl-piperazine-1-carboxylic acid tert-butyl ester This compound was prepared using a method analogous to that of Example 1 step 1.7, intermediate 129.2 replacing intermediate 1.6. LC-MS (B): $t_R$=0.71 min; [M+H]$^+$: 350.06.

129.4. (R)-4-[2-(2-Ethoxy-pyrimidin-5-yl)-5-fluoro-1,2,3,4-tetrahydro-isoquinolin-8-yl]-2-methyl-piperazine-1-carboxylic acid tert-butyl ester This compound was prepared using a method analogous to that of Example 1 step 1.8, intermediate 129.3 replacing intermediate 1.7 and 5-bromo-2-ethoxypyrimidine replacing 2-chloro-5-(1H-pyrazol-1-ylmethyl)-1,3-thiazole. LC-MS (B): $t_R$=1.05 min; [M+H]$^+$: 472.31.

129.5. 2-(2-Ethoxy-pyrimidin-5-yl)-5-fluoro-8-((R)-3-methyl-piperazin-1-yl)-1,2,3,4-tetrahydro-isoquinoline, hydrochloride salt This compound was prepared using a method analogous to that of Example 1 step 1.5, intermediate 129.4 replacing intermediate 1.4 and using a 3/1 mixture of 4M HCl in dioxane/EtOH instead of 4M HCl in dioxane. LC-MS (B): $t_R$=0.67 min; [M+H]$^+$: 372.35.

129.6. 1-{(R)-4-[2-(2-Ethoxy-pyrimidin-5-yl)-5-fluoro-1,2,3,4-tetrahydro-isoquinolin-8-yl]-2-methyl-piperazin-1-yl}-2-imidazo[4,5-b]pyridin-3-yl-ethanone This compound was prepared using a method analogous to that of Example 1 step 1.6, intermediate 129.5 replacing intermediate 1.5 and imidazo[4,5-b]pyridin-3-yl-acetic acid replacing (3,5-dimethyl-1H-pyrazol-1-yl)acetic acid. LC-MS (A): $t_R$=1.03 min; [M+H]$^+$: 531.4.

Example 130: 2-(3,5-Dimethyl-pyrazol-1-yl)-1-{(R)-4-[2-(2-ethoxy-pyrimidin-5-yl)-5-fluoro-1,2,3,4-tetrahydro-isoquinolin-8-yl]-2-methyl-piperazin-1-yl}-ethanone This compound was prepared using a method analogous to that of Example 1 step 1.6, intermediate 129.5 replacing intermediate 1.5. LC-MS (A): $t_R$=1.12 min; [M+H]$^+$: 508.4.

Example 131: 2-(3,5-Dimethyl-[1,2,4]triazol-1-yl)-1-{(R)-4-[2-(2-ethoxy-pyrimidin-5-yl)-5-fluoro-1,2,3,4-tetrahydro-isoquinolin-8-yl]-2-methyl-piperazin-1-yl}-ethanone This compound was prepared using a method analogous to that of Example 1 step 1.6, intermediate 129.5 replacing intermediate 1.5 and (3,5-dimethyl-[1,2,4]triazol-1-yl)-acetic acid replacing (3,5-dimethyl-1H-pyrazol-1-yl)acetic acid. LC-MS (B): $t_R$=0.77 min; [M+H]$^+$: 508.85.

Example 132: 2-(3,5-Dimethyl-[1,2,4]triazol-1-yl)-1-{(R)-4-[5-fluoro-2-(2-trifluoromethyl-pyrimidin-5-yl)-1,2,3,4-tetrahydro-isoquinolin-8-yl]-2-methyl-piperazin-1-yl}-ethanone This compound was synthesized in three steps following a procedure analogous to that of Example 103 steps 103.1 to 103.3, intermediate 129.3 replacing intermediate 60.2 and 5-bromo-2-(trifluoromethyl)pyrimidine replacing 2-bromo-5-(trifluoromethyl)pyridine in step 103.1, and (3,5-dimethyl-[1,2,4]triazol-1-yl)-acetic acid replacing imidazo[4,5-b]pyridin-3-yl-acetic acid in step 103.3. LC-MS (A): $t_R$=1.04 min; [M+H]$^+$: 533.4.

Example 133: 1-{(R)-4-[2-(2-Cyclopropyl-pyrimidin-5-yl)-5-fluoro-1,2,3,4-tetrahydro-isoquinolin-8-yl]-2-methyl-piperazin-1-yl}-2-(3,5-dimethyl-[1,2,4]triazol-1-yl)-ethanone This compound was synthesized in three steps following a procedure analogous to that of Example 103 steps 103.1 to 103.3, intermediate 129.3 replacing intermediate 60.2 and 5-bromo-2-(cyclopropyl)pyrimidine replacing 2-bromo-5-(trifluoromethyl)pyridine in step 103.1, and (3,5-dimethyl-[1,2,4]triazol-1-yl)-acetic acid replacing imidazo[4,5-b]pyridin-3-yl-acetic acid in step 103.3. LC-MS (A): $t_R$=0.97 min; [M+H]$^+$: 505.4.

Example 134: 1-{(R)-4-[2-(2-Ethoxy-pyrimidin-5-yl)-6-trifluoromethyl-1,2,3,4-tetrahydro-isoquinolin-8-yl]-2-methyl-piperazin-1-yl}-2-imidazo[4,5-b]pyridin-3-yl-ethanone 134.1. 1-(8-Chloro-6-trifluoromethyl-3,4-dihydro-1H-isoquinolin-2-yl)-2,2,2-trifluoro-ethanone This compound was synthesized in three steps following a procedure analogous to that of Example 1 steps 1 to 3, 2-(3-chloro-5-(trifluoromethyl)phenyl)acetonitrile replacing 2-(5-chloro-2-(trifluoromethyl)phenyl)acetonitrile in step 1. It was obtained as a mixture of regioisomers 2/1 ratio together with 1-(6-chloro-8-trifluoromethyl-3,4-dihydro-1H-isoquinolin-2-yl)-2,2,2-trifluoro-ethanone. Major regioisomer: LC-MS (B): $t_R$=0.98 min. $^1$H-NMR (CDCl$_3$): 7.56 (d, 1H); 7.38 (m, 1H); 4.90 (m, 2H); 3.90 (m, 2H); 3.05 (m, 2H). Minor regioisomer: LC-MS (B): $t_R$=0.93 min. $^1$H-NMR (CDCl$_3$): 7.56 (d, 1H); 7.38 (m, 1H); 4.90 (m, 2H); 3.65 (m, 2H); 2.98 (m, 2H).

134.2. (R)-2-Methyl-4-[2-(2,2,2-trifluoro-acetyl)-6-trifluoromethyl-1,2,3,4-tetrahydro-isoquinolin-8-yl]-piperazine-1-carboxylic acid tert-butyl ester This compound was prepared using a method analogous to that of Example 1 step 1.4, intermediate 134.1 (mixture of regioisomers) replacing intermediate 1.3. Major regioisomer: LC-MS (B): $t_R$=1.07 min; [M+H]$^+$: 496.22. Minor regioisomer: LC-MS (B): $t_R$=1.02 min.

134.3. (R)-2-Methyl-4-(6-trifluoromethyl-1,2,3,4-tetrahydro-isoquinolin-8-yl)-piperazine-1-carboxylic acid tert-butyl ester This compound was prepared using a method analogous to that of Example 1 step 1.7, intermediate 134.2 (mixture of regioisomers) replacing intermediate 1.6. Major regioisomer: LC-MS (B): $t_R$=0.75 min; [M+H]$^+$: 400.11. Minor regioisomer: LC-MS (B): $t_R$=0.77 min; [M+H]$^+$: 400.10.

134.4. 1-{(R)-4-[2-(2-Ethoxy-pyrimidin-5-yl)-6-trifluoromethyl-1,2,3,4-tetrahydro-isoquinolin-8-yl]-2-methyl-piperazin-1-yl}-2-imidazo[4,5-b]pyridin-3-yl-ethanone This compound was synthesized in three steps following a procedure analogous to that of Example 103 steps 103.1 to 103.3, intermediate 134.3 replacing intermediate 60.2 and 5-bromo-2-ethoxypyrimidine replacing 2-bromo-5-(trifluoromethyl)pyridine in step 103.1, using a 3/1 mixture of 4M HCl in dioxane/EtOH instead of 4M HCl in dioxane in step 103.2. The final compound was separated from the second regioisomer after the last step analogous to step 103.3 by preparative LC-MS (111). LC-MS (B): $t_R$=0.88 min; [M+H]$^+$: 581.32. $^1$H-NMR (CDCl$_3$): 8.42 (d, 1H, 4.5 Hz); 8.33 (s, 1H); 8.27 (s, 2H); 8.15 (d, 1H, 7.8 Hz); 7.31 (dd, 1H, 4.8 Hz and 7.8 Hz); 7.27 (s, 1H); 7.20 (s, 1H); 5.31 (m, 1H); 5.18 (m, 1H); 4.88 (m, 0.5H); 4.50 (m, 3H); 4.39 (q, 2H, 7.0 Hz); 3.99 (m, 0.5H); 3.78 (m, 0.5H); 3.54 (m, 2H); 3.26 (m, 0.5H); 3.08 (m, 2H); 3.13-2.89 (m, 4H); 1.66 (s, 1.5H); 1.50 (d, 1.5H, 5.5 Hz); 1.45 (t, 3H, 7.0 Hz). Roesy signal seen between proton at 7.27 ppm and proton at 3.08 ppm, and between proton at 7.20 ppm and protons at 3.13-2.89 ppm.

Example 135: 8-[(R)-3-Methyl-4-(2-pyrazol-1-yl-acetyl)-piperazin-1-yl]-3,4-dihydro-1H-isoquinoline-2-carboxylic acid benzyl ester This compound was prepared using a method analogous to that of Example 1 step 1.6, 2-(1H-pyrazol-1-yl)acetic acid replacing (3,5-dimethyl-1H-pyrazol-1-yl)acetic acid and intermediate 60.4 replacing intermediate 1.5. LC-MS (A): $t_R$=1.14 min; [M+H]$^+$: 474.4.

Example 136: 8-{(R)-4-[2-(3,5-Dimethyl-[1,2,4]triazol-1-yl)-acetyl]-3-methyl-piperazin-1-yl}-3,4-dihydro-1H-isoquinoline-2-carboxylic acid benzyl ester This compound was prepared using a method analogous to that of Example 1 step 1.6, (3,5-dimethyl-[1,2,4]triazol-1-yl)-acetic acid replacing (3,5-dimethyl-1H-pyrazol-1-yl) acetic acid and intermediate 60.4 replacing intermediate 1.5. LC-MS (A): $t_R$=1.04 min; [M+H]$^+$: 503.4.

Example 137: 8-[4-(2-Imidazo[4,5-b]pyridin-3-yl-acetyl)-piperazin-1-yl]-3,4-dihydro-1H-isoquinoline-2-carboxylic acid benzyl ester 137.1. 8-(4-tert-Butoxycarbonyl-piperazin-1-yl)-3,4-dihydro-1H-isoquinoline-2-carboxylic acid benzyl ester This compound was synthesized in three steps following a procedure analogous to that of Example 60 steps 60.1 to 60.3, 1-Boc-piperazine replacing (R)-1-N-Boc-2-methylpiperazine in step 60.1. LC-MS (B): $t_R$=1.04 min; [M+H]$^+$: 452.55.

137.2. 8-Piperazin-1-yl-3,4-dihydro-1H-isoquinoline-2-carboxylic acid benzyl ester A mixture of intermediate 137.1 (1.65 g) in EA (8.3 mL) and HCl (4M in dioxane, 5.5 mL) was stirred at RT for 48 h. It was cooled in an ice bath and NaHCO$_3$ solid and water were slowly added. The resulting mixture was extracted with EA, dried (MgSO$_4$) and concentrated. The crude was purified by CC (Biotage; first purification: SNAP 28 g KP-NH cartridge, solvent A: DCM; solvent B: MeOH; gradient in % B: 1 for 4CV, 1 to 10 over 10CV, 10 for 2CV, 20 for 3CV; second purification: SNAP 11 g KP-NH cartridge, solvent A: Hept; solvent B: EA; gradient in % B: 80 for 4CV, 80 to 100 over 1CV, 100 for 5CV, then DCM/MeOH 8/2 for 5CV; third purification: SNAP 10 g cartridge, solvent A: Hept; solvent B: EA; gradient in % B: 12 for 4CV, 12 to 100 over 10CV, 100 for 2CV, then MeOH for 15CV) to afford 166 mg of beige powder. LC-MS (B): $t_R$=0.71 min; [M+H]$^+$: 352.44.

137.3. 8-[4-(2-Imidazo[4,5-b]pyridin-3-yl-acetyl)-piperazin-1-yl]-3,4-dihydro-1H-isoquinoline-2-carboxylic acid benzyl ester To a mixture of imidazo[4,5-b]pyridin-3-yl-acetic acid (83.2 mg) in DCM (4 mL) was added HOBT (114 mg), followed by EDCI (139 mg), intermediate 137.2 (165 mg) and DIPEA (0.265 mL). The reaction mixture was stirred at RT overnight. DCM/NaHSO$_4$ (1M) was added and the phases were separated. The org. phase was washed with sat. NaHCO$_3$, dried (Na$_2$SO$_4$) and evaporated in vacuo. The residue was purified by preparative LC-MS (VIII) to afford 168 mg of white powder. LC-MS (A): $t_R$=1.08 min; [M+H]$^+$: 511.4.

Example 138: 8-[4-(2-Pyrrolo[2,3-b]pyridin-1-yl-acetyl)-piperazin-1-yl]-3,4-dihydro-1H-isoquinoline-2-carboxylic acid benzyl ester This compound was prepared using a method analogous to that of Example 137 step 137.3, 2-(1H-pyrrolo[2,3-b]pyridin-1-yl)acetic acid replacing imidazo[4,5-b]pyridin-3-yl-acetic acid. LC-MS (A): $t_R$=1.23 min; [M+H]$^+$: 510.4.

Example 139: 8-{4-[2-(3-Methyl-2-oxo-2,3-dihydro-benzoimidazol-1-yl)-acetyl]-piperazin-1-yl}-3,4-dihydro-1H-isoquinoline-2-carboxylic acid benzyl ester This compound was prepared using a method analogous to that of Example 137 step 137.3, (3-methyl-2-oxo-2,3-dihydro-benzoimidazol-1-yl)-acetic acid replacing imidazo[4,5-b]pyridin-3-yl-acetic acid. LC-MS (A): $t_R$=1.21 min; [M+H]$^+$: 540.4.

Example 140: 1-{2-[4-(2-Benzoyl-1,2,3,4-tetrahydro-isoquinolin-8-yl)-piperazin-1-yl]-2-oxo-ethyl}-3-methyl-1,3-dihydro-benzoimidazol-2-one

140.1. 1-Methyl-3-{2-oxo-2-[4-(1,2,3,4-tetrahydro-isoquinolin-8-yl)-piperazin-1-yl]-ethyl}-1,3-dihydro-benzoimidazol-2-one This compound was synthesized using a method analogous to that of Example 61 step 61.1, Example 139 replacing intermediate 60.5. LC-MS (B): $t_R$=1.04 min; [M+H]$^+$: 452.55.

140.2. 1-{2-[4-(2-Benzoyl-1,2,3,4-tetrahydro-isoquinolin-8-yl)-piperazin-1-yl]-2-oxo-ethyl}-3-methyl-1,3-dihydro-benzoimidazol-2-one To an ice-cold solution of intermediate 140.1 (40 mg) in DCM (1 mL) was added DIPEA (0.02 mL) and benzoyl chloride (0.012 mL). The reaction mixture was stirred at 0° C. for 2 h, MeOH was added and the solvents were removed in vacuo. The residue was purified by preparative LC-MS (VIII) to afford 23 mg of white powder. LC-MS (A): $t_R$=1.05 min; [M+H]$^+$: 510.4.

Example 141: 1-Methyl-3-{2-oxo-2-[4-(2-phenylacetyl-1,2,3,4-tetrahydro-isoquinolin-8-yl)-piperazin-1-yl]-ethyl}-1,3-dihydro-benzoimidazol-2-one This compound was prepared using a method analogous to that of Example 140 step 140.2, phenylacetyl chloride replacing benzoyl chloride. LC-MS (A): $t_R$=1.07 min; [M+H]$^+$: 524.4.

Example 142: 2-Imidazo[4,5-b]pyridin-3-yl-1-[4-(2-phenylmethanesulfonyl-1,2,3,4-tetrahydro-isoquinolin-8-yl)-piperazin-1-yl]-ethanone

142.1. 2-Imidazo[4,5-b]pyridin-3-yl-1-[4-(1,2,3,4-tetrahydro-isoquinolin-8-yl)-piperazin-1-yl]-ethanone This compound was synthesized using a method analogous to that of Example 61 step 61.1, Example 139 replacing intermediate 60.5. LC-MS (B): $t_R$=0.51 min; [M+H]$^+$: 377.36.

142.2. 2-Imidazo[4,5-b]pyridin-3-yl-1-[4-(2-phenylmethanesulfonyl-1,2,3,4-tetrahydro-isoquinolin-8-yl)-piperazin-1-yl]-ethanone To an ice-cold solution of intermediate 142.1 (25 mg) in DCM (1 mL) was added DIPEA (0.012 mL) followed by phenylmethanesulfonyl chloride (12.7 mg). The reaction mixture was stirred at 0° C. for 2 h and water was added. The layers were separated and the organic phase was evaporated in vacuo. The residue was purified by preparative LC-MS (VIII) to afford 13.7 mg of white powder. LC-MS (A): $t_R$=0.99 min; [M+H]$^+$: 531.4.

Example 143: 1-{(R)-4-[2-(4-Chloro-benzyl)-1,2,3,4-tetrahydro-isoquinolin-8-yl]-2-methyl-piperazin-1-yl}-2-imidazo[4,5-b]pyridin-3-yl-ethanone To a solution of intermediate 61.1 (50 mg) in EtOH (1 mL) was added TEA (0.036 mL) followed by 4-chlorobenzyl bromide (27.1 mg). The reaction mixture was stirred at RT overnight. DCM and aq. NaHCO$_3$ were added and the layers were separated. The org. phase was dried (Na$_2$SO$_4$), filtered off and evaporated in vacuo. The residue was purified by preparative LC-MS(II) to afford 15.4 mg of white powder. LC-MS (A): $t_R$=0.61 min; [M+H]$^+$: 515.4.

Example 144: 5-Bromo-8-[(R)-4-(2-imidazo[4,5-b]pyridin-3-yl-acetyl)-3-methyl-piperazin-1-yl]-3,4-dihydro-1H-isoquinoline-2-carboxylic acid benzyl ester

144.1. 5-Bromo-8-((R)-4-tert-butoxycarbonyl-3-methyl-piperazin-1-yl)-3,4-dihydro-1H-isoquinoline-2-carboxylic acid benzyl ester To a solution of intermediate 60.3 (1 g) in MeCN (20 mL) was added NBS (394 mg). The resulting mixture was stirred at RT for 1 h. DCM and aq. NaHCO$_3$ were added. The phases were separated and the aq. phase was extracted with DCM. The combined org. layers were dried (Na$_2$SO$_4$), filtered off and evaporated in vacuo. The residue was purified by CC (Biotage, SNAP 25 g cartridge, solvent A: Hept; solvent B: EA; gradient in % B: 12 for 4CV, 12 to 100 over 10CV, 100 for 2CV) to afford 674 mg of yellow oil. LC-MS (B): $t_R$=1.11 min; [M+H]$^+$: 543.95. $^1$H-NMR (CD$_3$CN): 7.47

(d, 1H, 8.6 Hz); 7.36 (m, 5H); 6.92 (d, 1H, 8.6 Hz); 5.13 (s, 2H); 4.71 (br s, 2H); 4.22 (br s, 1H); 3.87 (br s, 2H); 3.72 (m, 1H); 3.65 (br s, 1H); 3.19 (brs, 1H); 2.85 (m, 2H); 2.77 (m, 2H+1H); 2.67 (m, 1H); 1.48 (s, 9H); 1.38 (brs, 1.5H); 1.20 (br s, 1.5H). Roesy signal seen between proton at 6.92 ppm and protons at 2.77 ppm and 2.67 ppm.

144.2. 5-Bromo-8-((R)-3-methyl-piperazin-1-yl)-3,4-dihydro-1H-isoquinoline-2-carboxylic acid benzyl ester, hydrochloride salt This compound was synthesized using a method analogous to that of Example 1 step 1.5, intermediate 144.1 replacing intermediate 1.4. LC-MS (B): $t_R$=0.76 min; [M+H]$^+$: 443.91.

144.3. 5-Bromo-8-[(R)-4-(2-imidazo[4,5-b]pyridin-3-yl-acetyl)-3-methyl-piperazin-1-yl]-3,4-dihydro-1H-isoquinoline-2-carboxylic acid benzyl ester This compound was prepared using a method analogous to that of Example 1 step 1.6, imidazo[4,5-b]pyridin-3-yl-acetic acid replacing (3,5-dimethyl-1H-pyrazol-1-yl)acetic acid and intermediate 144.2 replacing intermediate 1.5. LC-MS (A): $t_R$=1.23 min; [M+H]$^+$: 603.3.

Example 145: 8-[(R)-4-(2-Imidazo[4,5-b]pyridin-3-yl-acetyl)-3-methyl-piperazin-1-yl]-5-trifluoromethyl-3,4-dihydro-1H-isoquinoline-2-carboxylic acid benzyl ester

145.1. 8-((R)-4-tert-Butoxycarbonyl-3-methyl-piperazin-1-yl)-5-(4,4,5,5-tetramethyl-[1,3, 2]dioxaborolan-2-yl)-3,4-dihydro-1H-isoquinoline-2-carboxylic acid benzyl ester To a solution of intermediate 144.1 (50 mg) in dioxane (1 mL) under argon was added bis(pinacolato)diboron (48 mg), followed by [1,1-bis(diphenylphosphino)ferrocene]-dichloropalladium(II), complex with DCM (7.5 mg) and KOAc (27 mg). The resulting mixture was stirred at 80° C. overnight. Water/EA was added, the layers were separated and the aq. phase was extracted with EA. The combined org. phases were dried (Na$_2$SO$_4$), filtered off and evaporated in vacuo to afford 54 mg of brown oil that was used directly in the next step. LC-MS (B): $t_R$=1.15 min; [M+H]$^+$: 592.19.

145.2. 8-((R)-4-tert-Butoxycarbonyl-3-methyl-piperazin-1-yl)-5-trifluoromethyl-3,4-dihydro-1H-isoquinoline-2-carboxylic acid benzyl ester To a solution of intermediate 145.1 (54 mg) in diethylene glycol dimethyl ether (0.5 mL) under argon was added CuI (0.9 mg), 1,10-phenanthroline (1.6 mg), 3,3-dimethyl-1-(trifluoromethyl)-1,2-benziodoxole (38 mg) and K$_2$CO$_3$ (2.5 mg). The resulting mixture was stirred at 35° C. overnight. Water/DCM was added, the layers were separated and the aq. phase was extracted with DCM. The combined org. phases were dried (Na$_2$SO$_4$), filtered off and evaporated in vacuo. The residue was purified by preparative LC-MS (II) to afford 5 mg of white powder. LC-MS (B): $t_R$=1.11 min; [M+H]$^+$: 534.08. $^{19}$F-NMR (CDCl$_3$): −60.14 ppm (d, 34.1 Hz).

145.3. 8-((R)-3-Methyl-piperazin-1-yl)-5-trifluoromethyl-3,4-dihydro-1H-isoquinoline-2-carboxylic acid benzyl ester, hydrochloride salt This compound was synthesized using a method analogous to that of Example 1 step 1.5, intermediate 145.2 replacing intermediate 1.4. LC-MS (B): $t_R$=0.78 min; [M+H]$^+$: 434.01.

145.4. 8-[(R)-4-(2-Imidazo[4,5-b]pyridin-3-yl-acetyl)-3-methyl-piperazin-1-yl]-5-trifluoromethyl-3,4-dihydro-1H-isoquinoline-2-carboxylic acid benzyl ester This compound was prepared using a method analogous to that of Example 1 step 1.6, imidazo[4,5-b]pyridin-3-yl-acetic acid replacing (3,5-dimethyl-1H-pyrazol-1-yl)acetic acid and intermediate 145.3 replacing intermediate 1.5. LC-MS (A): $t_R$=1.22 min; [M+H]$^+$: 593.4.

Example 146: 5-Cyano-8-[(R)-4-(2-imidazo[4,5-b]pyridin-3-yl-acetyl)-3-methyl-piperazin-1-yl]-3,4-dihydro-1H-isoquinoline-2-carboxylic acid benzyl ester

146.1. 8-((R)-4-tert-Butoxycarbonyl-3-methyl-piperazin-1-yl)-5-cyano-3,4-dihydro-1H-isoquinoline-2-carboxylic acid benzyl ester To a solution of intermediate 144.1 (50 mg) in NMP (1 mL) under argon was added CuCN (8.4 mg). The resulting mixture was stirred at 130° C. overnight. Additional equivalents of CuCN were added, the reaction mixture was further stirred at 130° C. for 8 h. Additional equivalents of CuCN were added, the reaction mixture was further stirred at 130° C. overnight. After cooling down, brine was added and the mixture was stirred at RT for 30 min. After filtration, the resulting mixture was extracted with Hept and the aq. layer was extracted with EA. The combined org. layers were dried (Na$_2$SO$_4$), filtered off and evaporated in vacuo to afford 45 mg of brown oil that was used directly in the next step. LC-MS (B): $t_R$=1.05 min; [M+H]$^+$: 491.01.

146.2. 5-Cyano-8-((R)-3-methyl-piperazin-1-yl)-3,4-dihydro-1H-isoquinoline-2-carboxylic acid benzyl ester, hydrochloride salt This compound was synthesized using a method analogous to that of Example 1 step 1.5, intermediate 146.1 replacing intermediate 1.4. LC-MS (B): $t_R$=0.70 min; [M+H]$^+$: 391.01.

146.3. 5-Cyano-8-[(R)-4-(2-imidazo[4,5-b]pyridin-3-yl-acetyl)-3-methyl-piperazin-1-yl]-3,4-dihydro-1H-isoquinoline-2-carboxylic acid benzyl ester This compound was prepared using a method analogous to that of Example 1 step 1.6, imidazo[4,5-b]pyridin-3-yl-acetic acid replacing (3,5-dimethyl-1H-pyrazol-1-yl)acetic acid and intermediate 146.2 replacing intermediate 1.5. LC-MS (A): $t_R$=1.04 min; [M+H]$^+$: 550.4.

Example 147: 1-{(R)-4-[5,6-Difluoro-2-(2-trifluoromethyl-pyrimidin-5-yl)-1,2,3,4-tetrahydro-isoquinolin-8-yl]-2-methyl-piperazin-1-yl}-2-(3,5-dimethyl-[1,2,4]triazol-1-yl)-ethanone

147.1. 1-(5, 6-Difluoro-3,4-dihydro-1H-isoquinolin-2-yl)-2,2,2-trifluoro-ethanone This compound was prepared using a method analogous to that of Example 1 step 1.2, 5,6-difluoro-1,2,3,4-tetrahydroisoquinoline replacing intermediate 1.1. LC-MS (B): $t_R$=0.89 min; [M+MeCN+H]$^+$: 307.01.

147.2. 1-(8-Bromo-5, 6-difluoro-3,4-dihydro-1H-isoquinolin-2-yl)-2,2,2-trifluoro-ethanone To a solution of intermediate 147.1 (110 mg) in DCM (2.2 mL) was added FeCl$_3$ (142 mg) and the mixture was cooled down to 0° C. Br$_2$ (0.047 mL) was added dropwise and the resulting mixture was stirred at RT overnight. DCM and crushed ice were added and the mixture was vigorously stirred for 5 min. The layers were separated and the aq. phase was extracted with DCM. The combined org. layers were washed with aq. NaHCO$_3$, aq. NaHSO$_3$ (10%) and brine, were dried (Na$_2$SO$_4$) and evaporated off. The residue was purified by CC (Biotage, SNAP 25 g cartridge, solvent A: Hept; solvent B: EA; gradient in % B: 8 for 4CV, 8 to 66 over 10CV, 66 for 6CV) to afford 83 mg of yellow oil. LC-MS (B): $t_R$=0.95 min. $^1$H-NMR (CDCl$_3$): 7.38 (m, 1H); 4.71 (m, 2H); 3.88 (dt, 2H, 6.1 Hz and 26.5 Hz); 2.99 (m, 2H).

147.3. (R)-4-[5, 6-Difluoro-2-(2,2,2-trifluoro-acetyl)-1,2,3,4-tetrahydro-isoquinolin-8-yl]-2-methyl-piperazine-1-carboxylic acid tert-butyl ester This compound was prepared using a method analogous to that of Example 1 step 1.4, intermediate 147.2 replacing intermediate 1.3. LC-MS (B): $t_R$=1.05 min; [M+H]$^+$: 464.07.

147.4. (R)-4-(5, 6-Difluoro-1,2,3,4-tetrahydro-isoquinolin-8-yl)-2-methyl-piperazine-1-carboxylic acid tert-butyl ester This compound was prepared using a method analogous to that of Example 1 step 1.7, intermediate 147.3 replacing intermediate 1.6. LC-MS (B): $t_R$=0.72 min; [M+H]$^+$: 368.24.

147.5. 1-{(R)-4-[5, 6-Difluoro-2-(2-trifluoromethyl-pyrimidin-5-yl)-1,2,3,4-tetrahydro-isoquinolin-8-yl]-2-methyl-piperazin-1-yl}-2-(3, 5-dimethyl-[1,2,4]triazol-1-yl)-ethanone This compound was synthesized in three steps following a procedure analogous to that of Example 103 steps 103.1 to 103.3, 5-bromo-2-(trifluoromethyl)pyrimidine replacing 2-bromo-5-(trifluoromethyl)pyridine in step 103.1, and (3,5-dimethyl-[1,2,4]triazol-1-yl)-acetic acid replacing imidazo[4,5-b]pyridin-3-yl-acetic acid in step 103.3. LC-MS (B): $t_R$=0.84 min; [M+H]$^+$: 551.1.

II. Biological Assays

FLIPR Assay:

The bioactivity of compounds is tested in a fluorometric imaging plate reader (FLIPR: Molecular Devices) using engineered CHO-K1 cells expressing the human CXCR3A (GenBank: AY242128) coupled to a G protein (Galpha(16)). Cells are plated the day prior to bioassay in F12 medium supplemented with 10% FBS and G418 and hygromycin antibiotics to maintain recombinant selection. At the day of bioassay, cells are washed and dye loaded for one hour with Fluo-4-AM (Invitrogen) in Hanks Balanced Salt Solution (Invitrogen), buffered with 20 mM Hepes at pH 7.4 and sodium bicarbonate (0.038%), containing 5 mM probenecid. This buffer, but lacking the dye and containing probenecid at a concentration of 2.5 mM, is also used for washing steps (wash buffer); or lacking both dye and probenecid but supplemented with 0.1% BSA for compound dilution steps (dilution buffer). Cells are washed free of excess dye and 60 microliter of wash buffer is added. Stock solutions of test compounds are made up at a concentration of 10 mM in DMSO, and serially diluted in dilution buffer to concentrations required for inhibition dose response curves. After a 10 minute incubation period at 37° C., 10 microliters of each compound dilution are transferred from a compound plate to the plate containing the recombinant cells in the FLIPR instrument according to the manufacturer's instructions. Following basal readings, 10 microliter CXCL10 agonist at a concentration of 20 nM (from Peprotech) is added, again using the FLIPR instrument. Changes in fluorescence are monitored before and after addition of the test compounds. Emission peak values above base level after CXCL10 addition are exported after base line subtraction.

The calculated IC$_{50}$ values may fluctuate depending on the daily assay performance. Fluctuations of this kind are known to those skilled in the art. In the case where IC$_{50}$ values have been determined several times for the same compound, mean values are given. Data are shown in Table 1.

TABLE 1

| Example No | FLIPR: IC$_{50}$ (nM) |
| --- | --- |
| 1 | 4.47 |
| 2 | 6.07 |
| 3 | 15.1 |
| 4 | 20.6 |
| 5 | 11.0 |
| 6 | 18.1 |
| 7 | 29.2 |
| 8 | 8.88 |
| 9 | 13.7 |
| 10 | 9.45 |
| 11 | 6.58 |
| 12 | 9.39 |
| 13 | 8.48 |
| 14 | 27.7 |
| 15 | 3.58 |
| 16 | 6.19 |
| 17 | 9.20 |
| 18 | 13.0 |
| 19 | 11.7 |
| 20 | 7.77 |
| 21 | 29.9 |
| 22 | 10.7 |
| 23 | 17.1 |
| 24 | 3.70 |
| 25 | 24.0 |
| 26 | 98.5 |
| 27 | 908 |
| 28 | 2.40 |
| 29 | 30.5 |
| 30 | 13.8 |
| 31 | 11.5 |
| 32 | 9.83 |
| 33 | 10.9 |
| 34 | 16.7 |
| 35 | 30.8 |
| 36 | 6.27 |
| 37 | 30.9 |
| 38 | 15.8 |
| 39 | 73.5 |
| 40 | 49.0 |
| 41 | 51.4 |
| 42 | 8.29 |
| 43 | 38.6 |
| 44 | 12.0 |
| 45 | 12.7 |
| 46 | 4.37 |
| 47 | 7.27 |
| 48 | 1.40 |
| 49 | 3.56 |
| 50 | 2.26 |

TABLE 1-continued

| Example No | FLIPR: IC$_{50}$ (nM) |
|---|---|
| 51 | 4.93 |
| 52 | 4.10 |
| 53 | 6.15 |
| 54 | 6.22 |
| 55 | 10.0 |
| 56 | 8.14 |
| 57 | 26.5 |
| 58 | 16.9 |
| 59 | 12.3 |
| 60 | 7.94 |
| 61 | 223 |
| 62 | 121 |
| 63 | 668 |
| 64 | 188 |
| 65 | 483 |
| 66 | 304 |
| 67 | 614 |
| 68 | 599 |
| 69 | 21.7 |
| 70 | 55.5 |
| 71 | 80.2 |
| 72 | 92.2 |
| 73 | 111 |
| 74 | 46.6 |
| 75 | 17.0 |
| 76 | 82.4 |
| 77 | 92.3 |
| 78 | 216 |
| 79 | 570 |
| 80 | 199 |
| 81 | 65.1 |
| 82 | 88.1 |
| 83 | 450 |
| 84 | 99.7 |
| 85 | 866 |
| 86 | 686 |
| 87 | 5420 |
| 88 | 1910 |
| 89 | 955 |
| 90 | 11.2 |
| 91 | 8.01 |
| 92 | 0.97 |
| 93 | 7.55 |
| 94 | 61.9 |
| 95 | 7.80 |
| 96 | 25.5 |
| 97 | 4.38 |
| 98 | 11.6 |
| 99 | 8.30 |
| 100 | 1.25 |
| 101 | 14.7 |
| 102 | 29.1 |
| 103 | 20.7 |
| 104 | 9.71 |
| 105 | 20.3 |
| 106 | 5.46 |
| 107 | 1.74 |
| 108 | 32.6 |
| 109 | 12.5 |
| 110 | 0.85 |
| 111 | 4.83 |
| 112 | 2.98 |
| 113 | 12.2 |
| 114 | 9.53 |
| 115 | 13.3 |
| 116 | 15.1 |
| 117 | 3.70 |
| 118 | 6.49 |
| 119 | 10.9 |
| 120 | 2.03 |
| 121 | 3.39 |
| 122 | 27.9 |
| 123 | 4.71 |
| 124 | 34.4 |
| 125 | 47.4 |
| 126 | 3.98 |
| 127 | 33.1 |
| 128 | 7.94 |
| 129 | 3.10 |
| 130 | 5.70 |
| 131 | 24.3 |
| 132 | 58.9 |
| 133 | 5.42 |
| 134 | 52.1 |
| 135 | 116 |
| 136 | 33.2 |
| 137 | 9.10 |
| 138 | 12.4 |
| 139 | 21.7 |
| 140 | 51.2 |
| 141 | 190 |
| 142 | 65.4 |
| 143 | 465 |
| 144 | 85.7 |
| 145 | 25.6 |
| 146 | 15.6 |
| 147 | 8.58 |

The invention claimed is:
1. A compound of Formula (I)

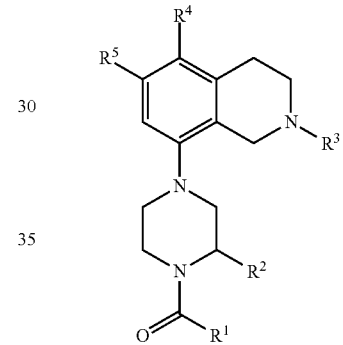

Formula (I)

wherein
R$^1$ represents heteroaryl-(C$_{1-2}$)alkyl, wherein the heteroaryl is a 5- to 10-membered monocyclic or bicyclic aromatic ring comprising 1, 2 or 3 heteroatoms independently selected from oxygen, nitrogen or sulphur, and wherein the heteroaryl is unsubstituted or mono- or di-substituted with (C$_{1-4}$)alkyl; or heterocyclyl-(C$_{1-2}$)alkyl, wherein the heterocyclyl is a 5- or 6-membered monocyclic non-aromatic ring comprising one or two nitrogen atoms which is annulated to a phenyl or pyridinyl ring, and wherein the heterocyclyl is unsubstituted or mono- or di-substituted wherein the substituents are independently selected from (C$_{1-4}$)alkyl or oxo;
R$^2$ represents hydrogen or methyl;
R$^3$ represents aryl, wherein the aryl is a phenyl- or naphthyl-group, which groups are independently unsubstituted or mono- or di-substituted wherein the substituents are independently selected from halogen, (C$_{1-4}$)alkyl, (C$_{1-4}$)alkoxy, (C$_{1-2}$)fluoroalkyl, (C$_{1-2}$)fluoroalkoxy or cyano; aryl-(C$_{1-2}$)alkyl, wherein the aryl is a phenyl- or naphthyl-group, which groups are independently unsubstituted or mono-substituted with halogen; heteroaryl, wherein the heteroaryl is a 5- to 10-membered monocyclic or bicyclic aromatic ring comprising 1, 2 or 3 heteroatoms independently selected from oxygen, nitrogen or sulphur, and wherein the heteroaryl is unsubstituted or mono- or di-substituted wherein the substituents are independently selected from halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy, di-$(C_{1-2})$alkyl-amino, hydroxy, cyano, phenyl, pyridinyl or heteroaryl-$(C_{1-2})$alkyl, wherein the heteroaryl is a 5- or 6-membered monocyclic aromatic ring comprising 1 or 2 heteroatoms independently selected from oxygen, nitrogen or sulphur; aryl-$(C_{1-2})$alkyl-sulfonyl, wherein the aryl is a phenyl- or naphthyl-group; or $R^6$-carbonyl;

$R^4$ represents hydrogen, halogen, $(C_{1-2})$fluoroalkyl or cyano;

$R^5$ represents hydrogen, halogen or $(C_{1-2})$fluoroalkyl; and $R^6$ represents $(C_{1-4})$alkyl; $(C_{3-6})$cycloalkyl, wherein the cycloalkyl is unsubstituted or mono-substituted with phenyl; $(C_{5-6})$cycloalkyl, wherein the cycloalkyl is annulated to a phenyl ring; $(C_{1-2})$alkoxy-$(C_{1-2})$alkyl; aryl, wherein the aryl is a phenyl- or naphthyl-group, which groups are independently unsubstituted or mono- or di-substituted wherein the substituents are independently selected from halogen, $(C_{1-4})$alkyl, $(C_{1-4})$alkoxy, $(C_{1-2})$fluoroalkyl or di-$(C_{1-2})$alkyl-amino; aryl-$(C_{1-2})$alkyl, wherein the aryl is a phenyl- or naphthyl-group, which groups are independently unsubstituted or mono- or di-substituted wherein the substituents are independently selected from halogen or $(C_{1-4})$alkoxy; aryloxy-$(C_{1-2})$alkyl, wherein the aryl is a phenyl- or naphthyl-group; aryl-$(C_{1-2})$alkoxy, wherein the aryl is a phenyl- or naphthyl-group; heterocyclyl-$(C_{1-2})$alkyl, wherein the heterocyclyl is a 5- or 6-membered monocyclic non-aromatic ring comprising one or two heteroatoms independently selected from oxygen or nitrogen; heteroaryl, wherein the heteroaryl is a 5- to 10-membered monocyclic or bicyclic aromatic ring comprising 1, 2 or 3 heteroatoms independently selected from oxygen, nitrogen or sulphur, and wherein the heteroaryl is unsubstituted or mono-substituted with $(C_{1-4})$alkyl; or heteroaryl-$(C_{1-2})$alkyl, wherein the heteroaryl is a 5- to 10-membered monocyclic or bicyclic aromatic ring comprising 1, 2 or 3 heteroatoms independently selected from oxygen, nitrogen or sulphur;

or a salt thereof.

2. The compound according to claim 1, wherein $R^1$ represents heteroaryl-methyl, wherein the heteroaryl is a 5- to 10-membered monocyclic or bicyclic aromatic ring comprising 1, 2 or 3 nitrogen atoms, and wherein the heteroaryl is unsubstituted or mono- or di-substituted with $(C_{1-4})$alkyl; or heterocyclyl-methyl, wherein the heterocyclyl is a 5- or 6-membered monocyclic non-aromatic ring comprising one or two nitrogen atoms which is annulated to a phenyl or pyridinyl ring, and wherein the heterocyclyl is unsubstituted or mono- or di-substituted wherein the substituents are independently selected from $(C_{1-4})$alkyl or oxo;

$R^2$ represents hydrogen or methyl;

$R^3$ represents aryl, wherein the aryl is a phenyl- or naphthyl-group, which groups are independently unsubstituted or mono- or di-substituted wherein the substituents are independently selected from halogen, $(C_{1-4})$alkoxy, $(C_{1-2})$fluoroalkyl, $(C_{1-2})$fluoroalkoxy or cyano; or heteroaryl, wherein the heteroaryl is a 5- to 10-membered monocyclic or bicyclic aromatic ring comprising 1, 2 or 3 heteroatoms independently selected from oxygen, nitrogen or sulphur, and wherein the heteroaryl is unsubstituted or mono- or di-substituted wherein the substituents are independently selected from halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy, di-$(C_{1-2})$alkyl-amino, cyano, phenyl, pyridinyl or 1H-pyrazol-1-yl-methyl;

$R^4$ represents hydrogen, halogen, $(C_{1-2})$fluoroalkyl or cyano; and $R^5$ represents hydrogen or halogen;

or a salt thereof.

3. The compound according to claim 1, wherein $R^1$ represents heteroaryl-methyl, wherein the heteroaryl is a 5- to 10-membered monocyclic or bicyclic aromatic ring comprising 1, 2 or 3 nitrogen atoms, and wherein the heteroaryl is unsubstituted or mono- or di-substituted with $(C_{1-4})$alkyl;

or a salt thereof.

4. The compound according to claim 1, wherein $R^3$ represents phenyl which is unsubstituted or mono-substituted with halogen, $(C_{1-4})$alkoxy, $(C_{1-2})$fluoroalkyl, $(C_{1-2})$fluoroalkoxy or cyano; or heteroaryl, wherein the heteroaryl is selected from pyridinyl or pyrimidinyl, and wherein the heteroaryl is unsubstituted or mono-substituted with halogen, $(C_{1-4})$alkyl, $(C_{3-6})$cycloalkyl, $(C_{1-4})$alkoxy, $(C_{1-2})$fluoroalkyl, $(C_{1-2})$fluoroalkoxy or di-$(C_{1-2})$alkyl-amino;

or a salt thereof.

5. The compound according to claim 1, wherein $R^4$ represents hydrogen, fluoro or trifluoromethyl;

or a salt thereof.

6. The compound according to claim 1, which is a compound of Formula ($I_{Ar}$)

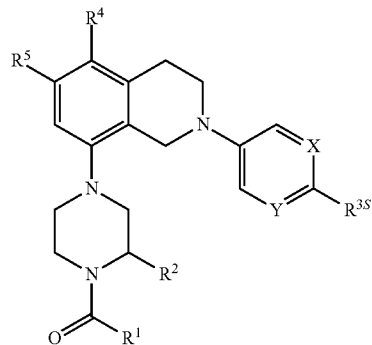

Formula ($I_{Ar}$)

wherein $R^1$ represents heteroaryl-$(C_{1-2})$alkyl, wherein the heteroaryl is a 5- to 10-membered monocyclic or bicyclic aromatic ring comprising 1, 2 or 3 nitrogen atoms, and wherein the heteroaryl is unsubstituted or mono- or di-substituted with $(C_{1-4})$alkyl; or heterocyclyl-$(C_{1-2})$alkyl, wherein the heterocyclyl is a 5- or 6-membered monocyclic non-aromatic ring comprising one or two nitrogen atoms which is annulated to a phenyl or pyridinyl ring, and wherein the heterocyclyl is unsubstituted or mono- or di-substituted wherein the substituents are independently selected from $(C_{1-4})$alkyl or oxo;

$R^2$ represents hydrogen or methyl;

X and Y represent =CH— and R³ˢ represents hydrogen, halogen, (C₁₋₄)alkoxy, (C₁₋₂)fluoroalkyl, (C₁₋₂)fluoroalkoxy or cyano; or X represents =CH— or =N—, Y represents =N— and R³ˢ represents hydrogen, (C₁₋₄)alkyl, (C₃₋₆)cycloalkyl, (C₁₋₄)alkoxy, (C₁₋₂)fluoroalkyl, (C₁₋₂)fluoroalkoxy or di-(C₁₋₂)alkyl-amino;

R⁴ represents hydrogen, halogen or (C₁₋₂)fluoroalkyl; and

R⁵ represents hydrogen, halogen or (C₁₋₂)fluoroalkyl;

or a salt thereof.

7. The compound according to claim 6, wherein

R¹ represents heteroaryl-methyl, wherein the heteroaryl is a 5- to 10-membered monocyclic or bicyclic aromatic ring comprising 2 or 3 nitrogen atoms, and wherein the heteroaryl is unsubstituted or mono- or di-substituted with methyl;

R² represents hydrogen or methyl;

X represents =N—;

Y represents =N—;

R³ˢ represents hydrogen, (C₁₋₄)alkyl, (C₃₋₆)cycloalkyl, (C₁₋₄)alkoxy, (C₁₋₂)fluoroalkyl, (C₁₋₂)fluoroalkoxy or di-(C₁₋₂)alkyl-amino;

R⁴ represents hydrogen, fluoro or trifluoromethyl; and

R⁵ represents hydrogen or fluoro;

or a salt thereof.

8. The compound according to claim 6, wherein

R¹ represents heteroaryl-methyl, wherein the heteroaryl is selected from pyrazolyl, triazolyl, pyrrolo[2,3-b]pyridinyl, pyrazolo[3,4-b]pyridinyl, or imidazo[4,5-b]pyridinyl, and wherein the heteroaryl is unsubstituted or mono- or di-substituted with methyl;

or a salt thereof.

9. The compound according to claim 6, wherein

X represents =N— and Y represents =N—;

or a salt thereof.

10. The compound according to claim 7, wherein

R¹ represents heteroaryl-methyl, wherein the heteroaryl is selected from pyrazolyl, triazolyl, pyrrolo[2,3-b]pyridinyl, pyrazolo[3,4-b]pyridinyl, or imidazo[4,5-b]pyridinyl, and wherein the heteroaryl is unsubstituted or mono- or di-substituted with methyl;

or a salt thereof.

11. The compound according to claim 1, wherein the compound is:

2-(3,5-Dimethyl-pyrazol-1-yl)-1-{(R)-2-methyl-4-[2-(5-pyrazol-1-ylmethyl-thiazol-2-yl)-5-trifluoromethyl-1,2,3,4-tetrahydro-isoquinolin-8-yl]-piperazin-1-yl}-ethanone;

2-(3,5-Dimethyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone;

2-(3,5-Dimethyl-pyrazol-1-yl)-1-{(R)-4-[2-(4-ethyl-thiazol-2-yl)-5-trifluoromethyl-1,2,3,4-tetrahydro-isoquinolin-8-yl]-2-methyl-piperazin-1-yl}-ethanone;

1-{(R)-4-[2-(4-tert.-Butyl-thiazol-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;

2-(3,5-Dimethyl-pyrazol-1-yl)-1-{(R)-2-methyl-4-[2-(4-pyridin-2-yl-thiazol-2-yl)-5-trifluoromethyl-1,2,3,4-tetrahydro-isoquinolin-8-yl]-piperazin-1-yl}-ethanone;

1-{(R)-4-[2-(5-Chloro-thiazol-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;

2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-thiazole-4-carbonitrile;

2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-thiazole-5-carbonitrile;

2-(3,5-Dimethyl-pyrazol-1-yl)-1-{(R)-2-methyl-4-[2-(6-methyl-benzothiazol-2-yl)-5-trifluoromethyl-1,2,3,4-tetrahydro-isoquinolin-8-yl]-piperazin-1-yl}-ethanone;

2-(3,5-Dimethyl-pyrazol-1-yl)-1-{(R)-4-[2-(6-fluoro-benzothiazol-2-yl)-5-trifluoromethyl-1,2,3,4-tetrahydro-isoquinolin-8-yl]-2-methyl-piperazin-1-yl}-ethanone;

2-(8-{(R)-4-[2-(3,5-Dimethyl-pyrazol-1-yl)-acetyl]-3-methyl-piperazin-1-yl}-5-trifluoromethyl-3,4-dihydro-1H-isoquinolin-2-yl)-benzothiazole-6-carbonitrile;

1-[(R)-4-(2-Benzooxazol-2-yl-5-trifluoromethyl-1,2,3,4-tetrahydro-isoquinolin-8-yl)-2-methyl-piperazin-1-yl]-2-(3,5-dimethyl-pyrazol-1-yl)-ethanone;

1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;

1-{(R)-4-[2-(5-Bromo-pyrimidin-2-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;

1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3,5-dimethyl-pyrazol-1-yl)-ethanone;

2-Imidazo[4,5-b]pyridin-3-yl-1-[(R)-2-methyl-4-(2-phenyl-5-trifluoromethyl-1,2,3,4-tetrahydro-isoquinolin-8-yl)-piperazin-1-yl]-ethanone;

2-Imidazo[4,5-b]pyridin-3-yl-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone;

2-Imidazo[4,5-b]pyridin-3-yl-1-{(R)-4-[2-(3-methoxy-phenyl)-5-trifluoromethyl-1,2,3,4-tetrahydro-isoquinolin-8-yl]-2-methyl-piperazin-1-yl}-ethanone;

1-{(R)-4-[2-(4,6-Dimethoxy-[1,3,5]triazin-2-yl)-5-trifluoromethyl-1,2,3,4-tetrahydro-isoquinolin-8-yl]-2-methyl-piperazin-1-yl}-2-imidazo[4,5-b]pyridin-3-yl-ethanone;

1-{(R)-4-[2-(2-Ethoxy-pyrimidin-5-yl)-5-trifluoromethyl-1,2,3,4-tetrahydro-isoquinolin-8-yl]-2-methyl-piperazin-1-yl}-2-imidazo[4,5-b]pyridin-3-yl-ethanone;

1-{(R)-4-[2-(4-Chloro-phenyl)-5-trifluoromethyl-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(2-propyl-pyrimidin-5-yl)-5-trifluoromethyl-1,2,3,4-tetrahydro-isoquinolin-8-yl]-piperazin-1-yl}-ethanone;

2-(3,5-Dimethyl-[1,2,4]triazol-1-yl)-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone;

2-(3,5-Dimethyl-pyrazol-1-yl)-1-{(R)-4-[2-(2-methoxy-pyrimidin-5-yl)-5-trifluoromethyl-1,2,3,4-tetrahydro-isoquinolin-8-yl]-2-methyl-piperazin-1-yl}-ethanone;

1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-2-pyrazol-1-yl-ethanone;

1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-2-[1,2,3]triazol-2-yl-ethanone;

1-{(R)-4-[2-(2-Methoxy-pyrimidin-5-yl)-5-trifluoromethyl-1,2,3,4-tetrahydro-isoquinolin-8-yl]-2-methyl-piperazin-1-yl}-3-pyrazol-1-yl-propan-1-one;
1-{4-[2-(2-Ethoxy-pyrimidin-5-yl)-5-trifluoromethyl-1,2,3,4-tetrahydro-isoquinolin-8-yl]-piperazin-1-yl}-2-imidazo[4,5-b]pyridin-3-yl-ethanone;
2-(3,5-Dimethyl-pyrazol-1-yl)-1-{4-[2-(2-ethoxy-pyrimidin-5-yl)-5-trifluoromethyl-1,2,3,4-tetrahydro-isoquinolin-8-yl]-piperazin-1-yl}-ethanone;
2-(3,5-Dimethyl-[1,2,4]triazol-1-yl)-1-{4-[2-(2-ethoxy-pyrimidin-5-yl)-5-trifluoromethyl-1,2,3,4-tetrahydro-isoquinolin-8-yl]-piperazin-1-yl}-ethanone;
1-{4-[2-(2-Ethoxy-pyrimidin-5-yl)-5-trifluoromethyl-1,2,3,4-tetrahydro-isoquinolin-8-yl]-piperazin-1-yl}-2-pyrazolo[3,4-b]pyridin-1-yl-ethanone;
1-{4-[2-(2-Ethoxy-pyrimidin-5-yl)-5-trifluoromethyl-1,2,3,4-tetrahydro-isoquinolin-8-yl]-piperazin-1-yl}-2-pyrazolo[3,4-b]pyridin-2-yl-ethanone;
1-(2-{4-[2-(2-Ethoxy-pyrimidin-5-yl)-5-trifluoromethyl-1,2,3,4-tetrahydro-isoquinolin-8-yl]-piperazin-1-yl}-2-oxo-ethyl)-1,3-dihydro-indol-2-one;
1-{(S)-4-[2-(2-Ethoxy-pyrimidin-5-yl)-5-trifluoromethyl-1,2,3,4-tetrahydro-isoquinolin-8-yl]-2-methyl-piperazin-1-yl}-2-imidazo[4,5-b]pyridin-3-yl-ethanone;
2-(3,5-Dimethyl-pyrazol-1-yl)-1-{(S)-4-[2-(2-ethoxy-pyrimidin-5-yl)-5-trifluoromethyl-1,2,3,4-tetrahydro-isoquinolin-8-yl]-2-methyl-piperazin-1-yl}-ethanone;
1-{(S)-4-[2-(2-Ethoxy-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone;
2-(2,3-Dihydro-pyrrolo[2,3-b]pyridin-1-yl)-1-{(S)-4-[2-(2-ethoxy-pyrimidin-5-yl)-5-trifluoromethyl-1,2,3,4-tetrahydro-isoquinolin-8-yl]-2-methyl-piperazin-1-yl}-ethanone;
2-(3,5-Dimethyl-[1,2,4]triazol-1-yl)-1-{(R)-4-[2-(6-fluoro-benzothiazol-2-yl)-5-trifluoromethyl-1,2,3,4-tetrahydro-isoquinolin-8-yl]-2-methyl-piperazin-1-yl}-ethanone;
1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone;
1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-(3-methyl-pyrazol-1-yl)-ethanone;
1-{(R)-4-[2-(6-Fluoro-benzothiazol-2-yl)-5-trifluoromethyl-1,2,3,4-tetrahydro-isoquinolin-8-yl]-2-methyl-piperazin-1-yl}-2-(5-methyl-pyrazol-1-yl)-ethanone;
2-(3,5-Dimethyl-[1,2,4]triazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone;
1-{(R)-2-Methyl-4-[5-trifluoromethyl-2-(4-trifluoromethyl-thiazol-2-yl)-1,2,3,4-tetrahydro-isoquinolin-8-yl]-piperazin-1-yl}-2-pyrazolo[3,4-b]pyridin-1-yl-ethanone;
2-(3-Methyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone;
2-(5-Methyl-pyrazol-1-yl)-1-{(R)-2-methyl-4-[5-trifluoromethyl-2-(4-trifluoromethyl-thiazol-2-yl)-1,2,3,4-tetrahydro-isoquinolin-8-yl]-piperazin-1-yl}-ethanone;
1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3,5-dimethyl-[1,2,4]triazol-1-yl)-ethanone;
1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone;
1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone;
1-{(R)-4-[2-(2-Cyclopropyl-pyrimidin-5-yl)-5-trifluoromethyl-1,2,3,4-tetrahydro-isoquinolin-8-yl]-2-methyl-piperazin-1-yl}-2-(5-methyl-pyrazol-1-yl)-ethanone;
1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3,5-dimethyl-[1,2,4]triazol-1-yl)-ethanone;
1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(3-methyl-pyrazol-1-yl)-ethanone;
1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-(5-methyl-pyrazol-1-yl)-ethanone;
1-{(R)-4-[2-(2-Dimethylamino-pyrimidin-5-yl)-5-trifluoromethyl-1,2,3,4-tetrahydro-isoquinolin-8-yl]-2-methyl-piperazin-1-yl}-2-pyrazolo[3,4-b]pyridin-1-yl-ethanone;
2-(3,5-Dimethyl-[1,2,4]triazol-1-yl)-1-{(R)-4-[2-(2-ethoxy-pyrimidin-5-yl)-5-trifluoromethyl-1,2,3,4-tetrahydro-isoquinolin-8-yl]-2-methyl-piperazin-1-yl}-ethanone;
2-(3,5-Dimethyl-pyrazol-1-yl)-1-{(R)-4-[2-(2-ethoxy-pyrimidin-5-yl)-5-trifluoromethyl-1,2,3,4-tetrahydro-isoquinolin-8-yl]-2-methyl-piperazin-1-yl}-ethanone;
2-(3,5-Dimethyl-pyrazol-1-yl)-1-{(R)-2-methyl-4-[2-(5-phenyl-oxazol-2-yl)-5-trifluoromethyl-1,2,3,4-tetrahydro-isoquinolin-8-yl]-piperazin-1-yl}-ethanone;
1-[(R)-4-(2-Benzothiazol-2-yl-5-trifluoromethyl-1,2,3,4-tetrahydro-isoquinolin-8-yl)-2-methyl-piperazin-1-yl]-2-(3,5-dimethyl-pyrazol-1-yl)-ethanone;
2-(3,5-Dimethyl-[1,2,4]triazol-1-yl)-1-{(R)-4-[2-(2-ethyl-pyrimidin-5-yl)-5-trifluoromethyl-1,2,3,4-tetrahydro-isoquinolin-8-yl]-2-methyl-piperazin-1-yl}-ethanone;
2-(3,5-Dimethyl-[1,2,4]triazol-1-yl)-1-{(R)-2-methyl-4-[5-trifluoromethyl-2-(2-trifluoromethyl-pyrimidin-5-yl)-1,2,3,4-tetrahydro-isoquinolin-8-yl]-piperazin-1-yl}-ethanone;
8-[(R)-4-(2-Imidazo[4,5-b]pyridin-3-yl-acetyl)-3-methyl-piperazin-1-yl]-3,4-dihydro-1H-isoquinoline-2-carboxylic acid benzyl ester;
1-[(R)-4-(2-Cyclopropanecarbonyl-1,2,3,4-tetrahydro-isoquinolin-8-yl)-2-methyl-piperazin-1-yl]-2-imidazo[4,5-b]pyridin-3-yl-ethanone;
2-Imidazo[4,5-b]pyridin-3-yl-1-{(R)-4-[2-(4-methoxy-benzoyl)-1,2,3,4-tetrahydro-isoquinolin-8-yl]-2-methyl-piperazin-1-yl}-ethanone;
2-Imidazo[4,5-b]pyridin-3-yl-1-{(R)-2-methyl-4-[2-(2-pyridin-3-yl-acetyl)-1,2,3,4-tetrahydro-isoquinolin-8-yl]-piperazin-1-yl}-ethanone;
1-{8-[(R)-4-(2-Imidazo[4,5-b]pyridin-3-yl-acetyl)-3-methyl-piperazin-1-yl]-3,4-dihydro-1H-isoquinolin-2-yl}-3-(4-methoxy-phenyl)-propan-1-one;
2-Imidazo[4,5-b]pyridin-3-yl-1-{(R)-2-methyl-4-[2-(oxazole-4-carbonyl)-1,2,3,4-tetrahydro-isoquinolin-8-yl]-piperazin-1-yl}-ethanone;

2-Imidazo[4,5-b]pyridin-3-yl-1-{(R)-4-[2-(2-indol-1-yl-acetyl)-1,2,3,4-tetrahydro-isoquinolin-8-yl]-2-methyl-piperazin-1-yl}-ethanone;

1-{8-[(R)-4-(2-Imidazo[4,5-b]pyridin-3-yl-acetyl)-3-methyl-piperazin-1-yl]-3,4-dihydro-1H-isoquinolin-2-yl}-2-methyl-propan-1-one;

2-Imidazo[4,5-b]pyridin-3-yl-1-{(R)-4-[2-(2-methoxy-acetyl)-1,2,3,4-tetrahydro-isoquinolin-8-yl]-2-methyl-piperazin-1-yl}-ethanone;

1-[(R)-4-(2-Cyclopentanecarbonyl-1,2,3,4-tetrahydro-isoquinolin-8-yl)-2-methyl-piperazin-1-yl]-2-imidazo[4,5-b]pyridin-3-yl-ethanone;

1-[(R)-4-(2-Cyclohexanecarbonyl-1,2,3,4-tetrahydro-isoquinolin-8-yl)-2-methyl-piperazin-1-yl]-2-imidazo[4,5-b]pyridin-3-yl-ethanone;

2-Imidazo[4,5-b]pyridin-3-yl-1-{(R)-2-methyl-4-[2-((R)-1,2,3,4-tetrahydro-naphthalene-1-carbonyl)-1,2,3,4-tetrahydro-isoquinolin-8-yl]-piperazin-1-yl}-ethanone;

1-[(R)-4-(2-Benzoyl-1,2,3,4-tetrahydro-isoquinolin-8-yl)-2-methyl-piperazin-1-yl]-2-imidazo[4,5-b]pyridin-3-yl-ethanone;

2-Imidazo[4,5-b]pyridin-3-yl-1-{(R)-2-methyl-4-[2-(4-methyl-benzoyl)-1,2,3,4-tetrahydro-isoquinolin-8-yl]-piperazin-1-yl}-ethanone;

1-{(R)-4-[2-(4-Chloro-benzoyl)-1,2,3,4-tetrahydro-isoquinolin-8-yl]-2-methyl-piperazin-1-yl}-2-imidazo[4,5-b]pyridin-3-yl-ethanone;

1-{(R)-4-[2-(3,4-Dichloro-benzoyl)-1,2,3,4-tetrahydro-isoquinolin-8-yl]-2-methyl-piperazin-1-yl}-2-imidazo[4,5-b]pyridin-3-yl-ethanone;

1-{(R)-4-[2-(3-Dimethylamino-benzoyl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(4-trifluoromethyl-benzoyl)-1,2,3,4-tetrahydro-isoquinolin-8-yl]-piperazin-1-yl}-ethanone;

2-Imidazo[4,5-b]pyridin-3-yl-1-[(R)-2-methyl-4-(2-phenylacetyl-1,2,3,4-tetrahydro-isoquinolin-8-yl)-piperazin-1-yl]-ethanone;

(R)-1-{8-[(R)-4-(2-Imidazo[4,5-b]pyridin-3-yl-acetyl)-3-methyl-piperazin-1-yl]-3,4-dihydro-1H-isoquinolin-2-yl}-2-phenyl-propan-1-one;

2-Imidazo[4,5-b]pyridin-3-yl-1-{(R)-2-methyl-4-[2-(1-phenyl-cyclopropanecarbonyl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(2-phenoxy-acetyl)-1,2,3,4-tetrahydro-isoquinolin-8-yl]-piperazin-1-yl}-ethanone;

3-(4-Chloro-phenyl)-1-{8-[(R)-4-(2-imidazo[4,5-b]pyridin-3-yl-acetyl)-3-methyl-piperazin-1-yl]-3,4-dihydro-1H-isoquinolin-2-yl}-propan-1-one;

1-{8-[(R)-4-(2-Imidazo[4,5-b]pyridin-3-yl-acetyl)-3-methyl-piperazin-1-yl]-3,4-dihydro-1H-isoquinolin-2-yl}-3-phenyl-propan-1-one;

3-(3,4-Dichloro-phenyl)-1-{8-[(R)-4-(2-imidazo[4,5-b]pyridin-3-yl-acetyl)-3-methyl-piperazin-1-yl]-3,4-dihydro-1H-isoquinolin-2-yl}-propan-1-one;

2-Imidazo[4,5-b]pyridin-3-yl-1-{(R)-2-methyl-4-[2-(quinoline-6-carbonyl)-1,2,3,4-tetrahydro-isoquinolin-8-yl]-piperazin-1-yl}-ethanone;

1-{(R)-4-[2-(2-Benzoimidazol-1-yl-acetyl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(2-pyrazol-1-yl-acetyl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(2-morpholin-4-yl-acetyl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(2-methyl-2H-pyrazole-3-carbonyl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(5-methyl-pyridin-2-yl)-1,2,3,4-tetrahydro-isoquinolin-8-yl]-piperazin-1-yl}-ethanone;

1-{(R)-4-[2-(5-Fluoro-pyridin-2-yl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(6-methyl-pyridin-3-yl)-1,2,3,4-tetrahydro-isoquinolin-8-yl]-piperazin-1-yl}-ethanone;

1-{(R)-4-[2-(4-Chloro-phenyl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-4-[2-(2-methoxy-phenyl)-1,2,3,4-tetrahydro-isoquinolin-8-yl]-2-methyl-piperazin-1-yl}-ethanone;

4-{8-[(R)-4-(2-Imidazo[4,5-b]pyridin-3-yl-acetyl)-3-methyl-piperazin-1-yl]-3,4-dihydro-1H-isoquinolin-2-yl}-benzonitrile;

2-Imidazo[4,5-b]pyridin-3-yl-1-{(R)-2-methyl-4-[2-(4-trifluoromethyl-phenyl)-1,2,3,4-tetrahydro-isoquinolin-8-yl]-piperazin-1-yl}-ethanone;

2-Imidazo[4,5-b]pyridin-3-yl-1-{(R)-4-[2-(3-methoxy-phenyl)-1,2,3,4-tetrahydro-isoquinolin-8-yl]-2-methyl-piperazin-1-yl}-ethanone;

2-Imidazo[4,5-b]pyridin-3-yl-1-{(R)-2-methyl-4-[2-(4-trifluoromethoxy-phenyl)-1,2,3,4-tetrahydro-isoquinolin-8-yl]-piperazin-1-yl}-ethanone;

1-{(R)-4-[2-(4-Fluoro-phenyl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(6-trifluoromethyl-pyridin-3-yl)-1,2,3,4-tetrahydro-isoquinolin-8-yl]-piperazin-1-yl}-ethanone;

2-Imidazo[4,5-b]pyridin-3-yl-1-[(R)-2-methyl-4-(2-phenyl-1,2,3,4-tetrahydro-isoquinolin-8-yl)-piperazin-1-yl]-ethanone;

2-Imidazo[4,5-b]pyridin-3-yl-1-[(R)-2-methyl-4-(2-pyrimidin-2-yl-1,2,3,4-tetrahydro-isoquinolin-8-yl)-piperazin-1-yl]-ethanone;

2-Imidazo[4,5-b]pyridin-3-yl-1-{(R)-2-methyl-4-[2-(5-trifluoromethyl-pyridin-2-yl)-1,2,3,4-tetrahydro-isoquinolin-8-yl]-piperazin-1-yl}-ethanone;

2-Imidazo[4,5-b]pyridin-3-yl-1-[(R)-2-methyl-4-(2-pyridin-2-yl-1,2,3,4-tetrahydro-isoquinolin-8-yl)-piperazin-1-yl]-ethanone;

2-Imidazo[4,5-b]pyridin-3-yl-1-{(R)-4-[2-(4-methoxy-phenyl)-1,2,3,4-tetrahydro-isoquinolin-8-yl]-2-methyl-piperazin-1-yl}-ethanone;

2-Imidazo[4,5-b]pyridin-3-yl-1-[(R)-2-methyl-4-(2-pyrimidin-5-yl-1,2,3,4-tetrahydro-isoquinolin-8-yl)-piperazin-1-yl]-ethanone;

2-Imidazo[4,5-b]pyridin-3-yl-1-{(R)-2-methyl-4-[2-(2-trifluoromethyl-pyrimidin-5-yl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(5-methyl-pyrimidin-2-yl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(2-methyl-pyrimidin-5-yl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(2-propyl-pyrimidin-5-yl)-1,2,3,4-tetrahydro-isoquinolin-8-yl]-piperazin-1-yl}-ethanone;

2-Imidazo[4,5-b]pyridin-3-yl-1-{(R)-4-[2-(2-isopropoxy-pyrimidin-5-yl)-1,2,3,4-tetrahydro-isoquinolin-8-yl]-2-methyl-piperazin-1-yl}-ethanone;

2-Imidazo[4,5-b]pyridin-3-yl-1-((R)-2-methyl-4-{2-[2-(2,2,2-trifluoro-ethoxy)-pyrimidin-5-yl]-1,2,3,4-tetrahydro-isoquinolin-8-yl}-piperazin-1-yl)-ethanone;

2-Imidazo[4,5-b]pyridin-3-yl-1-[(R)-2-methyl-4-(2-thiazol-2-yl-1,2,3,4-tetrahydro-isoquinolin-8-yl)-piperazin-1-yl]-ethanone;

2-Imidazo[4,5-b]pyridin-3-yl-1-{(R)-2-methyl-4-[2-(4-methyl-thiazol-2-yl)-1,2,3,4-tetrahydro-isoquinolin-8-yl]-piperazin-1-yl}-ethanone;

2-Imidazo[4,5-b]pyridin-3-yl-1-{(R)-2-methyl-4-[2-(5-phenyl-thiazol-2-yl)-1,2,3,4-tetrahydro-isoquinolin-8-yl]-piperazin-1-yl}-ethanone;

1-{(R)-4-[2-(4,5-Dimethyl-thiazol-2-yl)-1,2,3,4-tetrahydro-isoquinolin-8-yl]-2-methyl-piperazin-1-yl}-2-imidazo[4,5-b]pyridin-3-yl-ethanone;

2-{8-[(R)-4-(2-Imidazo[4,5-b]pyridin-3-yl-acetyl)-3-methyl-piperazin-1-yl]-3,4-dihydro-1H-isoquinolin-2-yl}-thiazole-4-carbonitrile;

2-Imidazo[4,5-b]pyridin-3-yl-1-{(R)-4-[2-(2-methoxy-pyrimidin-5-yl)-1,2,3,4-tetrahydro-isoquinolin-8-yl]-2-methyl-piperazin-1-yl}-ethanone;

2-Imidazo[4,5-b]pyridin-3-yl-1-{(R)-4-[2-(6-methoxy-pyridazin-3-yl)-1,2,3,4-tetrahydro-isoquinolin-8-yl]-2-methyl-piperazin-1-yl}-ethanone;

2-Imidazo[4,5-b]pyridin-3-yl-1-{(R)-4-[2-(6-methoxy-pyrazin-2-yl)-1,2,3,4-tetrahydro-isoquinolin-8-yl]-2-methyl-piperazin-1-yl}-ethanone;

1-{(R)-4-[2-(4,6-Dimethoxy-[1,3,5]triazin-2-yl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-4-[2-(2-methoxy-pyrimidin-4-yl)-1,2,3,4-tetrahydro-isoquinolin-8-yl]-2-methyl-piperazin-1-yl}-ethanone;

1-{(R)-4-[2-(2-Ethoxy-pyrimidin-5-yl)-1,2,3,4-tetrahydro-isoquinolin-8-yl]-2-methyl-piperazin-1-yl}-2-imidazo[4,5-b]pyridin-3-yl-ethanone;

2-Imidazo[4,5-b]pyridin-3-yl-1-{(R)-2-methyl-4-[2-(4-phenyl-thiazol-2-yl)-1,2,3,4-tetrahydro-isoquinolin-8-yl]-piperazin-1-yl}-ethanone;

2-(3,5-Dimethyl-[1,2,4]triazol-1-yl)-1-{(R)-2-methyl-4-[2-(2-trifluoromethyl-pyrimidin-5-yl)-1,2,3,4-tetrahydro-isoquinolin-8-yl]-piperazin-1-yl}-ethanone;

1-{(R)-4-[2-(2-Cyclopropyl-pyrimidin-5-yl)-1,2,3,4-tetrahydro-isoquinolin-8-yl]-2-methyl-piperazin-1-yl}-2-(3,5-dimethyl-[1,2,4]triazol-1-yl)-ethanone;

2-(3,5-Dimethyl-[1,2,4]triazol-1-yl)-1-{(R)-4-[2-(2-ethoxy-pyrimidin-5-yl)-1,2,3,4-tetrahydro-isoquinolin-8-yl]-2-methyl-piperazin-1-yl}-ethanone;

2-(3,5-Dimethyl-pyrazol-1-yl)-1-{(R)-4-[2-(2-ethoxy-pyrimidin-5-yl)-1,2,3,4-tetrahydro-isoquinolin-8-yl]-2-methyl-piperazin-1-yl}-ethanone;

1-{(R)-4-[2-(2-Ethoxy-pyrimidin-5-yl)-5-fluoro-1,2,3,4-tetrahydro-isoquinolin-8-yl]-2-methyl-piperazin-1-yl}-2-imidazo[4,5-b]pyridin-3-yl-ethanone;

2-(3,5-Dimethyl-pyrazol-1-yl)-1-{(R)-4-[2-(2-ethoxy-pyrimidin-5-yl)-5-fluoro-1,2,3,4-tetrahydro-isoquinolin-8-yl]-2-methyl-piperazin-1-yl}-ethanone;

2-(3,5-Dimethyl-[1,2,4]triazol-1-yl)-1-{(R)-4-[2-(2-ethoxy-pyrimidin-5-yl)-5-fluoro-1,2,3,4-tetrahydro-isoquinolin-8-yl]-2-methyl-piperazin-1-yl}-ethanone;

2-(3,5-Dimethyl-[1,2,4]triazol-1-yl)-1-{(R)-4-[5-fluoro-2-(2-trifluoromethyl-pyrimidin-5-yl)-1,2,3,4-tetrahydro-isoquinolin-8-yl]-2-methyl-piperazin-1-yl}-ethanone;

1-{(R)-4-[2-(2-Cyclopropyl-pyrimidin-5-yl)-5-fluoro-1,2,3,4-tetrahydro-isoquinolin-8-yl]-2-methyl-piperazin-1-yl}-2-(3,5-dimethyl-[1,2,4]triazol-1-yl)-ethanone;

1-{(R)-4-[2-(2-Ethoxy-pyrimidin-5-yl)-6-trifluoromethyl-1,2,3,4-tetrahydro-isoquinolin-8-yl]-2-methyl-piperazin-1-yl}-2-imidazo[4,5-b]pyridin-3-yl-ethanone;

8-[(R)-3-Methyl-4-(2-pyrazol-1-yl-acetyl)-piperazin-1-yl]-3,4-dihydro-1H-isoquinoline-2-carboxylic acid benzyl ester;

8-{(R)-4-[2-(3,5-Dimethyl-[1,2,4]triazol-1-yl)-acetyl]-3-methyl-piperazin-1-yl}-3,4-dihydro-1H-isoquinoline-2-carboxylic acid benzyl ester;

8-[4-(2-Imidazo[4,5-b]pyridin-3-yl-acetyl)-piperazin-1-yl]-3,4-dihydro-1H-isoquinoline-2-carboxylic acid benzyl ester;

8-[4-(2-Pyrrolo[2,3-b]pyridin-1-yl-acetyl)-piperazin-1-yl]-3,4-dihydro-1H-isoquinoline-2-carboxylic acid benzyl ester;

8-{4-[2-(3-Methyl-2-oxo-2,3-dihydro-benzoimidazol-1-yl)-acetyl]-piperazin-1-yl}-3,4-dihydro-1H-isoquinoline-2-carboxylic acid benzyl ester;

1-{2-[4-(2-Benzoyl-1,2,3,4-tetrahydro-isoquinolin-8-yl)-piperazin-1-yl]-2-oxo-ethyl}-3-methyl-1,3-dihydro-benzoimidazol-2-one;

1-Methyl-3-{2-oxo-2-[4-(2-phenylacetyl-1,2,3,4-tetrahydro-isoquinolin-8-yl)-piperazin-1-yl]-ethyl}-1,3-dihydro-benzoimidazol-2-one;

2-Imidazo[4,5-b]pyridin-3-yl-1-[4-(2-phenylmethanesulfonyl-1,2,3,4-tetrahydro-isoquinolin-8-yl)-piperazin-1-yl]-ethanone;

1-{(R)-4-[2-(4-Chloro-benzyl)-1,2,3,4-tetrahydro-isoquinolin-8-yl]-2-methyl-piperazin-1-yl}-2-imidazo[4,5-b]pyridin-3-yl-ethanone;

5-Bromo-8-[(R)-4-(2-imidazo[4,5-b]pyridin-3-yl-acetyl)-3-methyl-piperazin-1-yl]-3,4-dihydro-1H-isoquinoline-2-carboxylic acid benzyl ester;

8-[(R)-4-(2-Imidazo[4,5-b]pyridin-3-yl-acetyl)-3-methyl-piperazin-1-yl]-5-trifluoromethyl-3,4-dihydro-1H-isoquinoline-2-carboxylic acid benzyl ester;

5-Cyano-8-[(R)-4-(2-imidazo[4,5-b]pyridin-3-yl-acetyl)-3-methyl-piperazin-1-yl]-3,4-dihydro-1H-isoquinoline-2-carboxylic acid benzyl ester; or 1-{(R)-4-[5,6-Difluoro-2-(2-trifluoromethyl-pyrimidin-5-yl)-1,2,3,4-tetrahydro-isoquinolin-8-yl]-2-methyl-piperazin-1-yl}-2-(3,5-dimethyl-[1,2,4]triazol-1-yl)-ethanone;

or a salt thereof.

12. A pharmaceutical composition comprising, as active principle, the compound according to claim 1, or a pharmaceutically acceptable salt thereof, and at least one therapeutically inert excipient.

13. The compound according to claim 1, or a pharmaceutically acceptable salt thereof, formulated as a medicament.

14. A method of treating a disease comprising administering to a subject in need thereof the compound according to claim 1, or a pharmaceutically acceptable salt thereof, wherein the disease is rheumatoid arthritis or psoriasis.

15. A method of treating a disease comprising administering to a subject in need thereof the compound according to claim 11, or a pharmaceutically acceptable salt thereof, wherein the disease is rheumatoid arthritis or psoriasis.

\* \* \* \* \*